(12) United States Patent
Fung

(10) Patent No.: US 11,771,955 B2
(45) Date of Patent: Oct. 3, 2023

(54) SYSTEM AND METHOD FOR NEUROLOGICAL FUNCTION ANALYSIS AND TREATMENT USING VIRTUAL REALITY SYSTEMS

(71) Applicant: Blue Goji LLC, Austin, TX (US)

(72) Inventor: Coleman Fung, Austin, TX (US)

(73) Assignee: BLUE GOJI LLC, Austin, TX (US)

(*) Notice: Subject to any disclaimer, the term of this patent is extended or adjusted under 35 U.S.C. 154(b) by 0 days.

(21) Appl. No.: 18/089,467

(22) Filed: Dec. 27, 2022

(65) Prior Publication Data

US 2023/0116214 A1  Apr. 13, 2023

Related U.S. Application Data

(63) Continuation-in-part of application No. 17/963,494, filed on Oct. 11, 2022, which is a continuation-in-part
(Continued)

(51) Int. Cl.
| | |
|---|---|
| A63B 22/00 | (2006.01) |
| A63B 23/00 | (2006.01) |
| G06T 19/00 | (2011.01) |
| A63F 13/212 | (2014.01) |
| G06F 3/01 | (2006.01) |
| A63B 24/00 | (2006.01) |
| A63B 22/02 | (2006.01) |
| A63B 23/04 | (2006.01) |
| G06F 1/16 | (2006.01) |

(Continued)

(52) U.S. Cl.
CPC ...... *A63B 24/0003* (2013.01); *A63B 22/0046* (2013.01); *A63B 22/0285* (2013.01); *A63B 22/0292* (2015.10); *A63B 22/06* (2013.01); *A63B 23/04* (2013.01); *A63F 13/212* (2014.09); *A63F 13/214* (2014.09); *A63F 13/40* (2014.09); *A63F 13/65* (2014.09); *G06F 1/163* (2013.01); *G06F 3/011* (2013.01); *G06F 3/016* (2013.01); *G06T 19/006* (2013.01); *H04W 84/18* (2013.01)

(58) Field of Classification Search
None
See application file for complete search history.

(56) References Cited

U.S. PATENT DOCUMENTS

2017/0213473 A1* 7/2017 Ribeira ............... G09B 5/10
2017/0372640 A1* 12/2017 Lampotang .......... G09B 9/00
(Continued)

*Primary Examiner* — Tize Ma
(74) *Attorney, Agent, or Firm* — Galvin Patent Law LLC; Brian R. Galvin

(57) ABSTRACT

A system and method for providing neurological function analysis and treatment to a person using virtual reality systems. The system and methods comprise a data capture system that receives, fuses, and integrates sensor data from various sensors, a virtual reality engine which uses the integrated sensor information to generate an environmental model and a tracking model, and a therapeutic engine which can assess both the cognitive and physical condition the person, determine a training regime based on the assessment, and apply therapies while the person is engaged in a virtual reality environment. The training regimen can comprise brainwave entrainment and/or dual-task stimulation via virtual elements. In some embodiments, a medical professional may engage with the person in the virtual reality environment.

16 Claims, 57 Drawing Sheets

Related U.S. Application Data of application No. 17/575,600, filed on Jan. 13, 2022, now Pat. No. 11,465,013, which is a continuation-in-part of application No. 16/951,281, filed on Nov. 18, 2020, now Pat. No. 11,123,604, which is a continuation of application No. 17/030,195, filed on Sep. 23, 2020, which is a continuation-in-part of application No. 16/781,663, filed on Feb. 4, 2020, now Pat. No. 11,191,996, which is a continuation-in-part of application No. 16/354,374, filed on Mar. 15, 2019, now Pat. No. 10,549,153, which is a continuation-in-part of application No. 16/176,511, filed on Oct. 31, 2018, now Pat. No. 10,960,264, which is a continuation-in-part of application No. 16/011,394, filed on Jun. 18, 2018, now Pat. No. 10,155,133, which is a continuation-in-part of application No. 15/853,746, filed on Dec. 23, 2017, now Pat. No. 10,265,578, which is a continuation of application No. 15/219,115, filed on Jul. 25, 2016, now Pat. No. 9,849,333, which is a continuation-in-part of application No. 15/193,112, filed on Jun. 27, 2016, now abandoned, which is a continuation-in-part of application No. 15/187,787, filed on Jun. 21, 2016, now Pat. No. 10,124,255, which is a continuation-in-part of application No. 15/175,043, filed on Jun. 7, 2016, now Pat. No. 9,766,696, said application No. 15/187,787 is a continuation-in-part of application No. 14/846,966, filed on Sep. 7, 2015, now Pat. No. 10,080,958, and a continuation-in-part of application No. 14/012,879, filed on Aug. 28, 2013, now Pat. No. 10,737,175, said application No. 17/575,600 is a continuation-in-part of application No. 17/030,233, filed on Sep. 23, 2020, now Pat. No. 11,662,818, which is a continuation-in-part of application No. 17/030,195, filed on Sep. 23, 2020, and a continuation-in-part of application No. 16/927,704, filed on Jul. 13, 2020, now abandoned, which is a continuation of application No. 16/867,238, filed on May 5, 2020, now abandoned, which is a continuation-in-part of application No. 16/793,915, filed on Feb. 18, 2020, now abandoned, which is a continuation-in-part of application No. 16/255,641, filed on Jan. 23, 2019, now Pat. No. 10,561,900, which is a continuation of application No. 16/223,034, filed on Jan. 23, 2019, now Pat. No. 10,688,341, which is a continuation-in-part of application No. 16/176,511, filed on Oct. 31, 2018, now Pat. No. 10,960,264, application No. 18/089,467 is a continuation-in-part of application No. 17/888,449, filed on Aug. 15, 2022, which is a continuation of application No. 17/575,600, filed on Jan. 13, 2022, now Pat. No. 11,465,013, application No. 18/089,467 is a continuation-in-part of application No. 17/592,866, filed on Feb. 4, 2022, now Pat. No. 11,517,709, which is a continuation of application No. 17/574,540, filed on Jan. 12, 2022, now Pat. No. 11,524,209.

(60) Provisional application No. 62/697,973, filed on Jul. 13, 2018, provisional application No. 62/330,602, filed on May 2, 2016, provisional application No. 62/330,642, filed on May 2, 2016, provisional application No. 62/310,568, filed on Mar. 18, 2016, provisional application No. 61/696,068, filed on Aug. 31, 2012.

(51) Int. Cl.
    *A63F 13/65*     (2014.01)
    *A63F 13/214*     (2014.01)
    *A63F 13/40*     (2014.01)
    *A63B 22/06*     (2006.01)
    *H04W 84/18*     (2009.01)

(56) References Cited

U.S. PATENT DOCUMENTS

| | | |
|---|---|---|
| 2019/0247662 A1 | 8/2019 | Poltroak |
| 2020/0356136 A1 | 11/2020 | Aimone et al. |
| 2022/0404907 A1* | 12/2022 | Rubin ................. H04L 65/1089 |

* cited by examiner

SYSTEM AND METHOD FOR NEUROLOGICAL FUNCTION ANALYSIS AND TREATMENT USING VIRTUAL REALITY SYSTEMS

CROSS-REFERENCE TO RELATED APPLICATIONS

Priority is claimed in the application data sheet to the following patents or patent applications, each of which is expressly incorporated herein by reference in its entirety:
Ser. No. 17/030,233
Ser. No. 16/951,281
Ser. No. 17/030,195
Ser. No. 16/781,663
Ser. No. 16/354,374
Ser. No. 16/176,511
Ser. No. 16/011,394
Ser. No. 15/853,746
Ser. No. 15/219,115
Ser. No. 15/193,112
Ser. No. 15/187,787
Ser. No. 15/175,043
Ser. No. 62/330,602
Ser. No. 62/330,642
Ser. No. 62/310,568
Ser. No. 14/846,966
Ser. No. 14/012,879
Ser. No. 61/696,068
Ser. No. 16/927,704
Ser. No. 16/867,238
Ser. No. 16/793,915
Ser. No. 16/223,034
Ser. No. 62/697,973
Ser. No. 16/255,641

BACKGROUND OF THE INVENTION

Field of the Art

This disclosure relates to the field of health and wellness therapies, and more particularly to systems and methods for neurological function analysis and treatment using virtual reality systems.

Discussion of the State of the Art

Research in medicine and psychology has improved our understanding of neurological function, but has failed to make significant progress in identifying and treating neurological conditions, especially in terms of preventing early cognitive decline and the onset of neurological disorders such as dementia. This lack of significant means to detect and improve neurological conditions has become increasingly important as lifespans in many parts of the world have increased. As the average age of populations has risen, cognitive issues such as dementia have become more common, and advances in identification and treatment have not kept pace. The lack of significant ability to identify and treat neurological conditions affects younger populations, as well, where mental issues such as depression can take a significant toll.

Research highlights the importance of continued neurological stimulation throughout all stages of life including stimulation through physical activity, social connection, and frequent cognitive challenge, but we still lack means for identifying and treating neurological disorders, especially in their early stages. Advancements in and virtual reality systems and environments have created new opportunities for immersive virtual experiences. However, this potential for immersive virtual experiences has not been used for much beyond computer gaming.

What is needed is a system or method for providing neurological function analysis and treatment using virtual reality systems.

SUMMARY OF THE INVENTION

Accordingly, the inventor has conceived and reduced to practice, a system and method for providing neurological function analysis and treatment to a person using virtual reality systems. The system and methods comprise a data capture system that receives, fuses, and integrates sensor data from various sensors, a virtual reality engine which uses the integrated sensor information to generate an environmental model and a tracking model, and a therapeutic engine which can assess both the cognitive and physical condition the person, determine a training regime based on the assessment, and apply therapies while the person is engaged in a virtual reality environment. The training regimen can comprise brainwave entrainment and/or dual-task stimulation via virtual elements. In some embodiments, a medical professional may engage with the person in the virtual reality environment.

According to a preferred embodiment, a system for virtual reality therapy, is disclosed comprising: a computing device comprising a memory, a processor, and a non-volatile data storage device; a virtual reality engine, comprising a first plurality of programming instructions stored in the memory and operating on the processor, wherein the first plurality of programming instructions, when operating on the processor, causes the computing device to: receive sensor data from a plurality of sensors; perform data fusion to integrate the plurality of sensor data; generate an environmental model of a real-world environment based on the integrated sensor data, in which a shared virtual environment is presented to a first person receiving virtual reality therapy and a second person providing the virtual reality therapy; generate a unified tracking model based on the integrated sensor data for each of the first and second persons; for each particular user, apply the environmental model and the tracking model to generate frames of the shared virtual environment corresponding to a real-time field of view of the particular user; receive response data from a therapeutic engine for the first person; perform real-time updates to the shared virtual environment based on first and second person interactions with the shared virtual environment, to movement of users and real objects and surfaces within the real-world space, and the response data; and the therapeutic engine, comprising a second plurality of programming instructions stored in the memory and operating on the processor, wherein the second plurality of programming instructions, when operating on the processor, causes the computing device to: determine a training regimen for the first person, wherein the training regimen comprises one or more training tasks; generate distinct therapeutic layer associated with the first person in the shared virtual environment, wherein the therapeutic layer implements the training regimen; capture the response data to performing one or more of the training tasks; send the response data to the virtual reality engine; and update the therapeutic layer for the first person based on the real-time updates to the shared virtual environment.

According to another preferred embodiment, a method for extended reality therapy with physical interactivity, comprising the steps of: receiving a plurality of sensor data; performing data fusion to integrate the plurality of sensor data; generating an environmental model of a real-world environment based on the integrated sensor data, in which a shared virtual environment is presented to first and second persons; generating a unified tracking model based on the integrated sensor data for each of the first and second persons; for each particular user, applying the environmental model and the tracking model to generate frames of the shared virtual environment corresponding to a real-time field of view of the particular user; receiving user response data from a therapeutic engine; performing real-time updates to the shared virtual environment based on user interaction with the shared virtual environment, to movement of users and real objects and surfaces within the real-world space, and the user response data; for each particular user: determining a training regimen, wherein the training regimen comprises one or more training tasks; generating distinct therapeutic layer associated with the user in the shared virtual environment, wherein the therapeutic layer implements the training regimen; capturing user response data to performing one or more of the training tasks; sending the user response data to the virtual reality engine; and updating the therapeutic layer for each user based on the real-time updates to the shared virtual environment.

According to an aspect of an embodiment, a neurological database is stored on the non-volatile data storage device, the neurological database comprising information about neurological functions, or states, or both, and their associations with primary tasks, or associative activities, or both.

According to an aspect of an embodiment, the one or more tasks comprise a primary task and an associative activity.

According to an aspect of an embodiment, the therapeutic engine is further configured to: receive a neurological assessment for the first person comprising a neurological condition of the first person; select a primary task from the neurological database associated with the neurological condition; select an associative activity from the neurological database associated with the neurological condition; assign a dual task stimulation for the first person to perform, the dual task stimulation comprising the primary task and the associative activity; select a brainwave entrainment therapy for application while the first person is engaged in the dual task stimulation, the therapy comprising a stimulation frequency; and apply the brainwave entrainment therapy by operating virtual elements as transducers at the stimulation frequency while the first person is engaged in the dual task stimulation.

According to an aspect of an embodiment, the primary task is physical exercise and the system further comprises an exercise machine on which the primary task is performed.

According to an aspect of an embodiment, the brainwave entrainment therapy comprises operating the virtual element transducers to provide either visual, auditory, vibratory, or electrical stimulation at a stimulation frequency between 0.5 Hz and 100 Hz.

According to an aspect of an embodiment, a plurality of transducers are used, wherein at least two transducers are of different modalities, and wherein the brainwave entrainment therapy comprises operation of transducers of at least two different modalities.

According to an aspect of an embodiment, a plurality of transducers are used, wherein at least two transducers are of different scales, and wherein the brainwave entrainment therapy comprises operation of transducers of at least two different scales.

According to an aspect of an embodiment, the training regimen comprises brainwave entrainment therapy.

According to an aspect of an embodiment, a scene object model is used to assist the generation of the environmental model.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

Figure 45:
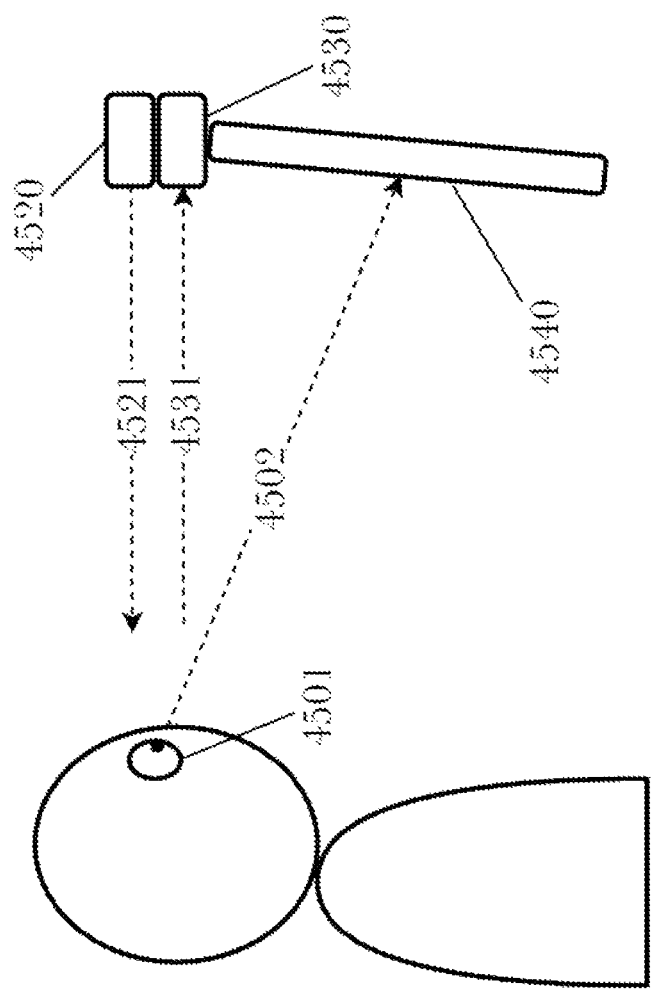
Figure 46:
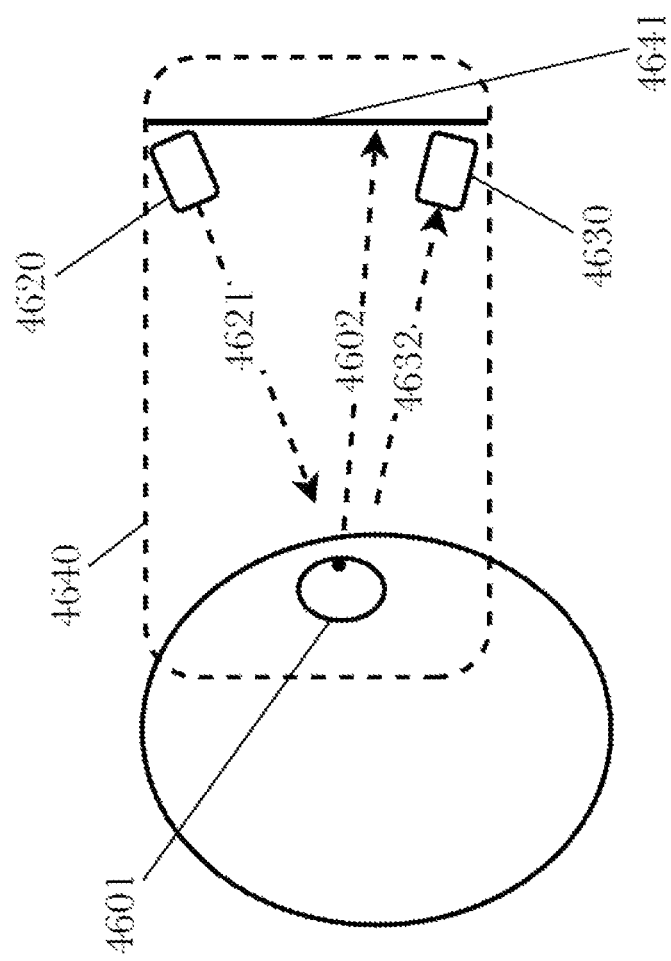
Figure 47:
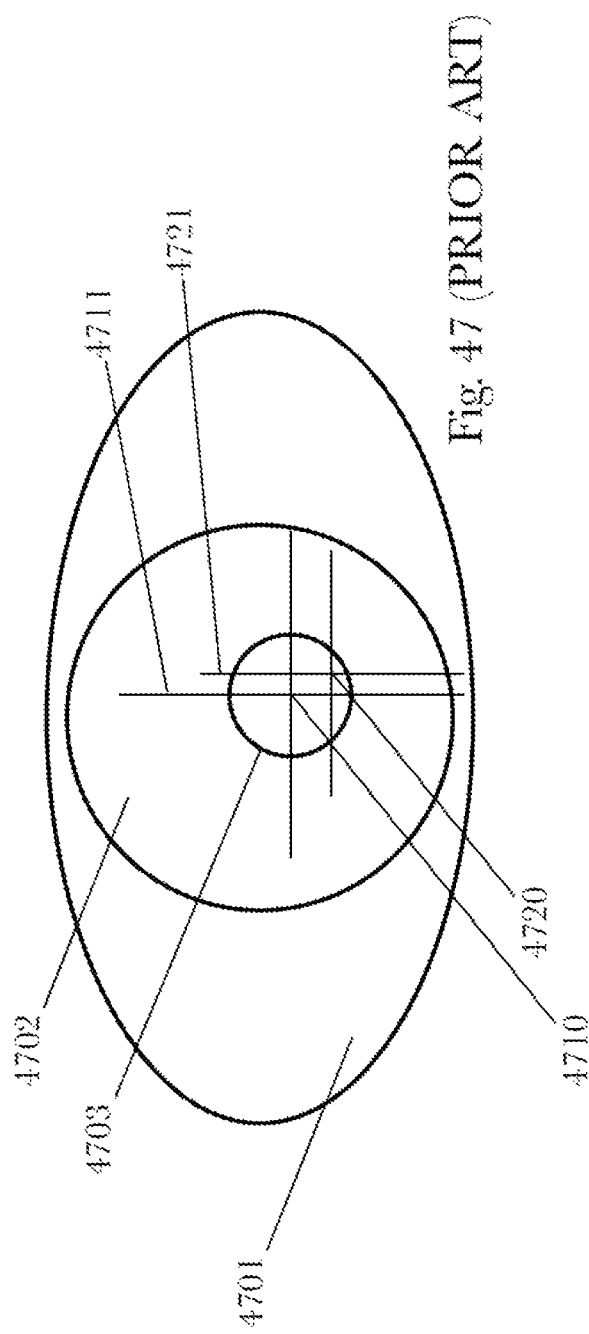

FIGS. 45, 46 & 47 (PRIOR ART) explain the application of eye tracking technology as a means of determining where a user is looking.

Figure 48:
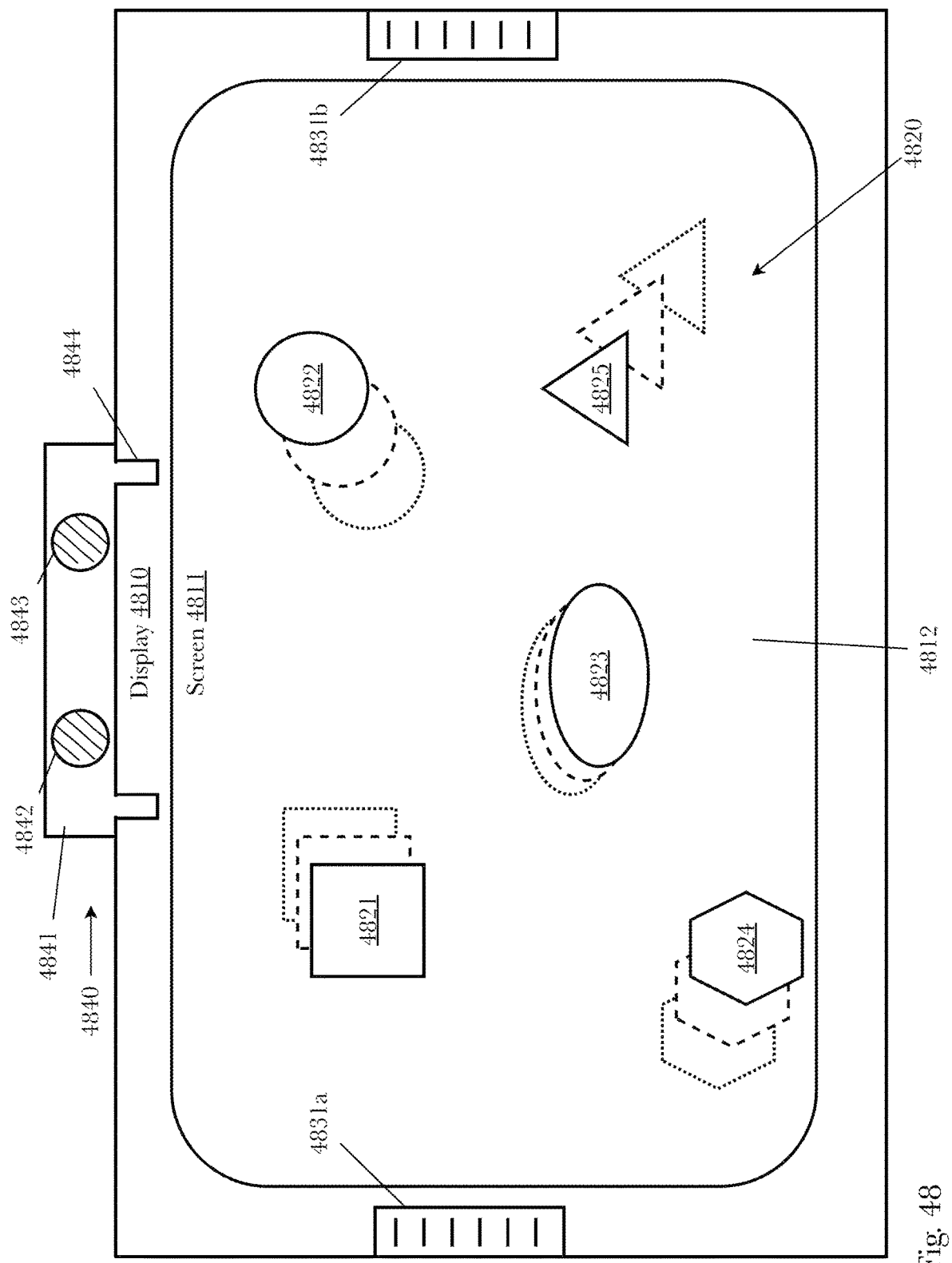

FIG. 48 is a diagram showing an embodiment in which on-screen elements of a display are used to apply brainwave entrainment in conjunction with eye tracking.

Figure 49:
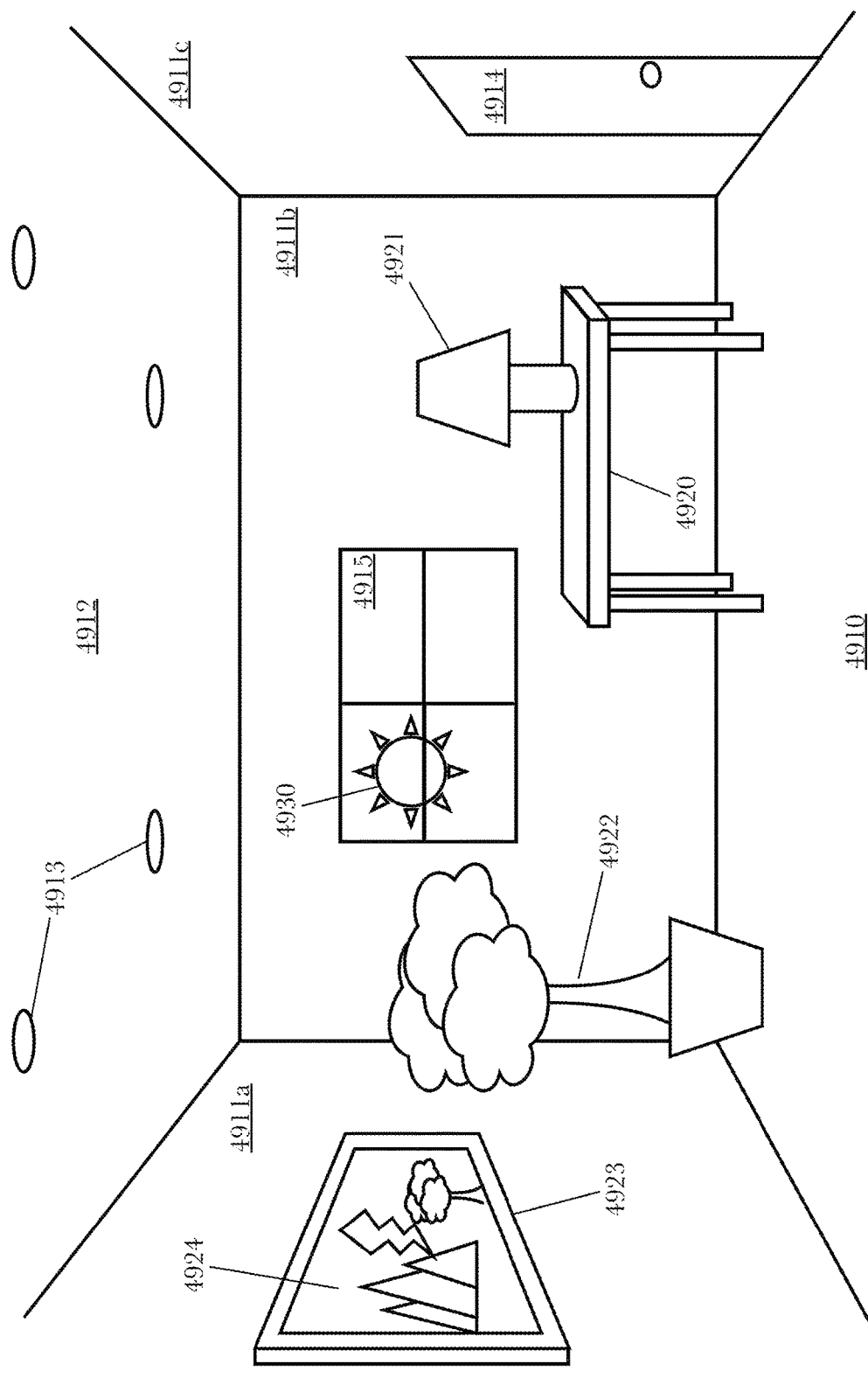

FIG. 49 is a diagram showing an exemplary virtual reality environment in which virtual objects may be used as visual stimulation transducers.

Figure 50:
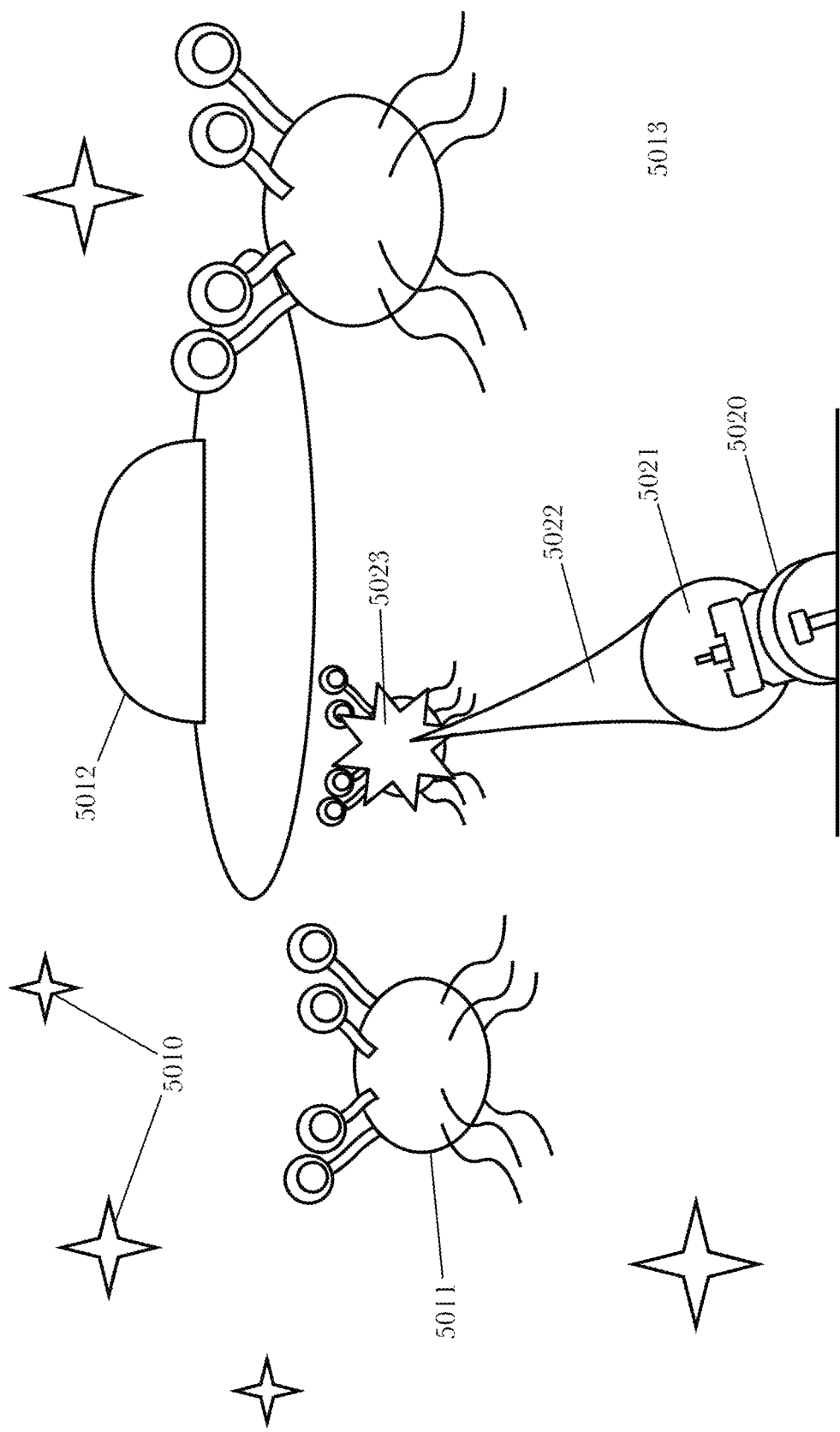

FIG. 50 is a diagram showing exemplary gamification of brainwave entrainment in which in-game objects and elements are used as visual stimulation transducers in conjunction with gameplay activities.

Figure 51:
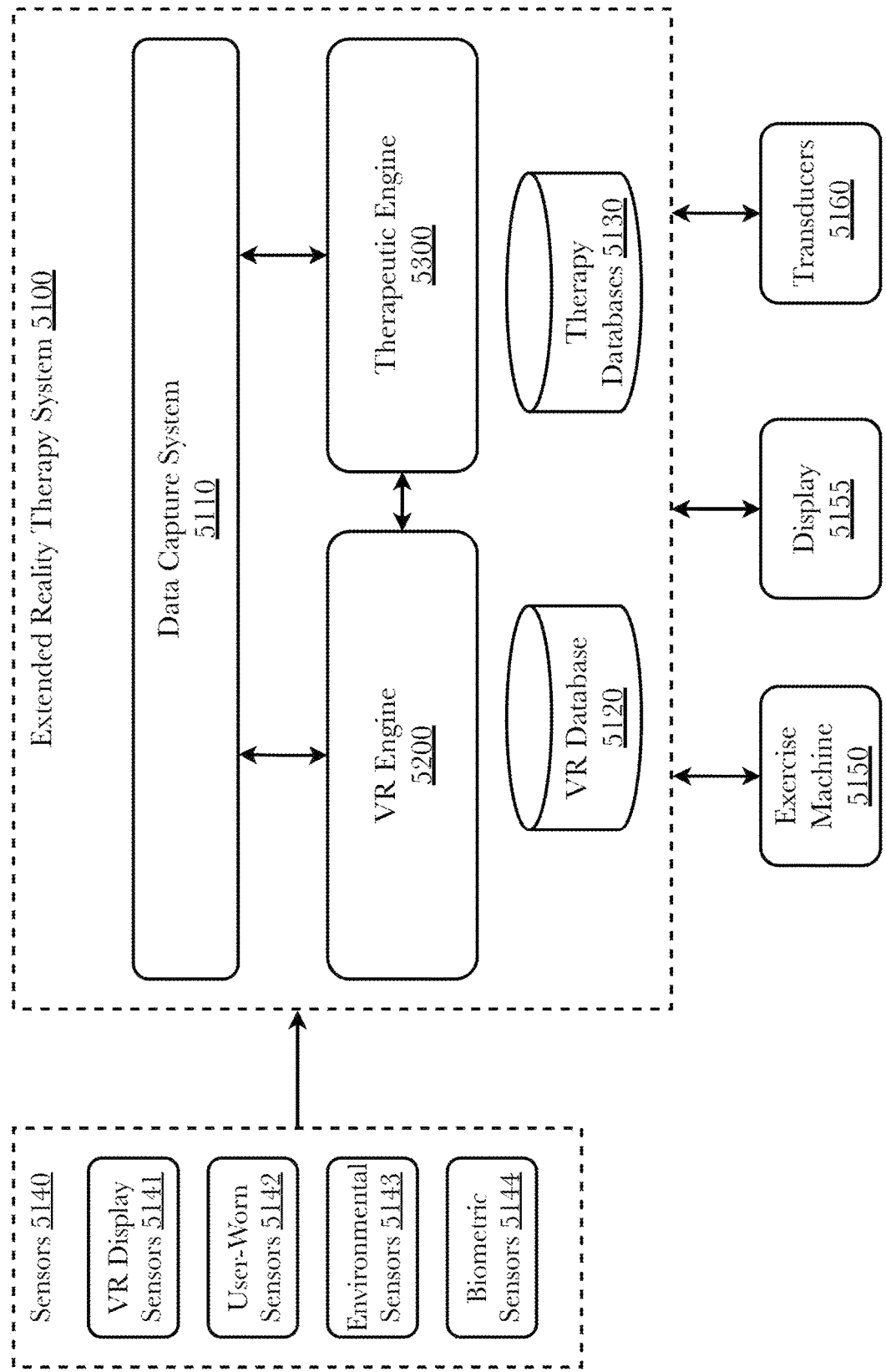

FIG. 51 is a block diagram illustrating an exemplary system architecture for extended reality therapy using physical interactivity, according to an embodiment.

Figure 52:
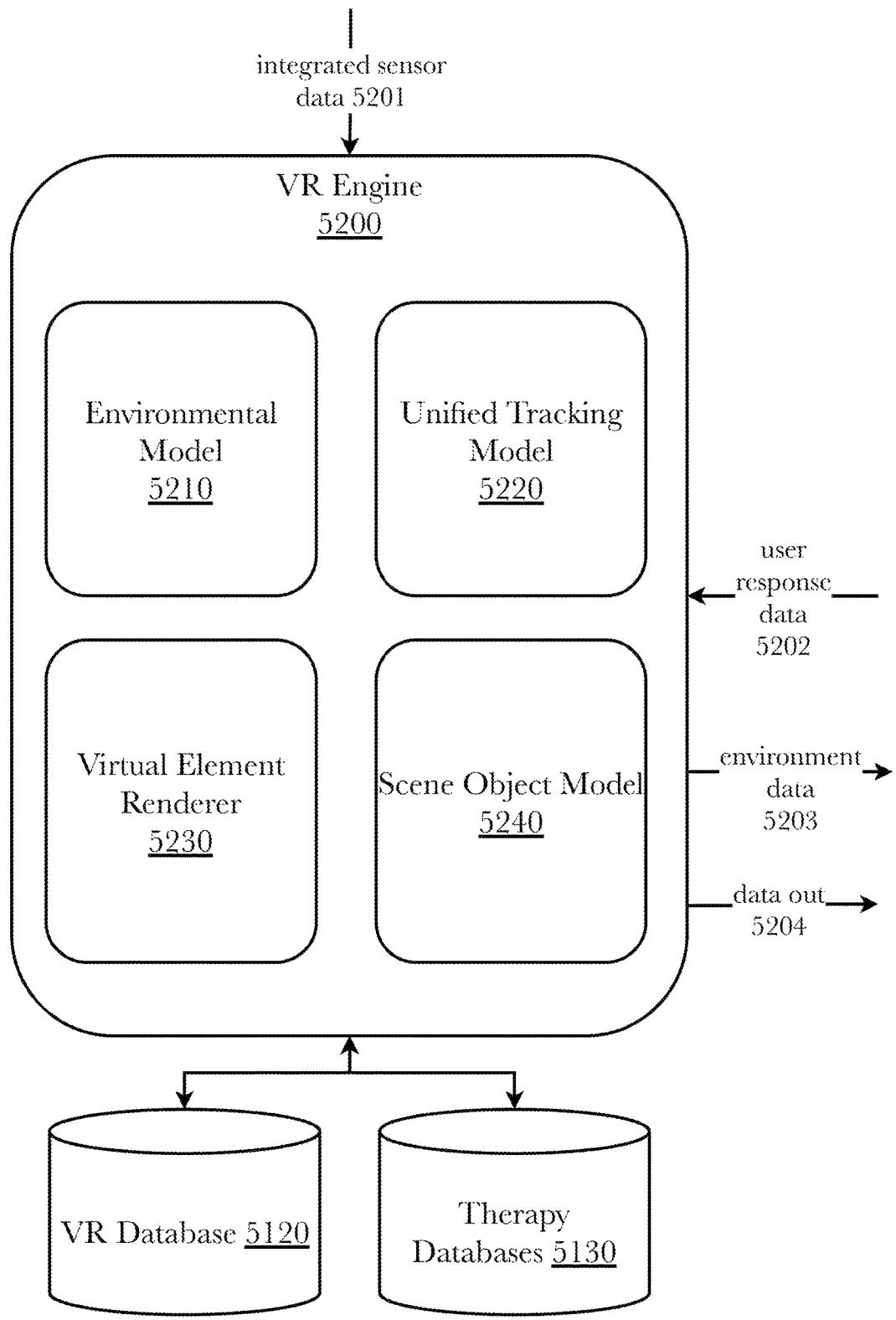

FIG. 52 is a block diagram illustrating an exemplary aspect of the extended reality therapy system, a VR engine.

Figure 53:
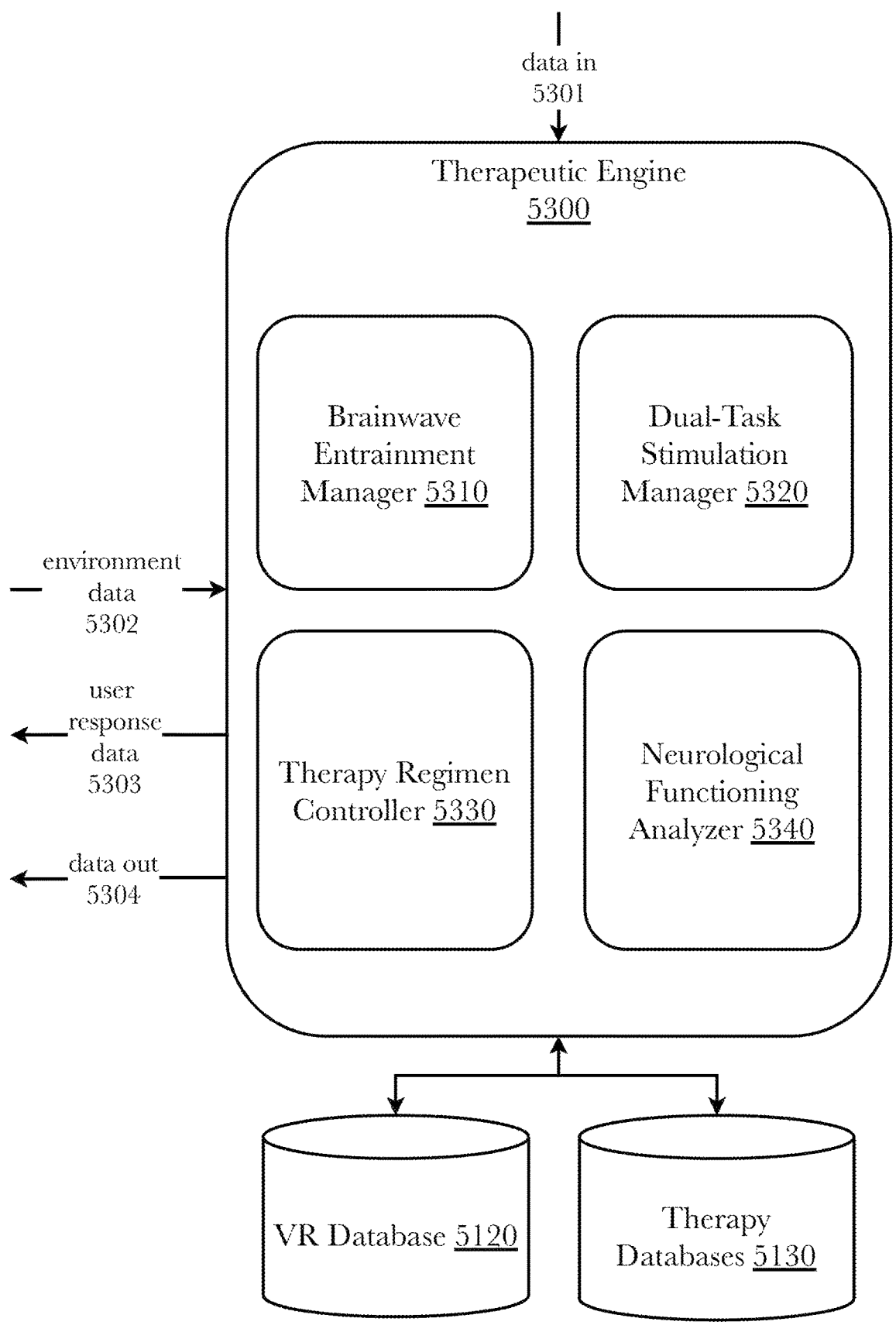

FIG. 53 is a block diagram illustrating an exemplary aspect of the extended reality therapy system, a therapeutic engine.

Figure 54:
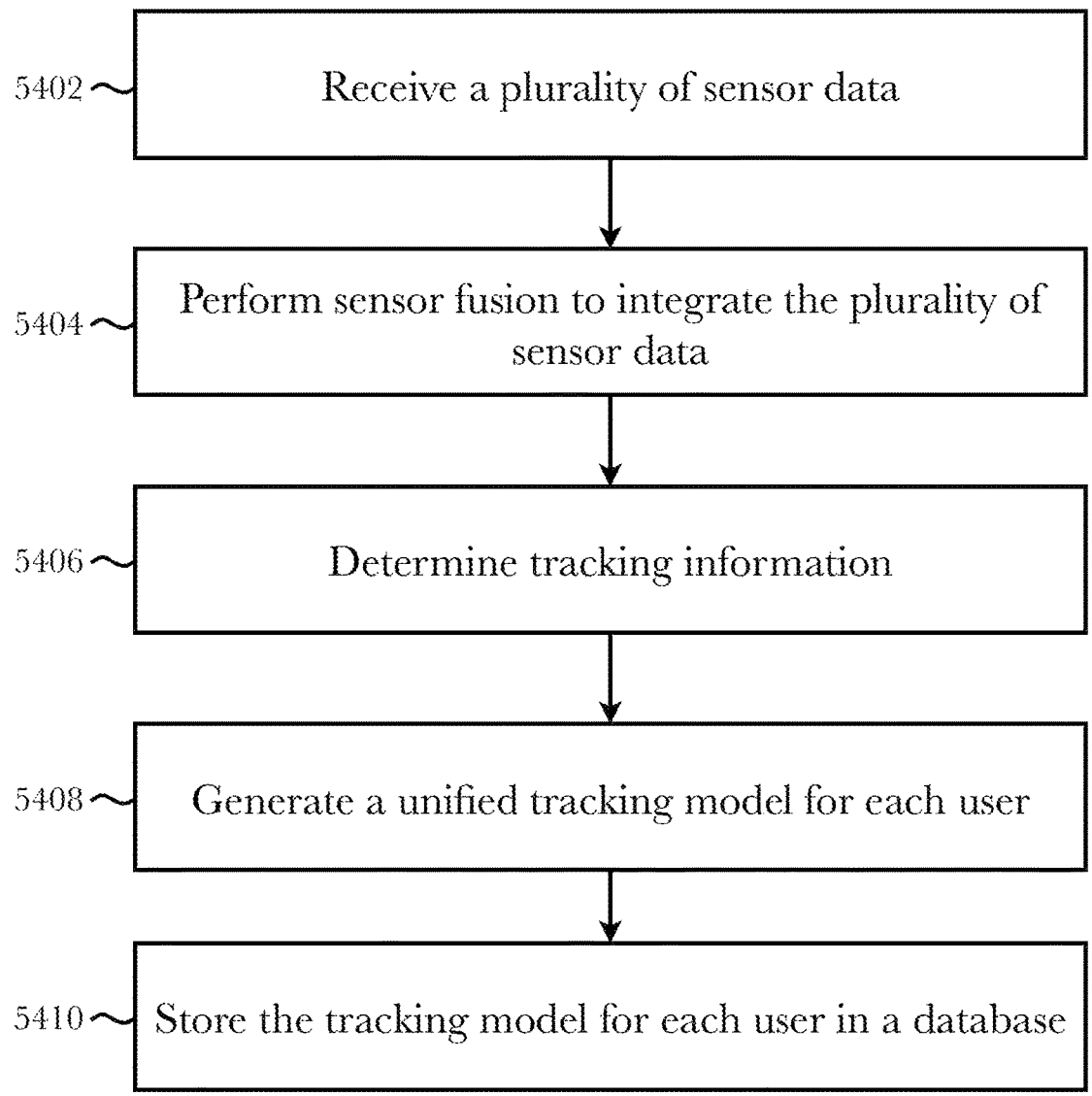

FIG. 54 is a flow diagram illustrating an exemplary process for generating a unified tracking model of a user, according to an aspect.

Figure 55:
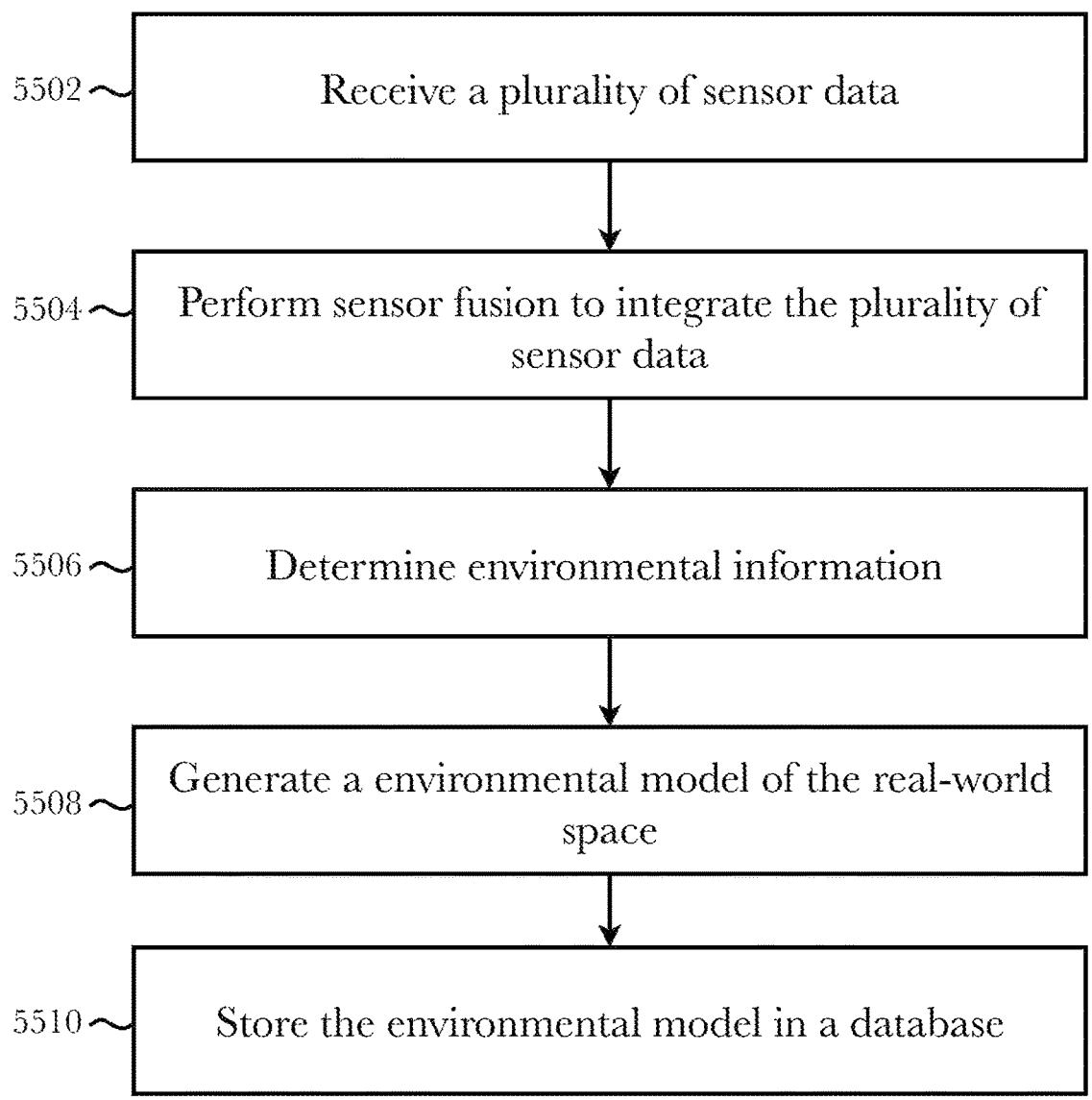

FIG. 55 is a flow diagram illustrating an exemplary process for generating a real-time environmental model of a shared a real-world space, according to an aspect.

Figure 56:
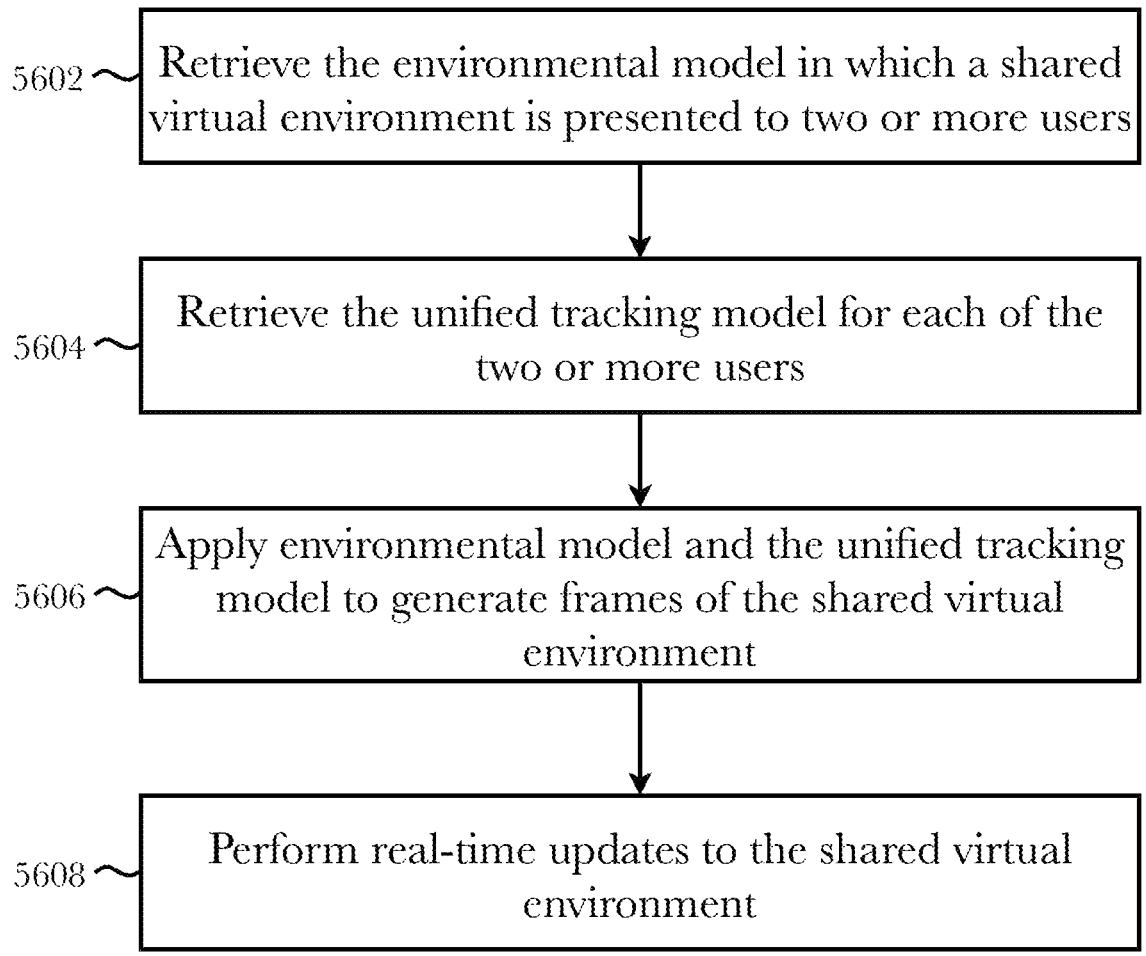

FIG. 56 is a flow diagram illustrating an exemplary process for merging of models to produce a shared virtual environment between two or more users, according to an aspect.

DETAILED DESCRIPTION

The inventor has conceived, and reduced to practice, a system and method for providing neurological function analysis and treatment to a person using virtual reality systems. The system and methods comprise a data capture system that receives, fuses, and integrates sensor data from various sensors, a virtual reality engine which uses the integrated sensor information to generate an environmental model and a tracking model, and a therapeutic engine which can assess both the cognitive and physical condition the person, determine a training regime based on the assessment, and apply therapies while the person is engaged in a virtual reality environment. The training regimen can comprise brainwave entrainment and/or dual-task stimulation via virtual elements. In some embodiments, a medical professional may engage with the person in the virtual reality environment.

Advancements in and virtual reality systems and environments have created new opportunities for immersive virtual experiences. However, this potential for immersive virtual experiences has not been used for much beyond computer gaming. The systems and methods described herein expand the use of virtual reality systems and environments to medical and therapeutic uses including, but not limited to, evaluation and treatment of neurological function. Neurological function includes, but is not limited to, cognitive function and mental function. Cognitive function involves the person's ability to think properly and cognitive impairments include such things as dementia, wherein a person has difficulty remembering things, recognizing things, evaluating things, and understanding things. Mental function involves a person's mental state and mental impairments include such things as depression, wherein a person has feelings of depression, unhappiness, loneliness, and other such negative moods and feelings.

In the systems and methods described herein, neurological function may be evaluated and treated through various means. Two methods described herein in detail are dual-task analysis and brainwave entrainment. Dual-task analysis involves having a person engage simultaneously in a primary task (usually a physical task such as walking on a treadmill) and an associative task (usually a mental task such as counting or identifying things), and determining the influence of the performance of the primary activity on the associative activity and vice-versa. The interplay between the performance characteristics of the two activities can identify areas in which neurological function is impaired (or in some cases enhanced). As an example, changes in a person's walking gait while engaging in mental tasks can indicate impairment of neuro-motor function, while changes in a person's speech ability while engaging in more demanding physical activity can indicate impairment of portions of the brain which control speech production. Brainwave entrainment involves the use of therapeutic stimulation via lights or other stimulators at certain frequencies known to be operative in the brain (brainwave frequencies). Recent research has suggested that visual stimulation of the brain at certain frequencies can have therapeutic benefits for both cognitive impairments such as dementia and mental impairments such as depression. Brainwave entrainment can be applied using virtual reality environments in a number of ways as described herein.

In embodiments where a medical professional or therapist participates with the patient, this type of system design with a shared virtual environment is advantageous in that it allows direct engagement between the medical professional or therapist (e.g., physician, psychologist, coach, trainer, etc.) and a person under treatment, therapy, or coaching (e.g., patient, athlete) within a shared simulated environment. Another advantage of the extended reality therapy system is that it allows for physical therapy to be combined with cognitive therapy to form a multifaceted approach to therapeutic engagement within a shared virtual environment. In some embodiments, the extended reality therapy system may support multiple participants with a shared virtual environment as would be the case, for example, in group therapy sessions, alcoholics anonymous meetings, and the like.

Where brainwave entrainment is part of a group therapy, each person may receive brainwave entrainment treatment distinctly, even though the persons are all in the same virtual world/game (e.g., shared virtual environment). Thus, each person has shared game experience with tailored therapeutic treatment. This results in a shared reality layer and individual therapeutic layers for each person. These two distinct layers can share information between each other, e.g., therapy layer shares its data so that the shared virtual environment layer can change or react to the user's therapeutic response. Two or more persons can coordinate together to perform a joint task within the shared virtual environment, but with each person having a distinct therapeutic treatment. For example, two persons are placed into a shared virtual environment where their joint goal is to defend the moon against an alien invasion and are each given a virtual cannon that they can use to combat the alien forces. In this example, the first person may have a therapeutic layer that tracks their heart rate as they use an exercise machine, and if they maintain their heart rate at or above a level determined by an therapist, then the virtual cannon will fire and the first person can assist in the joint task of defending the moon while performing therapy tailored to their physical and cognitive needs. The second person may have a therapeutic layer that performs brainwave entrainment by displaying aliens flashing at certain frequencies to induce gamma waves in the second persons brain, and if they maintain focus (determined by eye tracking sensors in a display device) on the flashing alien for a predetermined time period (e.g., 10 seconds, 30 seconds, etc.) as set by a therapist, then the virtual cannon will fire at the flashing alien. In this example, the first person would not see any blinking aliens, as that is distinct to the second person's therapeutic layer.

Extended reality therapy system can provide more targeted cognitive therapy using extended reality elements that go beyond what is readily possible in the physical world. A shared virtual environment can manipulate the environment to increase brain functions such as recognition, memory, cognition, recall, emotion response, and motor skills. For example, virtual reality technology allows for the creation of Escher environments, impossible colors, and spatial distortions to stimulate reflexes, spatial awareness, perception of object permanence, navigation, etc. The ability to use virtual reality simulations with targeted cognitive regimens implemented as games and virtual activities and to also monitor and capture the results of such regimens can produce useful and relevant data for researchers and data scientists to study. Additionally, such data capturing capabilities can be used in conjunction with machine and/or deep learning techniques to improve both VR engine and therapeutic engine capabilities such as, but not limited to, improved environmental modeling, and improved cognitive therapy regime design.

As lifespans have improved in the past few decades, particularly in more developed countries, the mean and median age of populations have increased. The greatest risk factor for neurodegenerative diseases is aging, so older persons are more likely to suffer from degenerative diseases and conditions affecting the nervous system such as amyotrophic lateral sclerosis, Parkinson's disease, Alzheimer's disease, fatal familial insomnia, Huntington's disease, Friedreich's ataxia, Lewy body disease, and spinal muscular atrophy. It has been estimated that some 20-40% of healthy people between 60- and 78-years old experience discernable decrements in cognitive performance in one or more areas including working, spatial, and episodic memory, and cognitive speed. Early stages of neurodegenerative diseases are difficult to detect, the causes of such diseases are not well understood, and treatments for such diseases are non-existent.

Without using one of the costly brain scan technologies, it remains difficult to detect, assess, and treat poor functioning of the nervous system, whether such poor functioning is due to injury to the brain, neurodegenerative disease, psychological or physical trauma, or changes in brain chemistry, diet, stress, substance abuse, or other factors. For certain neurological conditions, such as Chronic Traumatic Encephalopathy (CTE), none of the current brain scan technologies are able to reliably capture diagnostic data. Other neurological deficits and conditions can be evaluated or diagnosed using assessments using readily available equipment and observational analysis, such as the Cognitive Performance Test (CPT) and Timed Up and Go Test (TUG) but lack the sensitivity suitable for nuanced or early deficit detection. Each of these types of poor nervous system function can impact different parts of the brain and/or nervous system in different ways. Due to the complexity of interactions in the nervous system and the brain's ability to adapt its function in many areas, it remains difficult to detect poor functioning and to identify which neurological functions states and anatomical aspects and regions are impacted early enough to implement an effective treatment protocol.

However, recent research studies have demonstrated that physical activity, especially aerobic exercise, can improve neurogenesis and other neurological functions and states, whether related to physical brain and nervous system impairments or mental health/emotional issues. In addition, evolutionary biologists have hypothesized that early humans began their cognitive revolution when they ventured into the African savannah and started walking upright. In fact, more recent research studies on the cerebellum, an ancient part of the brain that coordinates the motor control, have discovered unexpected connections between the cerebellum and other parts of the brain. Specifically, according to a team of researchers from the University of Washington, only 20 percent of the cerebellum connections was dedicated to areas involved in physical motion, while 80 percent was connected to areas involved in functions and states such as abstract thinking, planning, emotion, memory and language. The cerebellum doesn't actually execute tasks like thinking, just as it doesn't directly control movement. Instead, it monitors and coordinates the brain areas that are doing the work and makes them perform better.

Therefore, simultaneous testing of primary physical tasks such as walking or running and the associative activities that include various mental, other physical activities as well as emotional experiences (commonly known as a dual task assessment), and the correlation of results therefrom can be used to evaluate specific neurological functional areas to create a profile of relative neurological functioning and see where deficiencies may be present. Therefore, changes in a person's walking gait while the person is engaged in other associative activities like solving a logic puzzle could be analyzed and compared against the normal or average dual-tasking costs of the same population group for relative functioning as well as anomalies. Such anomalies for the given brain functions and states or regions could be indicative of abnormal central nervous system functions. Further, the combination of the dual-tasked physical and associative activities can help identify the abnormally-performing neurological functions or even help isolate affected neurological regions. For example, a walking gait/logic puzzle dual-task activity may indicate normal functioning in a given individual, indicating that autonomous physical activity and cognition are not affected. However, in the same individual another dual task of walking and listening within a virtual reality (VR) environment may result in gait changes or a complete stop of the walk as the neurological functions required for these tasks are different from walking and logic. In this case, it may indicate that there may be injury to or degeneration of the auditory cortex of the temporal lobe, potentially informing further diagnostic procedures. As a result, a system combining numerous combinations of various dual-tasking activities, covering all neurological functions or regions, may be able to evaluate, detect, and treat neurological deficits and conditions even before they become noticeably symptomatic. For individuals for whom symptoms are already present, such a system can evaluate and track changes over time, and potentially slow down or reverse the progression of such deficits and conditions.

Using this same dual-tasking analysis, it is also possible to evaluate, detect, and treat neurological conditions and changes involving mental health and emotional issues. For example, elevated heart rate, elevated blood pressure, or chest pain during exercise that are higher than an individual's normal history for these indicators can indicate emotional stress. The addition of story-telling or emotional experiences through computer games and/or simulations (and especially when such experiences are virtual-reality experiences) can help to elicit emotional and physiological responses or lack thereof. For example, a veteran suffering from PTSD (Post-Traumatic Stress Disorder) could be trained inside such a dual-tasking VR environment so that s/he can gradually regain her/his agency by overcoming progressively challenging physical and emotional scenarios—reactivating her/his dorsolateral prefrontal cortex and lateral nucleus of thalamus with the help of these combined physical and emotional activities (likely using parallel but not war-based scenarios). As a result, the veteran could potentially extricate herself or himself from such traumatic experiences by developing her/his closure stories.

The integration of a primary physical task with an associative activity is also especially well-suited for the evaluation and conditioning of specific aspects of neurological functioning in individuals training for physical, mental, or combined forms of competition. After an initial array of primary physical challenges and associated tasks designed to evaluate specific neurological functioning areas to create a profile of relative functioning a more thorough understanding of the competitor's strengths and weaknesses in their specific mode of competition can be achieved. With the help of a conditioning recommendation algorithm, expert input, and competitor input a regimen of physical and associative tasks specifically suited to improve performance of that competitor and mode of competition can be administered at prescribed or chosen frequency. Digital challenges can further be customized for competition and competitor specificity as the conditioning recommendation algorithm analyzes the efficacy of conditioning regimens for users aiming to improve in similar neurological functions and states, the specific user's response to conditioning inputs over time, and expert recommendations for users with similar neurological functioning profiles and objectives.

Further, as the dual-tasking methodologies described above stimulate activity in certain portions of the brain corresponding to certain neurological functions and states, those same dual-tasking methodologies can be used to apply targeted brainwave entrainment to the brain. After a neurological assessment has been made (whether or not through dual-tasking analysis), a treatment regimen can be selected for treatment of certain areas of the brain and/or specific neurological functions in which dual-task activities are selected which activate (i.e., stimulate) those areas of the brain and/or neurological functions, and brainwave entrainment is applied while those areas of the brain and/or neurological functions and states are activated, thus concentrating the effect of the brainwave entrainment on the activated (i.e., stimulated) areas or neurological functions. The targeted brainwave entrainment therapy may be further enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Implementations of visual brainwave entrainment to date have been limited to passive visual stimulation using physical lights (typically light emitting diodes, or LEDs). There is no interactivity or active engagement with the visual stimulation transducers, which makes the process less effective and uninteresting. Further, the visual stimulation transducers, being physical objects, cannot be changed in terms of size or shape, cannot be modified in reaction to user feedback, and are limited in terms of colors available, are generally fixed in place, and additional lights cannot be added to the system without physically connecting (and likely programming) additional lights.

Virtual objects, on the other hand, have none of these limitations, and can be used as visual stimulation transducers while users are engaged with an on-screen display. Brainwave entrainment using virtual objects provides essentially unlimited variability in terms of stimulator sizes, shapes, colors, movements, rotations, etc., and allows for the use of multiple stimulators simultaneously, each with different characteristics. Any change to a virtual object that is perceptible to a user and can be applied at a repeating frequency may be used to apply brainwave entrainment.

Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the game, stimulation can be applied based on where the user's attention is focused. Attention-based stimulation provides opportunities for both direct stimulation (e.g., flashing an object at which the user is looking, playing sounds or providing haptic feedback associated with a game object or activity that is the object of the user's attention, etc.) and indirect stimulation (e.g., flashing an object in the user's periphery of vision, playing sounds or providing haptic feedback associated with the game, but not the object of the user's attention such as a background element, background music or sounds, etc.). For example, eye tracking technology can be used to determine where the user is looking on the screen at any given time, and objects at which the user is looking can be used to provide visual stimulation even if the user changes his or her attention to a different object on the screen. The user's attention to objects on the screen can be monitored over time to determine whether the user is remaining focused on the activity, or is getting tired and losing focus, and the determined level of user attention can be used to change the type, intensity, directness, and other characteristics of the stimulation. Other means of determining the user's attention may be used such as assuming that the user's attention is focused on an object with which the user has just interacted.

Brainwave entrainment using virtual objects may be further enhanced by using multiple objects, each capable of providing complementary types of stimulation, and/or by intentionally directing the user's attention to objects providing certain types of stimulation. For example, if the user is playing a first-person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Brainwaves are frequencies at which electrical impulses in the brain occur. Brainwave frequencies change based on the state of consciousness of the user (e.g., sleeping, awake, dreaming, concentrating, relaxed, contemplative, meditative, irritated, etc.). Generally speaking, brainwaves are divided into five categories with frequencies roughly in the following ranges.

Delta waves are brainwaves in the general frequency range of 0.1 Hz to 4 Hz. Delta waves occur during deep sleep and indicate a low level of arousal. Theta waves are brainwaves in the general frequency range of 4 Hz to 8 Hz. Theta waves occur in a state between wakefulness and sleep, such as during daydreaming and meditation, and can indicate drowsiness, creativity, or imagination. Alpha waves are brainwaves in the general frequency range of 8 Hz to 12 Hz. Alpha waves occur during a waking state, but are associated with relaxation, problem solving, analysis, and decision-making. Beta waves are brainwaves in the general frequency range of 12 Hz to 30 Hz. Beta waves occur during alertness, concentration, and strenuous mental activities such as solving mathematical problems and planning for the future. Gamma waves are brainwaves in the general frequency range of 30 Hz to 44 Hz. Gamma waves are associated with high-level information processing. There is evidence of Lambda brainwaves in a range around 47 Hz to 70 Hz, and other brainwave entrainment frequencies may be useful up to around 100 Hz. These ranges are approximate, and there is some overlap between them.

There are many promising uses of brainwave entrainment. One promising use of brainwave entrainment is to treat and/or prevent epilepsy. There is some evidence that epileptic seizures occur when the brain falls into theta wave activity (approximately 4 Hz to 8 Hz) during normal waking consciousness. Normal waking consciousness is typically associated with beta wave brain activity (12 Hz to 38 Hz).

Performing brainwave entrainment at beta wave frequencies on persons with epilepsy may help prevent them from falling into theta wave brain activity, thus preventing seizures.

Another possible use for brainwave entrainment is to reduce agitation by performing brainwave entrainment at alpha wave frequencies (approximately 8 Hz to 12 Hz). Alpha wave frequencies are those brain wave frequencies between theta wave activity (typically associated with dreaming) and beat wave activity (typically associated with concentration and learning). Alpha wave frequencies are associated with relaxation and calmness. Therefore, brainwave entrainment at alpha wave frequencies may help induce relaxation and calmness.

Many different wave forms and/or pulse widths may be used in delivering entrainment at the selected frequency or frequencies, regardless of the modality (light, sound, etc.) of the stimulation. Wave forms may include, but are not limited to, rectangular wave forms, sine wave forms, triangular wave forms, and sawtooth wave forms. Pulse widths or duty cycles at any given frequency may be varied across the entire range of the frequency period. For example, at a given frequency, the duty cycle of each period of the frequency can be varied from nearly 0% on-time/100% off-time to nearly 100% on-time/0% off-time. Thus, for a given frequency, the stimulator (e.g., light) can be on and off for an equal amount of time in each period (a 50% duty cycle), mostly on during each period (e.g., a 75% duty cycle), or mostly off during each period (e.g., a 25% duty cycle). In these cases, the frequency of the stimulation is the same, but the amount of on-time of the stimulation in each period of the frequency is different.

Different pulse widths or duty cycles may be useful, depending on the circumstances. For example, when engaged in a mental task that requires visual acuity, a very low or very high duty cycle may be used to flash a light stimulator at a pulse width that can be captured by the human eye but is not consciously recognizable. The human eye can capture flashes of light as short as $1/200^{th}$ of a second (equivalent to a frequency of 200 Hz), possibly shorter, but because of persistence of vision, cannot distinguish between repeated flashes of light at that frequency. Television and computer monitor frame refresh rates are typically 60 Hz or above, as this is a frequency at which persistence of vision makes it difficult to distinguish between frames. Thus, for example, the flicker of light stimulation at a frequency of 40 Hz and a 50% duty cycle would be easily perceivable by most human beings as each "on" pulse is $1/80^{th}$ of a second long and separated by another "off" time of another $1/80^{th}$ of a second. However, the flicker of light stimulation at the same frequency, but at an 80% duty cycle would likely not be consciously perceptible, as the "on" time of each period would last about $1/50^{th}$ of a second and the "off" time of each period would last about $1/200^{th}$ of a second. Thus, the "off" time of each period is within the limits of capture by the human eye (200 Hz) but would likely not be consciously perceptible because it is above the average frequency resolution (60 Hz) of the human eye, and the light would appear to the conscious mind to be on all the time.

In a similar manner, pulse widths or duty cycles may be adjusted to be perceptible to certain cells in the eye but not others. The human eye has two different types of light receptors: cones and rods. Cones are the dominant light receptors used under daylight conditions, and reception of light by cones is called photopic vision. Cones are able to distinguish colors but are less sensitive to lower light intensity and the persistence of vision of cones is greater (meaning that the frequency of pulses that can be distinguished by cones is less than for rods). Rods are the dominant light receptors used at night and under low-light conditions, and reception of light by rods is called scotopic vision. Rods are not able to distinguish colors but are more sensitive to lower light intensity and the persistence of vision of rods is less (meaning that the frequency of pulses that can be distinguished by rods is greater than for cones). Cones are greatly concentrated in the center of vision (where the person is directly looking) while rods are considerably more dominant in the periphery of vision. This difference in the type of light receptors in the eye can be used to advantage when selecting either a frequency of stimulation or a pulse width/duty cycle of that frequency. Again using the example above where visual acuity is required for a mental task, the pulse width or duty cycle of each period of a brainwave entrainment frequency of light can be selected to be perceptible to rods but not to cones, thus allowing the brainwave entrainment frequency of light to be perceived by the brain (through the rods in the periphery of vision which have a greater frequency resolution), but not consciously perceptible to the person (who is primarily focused on the light received by the cones (in the center of vision and with a lesser frequency resolution). One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Definitions

The term "amplitude" means the difference between the high or low state of a signal or wave form and the base state of that signal or wave form in a full period (high/low or on/off cycle) of the frequency of the signal or wave form.

The phrase "associative activity" as used herein means a second task or activity to be engaged in by an individual under assessment. The associative activity will often, but not always, be a mental or cognitive task such as performing arithmetic or identifying objects on a display.

The term "biometrics" as used herein mean data that can be input, directly measured, or computed using directly measured data from a user. This data includes but is not limited to physical and virtual movement, physiological, biological, behavioral, navigational, cognitive, alertness and attention, emotional, and brainwave measurements and patterns.

The phrase "brainwave entrainment" means application of a stimulus with a frequency from about 0.5 Hz to about 100 Hz as a means of neurological therapy. The stimulus may be of any perceptible form such as, but not limited to, light, sound, vibration, or electrical stimulation. The stimulus need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus).

The phrase "composite function score" as used herein means an indicative of a relative level of neurological functioning comprised of weighted input of combined movement, biometric, and performance data sources collected by a given embodiment of the system, input by the user or an expert, historical performance and life history data from various sources, etc.

The term "conditioning" as used herein means all aspects of the system that can be used for the improvement, training, treatment of or exposure to aspects of neurological functioning. This could be in the form of a prescribed regimen from an expert, recommendation algorithm, self-selected experiences, or combination thereof.

The phrase "dual task assessment" as used herein means measurement of baseline performance on a set of tasks and/or activities performed individually, as well as performance of the same set of tasks and/or activities simultaneously. While this is typically a single primary task (usually motor) combined with a single associative activity (typically a neurological activity such as cognitive task), it should be taken herein to include other combinations of multiplexed tasks in combinations including, but not limited to, combinations in excess of two tasks and combinations that target a single or multiple aspects of neurological functioning.

The phrase "dual task cost" as used herein means any method for quantifying the difference in performance of a dual task assessment between the set of tasks performed individually and the same set of tasks performed simultaneously. Typically includes a comparison of each task performed in isolation to the performance on each of those tasks when performed simultaneously, either for a pair or larger combination of tasks.

The phrase "dual task stimulation" as used herein means the assignment of a single primary task (usually motor) combined with a single associative activity (typically a neurological activity such as cognitive task) for a user to perform, whereby the combination of the task and activity either stimulates neurological activity in certain areas of the brain, or which is associated with certain neurological functions, or both. It is not necessary that the precise areas of the brain associated with the neurological function are known, only that certain tasks and activities are associated with that neurological function. This phrase should be taken herein to include other combinations of multiplexed tasks in combinations including, but not limited to, combinations in excess of two tasks and combinations that target a single or multiple aspects of neurological functioning.

The phrase "duty cycle" means the amount of time that a frequency signal is in the "high" or "on" state, expressed as a percentage, wherein each full period (complete high/low cycle) of the frequency signal represents 100%. Note that "duty cycle" and "pulse width" are two different means of expressing the same concept.

The term "expert" as used herein means an individual with specialization in an area via formal training, credentials, or advanced proficiency in a modality of interest to the user or with regard to neurological functioning. This includes but is not limited to physicians, psychiatrists, physical therapists, coaches, fitness trainers, high level athletes or competitors, and teachers.

The term "frequency" means a signal or wave form having a periodic repetition of high/low or on/off states. Examples of signals and wave forms that exhibit the characteristic of frequency include, but are not limited to, rectangular wave forms, sine wave forms, triangular wave forms, and sawtooth wave forms.

The terms "game" or "game application" mean any computer game, puzzle, display, animation, or simulation comprising virtual objects that can be interacted with in some manner by a person. These phrases include, but are not limited to, traditional two-dimensional games and puzzles, three-dimensional virtual reality (VR) applications and environments, enhanced reality and augmented reality applications and environments (comprising both real-world elements and virtual elements, such as virtual objects superimposed on a video feed of the real environment surrounding the user), and interactive applications that allow one to sense virtual objects through haptic feedback (whether or not associated with a visual display of the objects).

The term "gamification" as used herein means the application of brainwave entrainment using a game or a game application.

The phrases "neurological functioning" and "neurological function" as used herein mean any and all aspects of neuroscience and neurology where input, output, processing, or combination thereof involve aspects of the nervous system. These include but are not limited to functional as well as anatomical aspects of cognitive, sensory, motor, emotional, and behavioral functions and experiences.

The phrase "neurological state" as used herein means a state of the neurological system including, but not limited to cognitive states, emotional states, and brain physiology status (electrical activity, blood flow, etc.).

The phrase "primary task" as used herein means a first task or activity to be engaged in by an individual under assessment. The primary task will often, but not always, be a physical task or exercise such as walking on a treadmill.

The phrase "pulse width" means the amount of time that a frequency signal is in the "high" or "on" state, expressed as a time period that is a portion of each full period (complete high/low cycle) of the frequency signal. Note that "duty cycle" and "pulse width" are two different means of expressing the same concept. The phrase "pulse width modulation" is often used to denote changing of the pulse width of a frequency signal.

The term "transducer" as used herein means a device that converts an electrical signal into variations in a physical quantity, such as sound, light, pressure, or electrical stimulation. A display is included in the definition of "transducer."

The phrase "stimulation transducer" as used herein means a transducer used to stimulate one of the senses of a person or animal. Any portion of a display may be used as a stimulation transducer, non-limiting examples of which include virtual objects or backgrounds on the display.

The phrase "virtual object" means a computer-generated simulation of an object perceivable to a human being. Virtual objects include, but are not limited to, visible virtual objects such as two-dimensional and three-dimensional shapes shown on a display, non-visible virtual objects such as those that might be "felt" through haptic feedback (e.g., gloves equipped with haptic feedback equipment that provide resistance to the user's fingers around the contours of a virtual object in space), and any combination of the two (e.g., a visible virtual object displayed in a virtual reality environment through a VR headset which can also be "felt" by the user via haptic feedback). A virtual object does not have to be gamified and may be, for example, a virtual object displayed on a screen.

The phrase "virtual reality" means a computer-generated environment in which a person may participate as an actor in the environment via an avatar representing the person in the computer-generated environment. The phrase "virtual reality" includes all forms of such environments including where the entire environment is computer-generated and where the computer generated environment includes real-world elements, often referred to as "extended reality," or "augmented reality." The phrase "virtual reality" does not require the use of a virtual reality headset.

Conceptual Architecture

Figure 1:
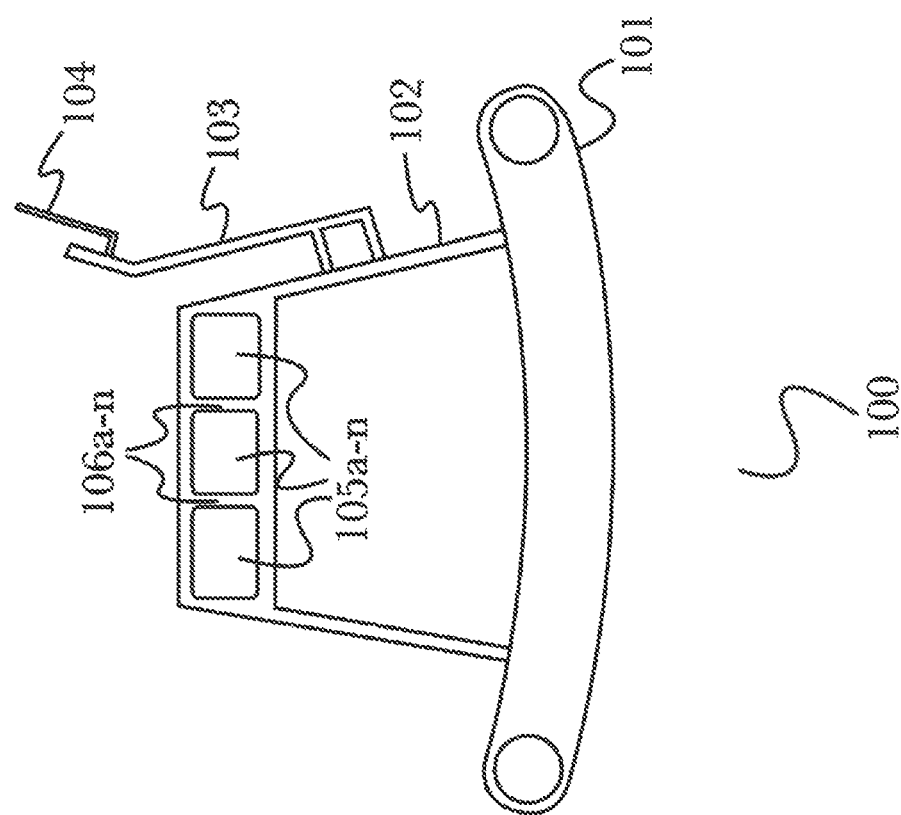
FIG. 1 is a side view of an exemplary variable-resistance exercise machine with an embedded or a wireless computing device controlling the interactive software applications of the invention.

FIG. 1 is a side view of a variable-resistance exercise machine with wireless communication for smart device control and interactive software applications 100 of the invention. According to the embodiment, an exercise machine 100 may have a stable base 101 to provide a platform for a user to safely stand or move about upon. Additional safety may be provided through the use of a plurality of integrally-formed or detachable side rails 102, for example having safety rails on the left and right sides (with respect to a user's point of view) of exercise machine 100 to provide a stable surface for a user to grasp as needed. Additionally, side rails 102 may comprise a plurality of open regions 105a-n formed to provide additional locations for a user to grasp or for the attachment of additional equipment such as a user's smart device (not shown) through the use of a mountable or clamping case or mount. Formed or removable supports 106a-n may be used for additional grip or mounting locations, for example to affix a plurality of tethers (not shown) for use in interaction with software applications while a user is using exercise machine 100 (as described below, referring to FIG. 3).

Exercise machine 100 may further comprise a rigid handlebar 103 affixed or integrally-formed on one end of exercise machine 100, for a user to hold onto while facing forward during use. Handlebar 103 may further comprise a stand or mount 104 for a user's smart device such as (for example) a smartphone or tablet computer, so they may safely support and stow the device during use while keeping it readily accessible for interaction (for example, to configure or interact with a software application they are using, or to select different applications, or to control media playback during use, or other various uses). Handlebar 103 may be used to provide a stable handle for a user to hold onto during use for safety or stability, as well as providing a rigid point for the user to "push off" during use as needed, for example to begin using a moving treadmill surface (described below in FIG. 2). During use, a user may also face away from handlebar 103, using exercise machine 100 in the reverse without their view or range of motion being obscured or obstructed by handlebar 103 (for example, for use with a virtual reality game that requires a wide degree of movement from the user's hands for interaction).

As illustrated, the base 101 of exercise machine 100 may be formed with a mild, symmetrical curvature, to better approximate the natural range of movement of a user's body during use. Common exercise machines such as treadmills generally employ a flat surface, which can be uncomfortably during prolonged or vigorous use, and may cause complications with multi-directional movement or interaction while a user's view is obscured, as with a headset (described below in FIG. 3). By incorporating a gradual curvature, a user's movements may feel more natural and require less reorientation or accommodation to become fluid and proficient, and stress to the body may be reduced.

Figure 3:
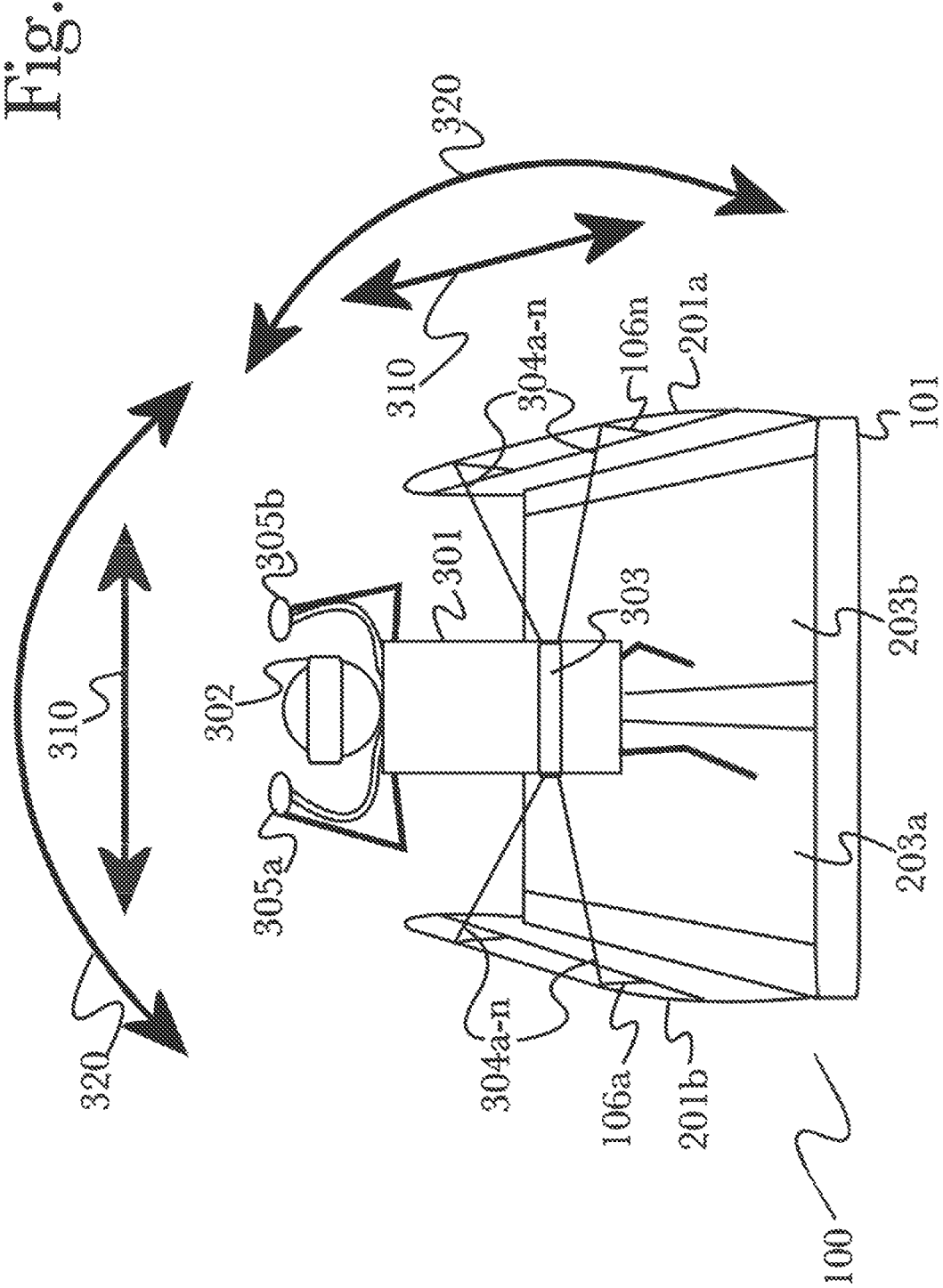
FIG. 3 is a diagram illustrating an exemplary system for a virtual reality or mixed reality enhanced exercise machine, illustrating the use of a plurality of connected smart devices and tethers, and showing interaction via the user's body as a control stick.

FIG. 3 is a diagram illustrating an exemplary system for a virtual reality or mixed reality enhanced exercise machine 100 with wireless communication for smart device control and interactive software applications using a smart device, illustrating the use of a plurality of connected smart devices and tethers, and showing interaction via the user's body as a control stick. According to the embodiment, a user 301 may be standing, walking, or running on a variable-resistance exercise machine 100 with wireless communication for smart device control and virtual reality applications with a stable base 101 and two separate moveable surfaces 203a, 203b for separate movement of the user's legs. Exercise machine 100 may have fixed handlebars with affixed or integrally-formed controllers 305a, 305b for use as connected smart devices for interaction, and support rails 201a, 201b for a user to hold onto or affix tethers for safety or interaction when needed. User 401 may interact with software applications using a variety of means, including manual interaction via controller devices 305a, 305b that may be held in the hand for example to use as motion-input control devices or (as illustrated) may be affixed or integrally-formed into exercise machine 100. This may provide a user with traditional means of interacting with software applications while using exercise machine 100. Additionally, a user's body position or movement may be tracked and used as input, for example via a plurality of tethers 304a-n affixed to handlebars 201a, 201b and a belt, harness or saddle 303 worn by user 301, or using a headset device 302 that may track the position or movement of a user's head as well as provide video (and optionally audio) output to the user, such as a virtual reality headset that displays images while blocking the user's view of the outside world, or an augmented reality or mixed reality headset that combines presented information with the user's view using transparent or semitransparent displays (for example, using transparent OLED displays, hologram displays, projected displays, or other various forms of overlaying a display within a user's normal field of vision without obstructing the user's view). Body tracking may be used to recognize additional input data from user 301 (in addition to manual input via controllers 305a, 305b), by tracking the position and movement of user 301 during use. For example, motion tracking within a headset device 302 may be used to recognize a variety of translational 310 or rotational 320 movement of user's 301 head, such as leaning to the side, or looking over the shoulder. Tethers 304a-n may recognize a variety of movement of user's 301 torso, such as leaning, crouching, side-stepping, or other body movement. This body tracking may then be utilized either as feedback to rehab programs (for example, to track a user's posture for physical therapy coaching or exercises such as holding yoga poses) or input similar to a control stick or joystick in manual controller arrangements, for example by interpreting the user's entire body as the "stick" and processing their body movements as if they were stick movements done manually (such as to control in-game character posture or movement, or to direct movement in certain applications such as vehicle simulations that may turn or accelerate in response to stick movements).

For example, a user 301 on exercise machine 100 may be playing a virtual reality skiing game or rehab program wherein they are given audio and video output via a headset 302 to immerse them in a virtual ski resort. When user 301 is not skiing, they may be able to use manual controls 305a, 305b for such operations as selecting from an on-screen menu or typing text input such as to input their name or to chat with other players using text. When they begin skiing within the game, user 301 may be instructed in proper ski posture or technique and may then use their body to control various aspects of their virtual skiing, such as leaning to the side 320 to alter their course and avoid trees or other skiers, or jumping 310 to clear rocks or gaps. Movement of their head may be detected by a headset 302 and used to control their view independently of their body as it is tracked by tethers 304a-n, allowing user 301 to look around freely without interfering with their other controls. In this manner, the user's entire body may serve as an input control device for the game, allowing and encouraging them to use natural body movements to control their gameplay in an immersive manner while still retaining the option to use more familiar manual control means as needed. Alternatively, specific body functions such as hip twisting are used as user feedback for rehabilitating programs, including rehab games.

Figure 12:
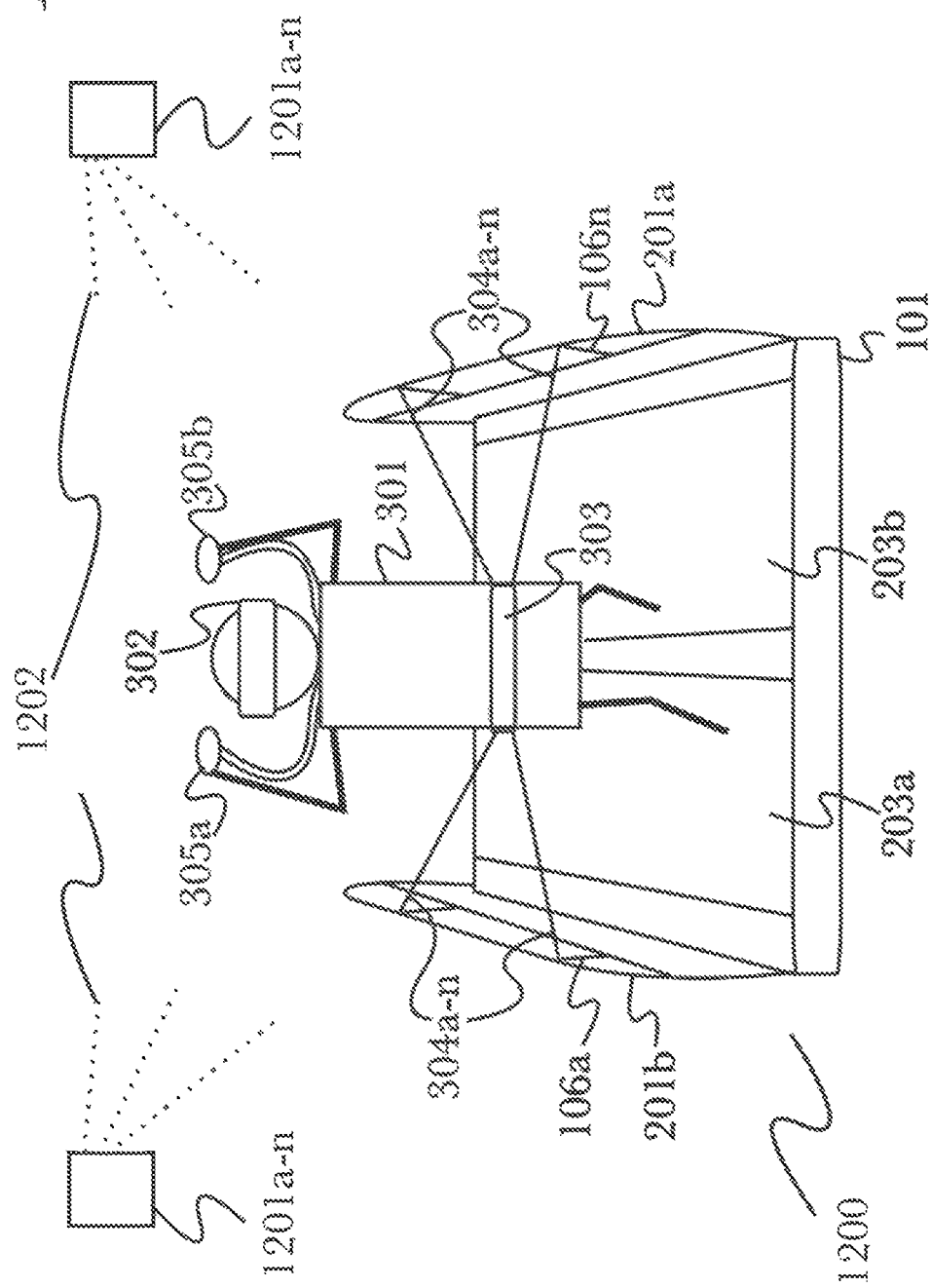
FIG. 12 is a diagram illustrating an exemplary virtual reality or mixed reality enhanced exercise machine, illustrating the use of a plurality of optical sensors to detect body movement of a user during use of an exercise machine.

FIG. 12 is a diagram illustrating an exemplary system 1200 for a virtual reality or mixed reality enhanced exercise machine 100, illustrating the use of a plurality of optical sensors to detect body movement of a user during use of an exercise machine. As above (with reference to FIG. 3), a user 301 may be standing, walking or running, sitting, or otherwise physically active during use of an exercise machine 100. During use, the user's position, posture, movement, cadence, technique, or any other movement or position-related information may be detected, observed, or measured using a plurality of body movement sensors such as (for example, including but not limited to) tethers 304a-n that may optionally be affixed to handlebars 201a-b or other features of an exercise machine 100, hardware sensors integrated into controllers 305a-b or a headset 302 the user may be using during exercise for virtual reality or mixed reality applications, or using a plurality of optical sensors 1201a-n that may be affixed to an exercise machine 100 or adjacent equipment, or that may be affixed to or positioned within an environment around exercise machine 100 to observe the user 301 during use. Optical sensors 1201a-n may be used in a variety of configurations or arrangements, such as using a single wide-angle sensor positioned to observe a user's movement or posture from a particular angle (which may be useful for coaching or physical therapy applications) or using more than one sensor placed about a user to observe their movement in three-dimensional space. A variety of hardware may be utilized in optical sensors 1201a-n, for example including (but not limited to) an infrared or other optical camera that may directly observe the user's movement, a structured-light emitter that projects a structured-light grid 1202 or other arrangement onto the user, exercise machine, or environment (and corresponding scanner or receiver that may observe the user's movement through detected changes in the structured-light projection), or a light-field sensor that detects or measures depth to observe a user's movement in three-dimensions. It should also be appreciated that various combination of optical sensors 1201a-n may be utilized to achieve a desired effect, for example using both structured light and a light-field sensor to observe a user's movement in precise detail in three dimensions. Additionally, some or all optical sensors 1201*a-n* utilized in some arrangements may be integrated into a user's headset 302 or an exercise machine 100 to provide "inside-out" tracking where tracking sensors are associated with the user rather than the environment, or they may be external devices as illustrated that may be introduced to enhance an existing exercise machine or environment.

Utilizing an exercise machine 100 in this manner allows for a variety of novel forms of user interaction within virtual reality or mixed reality applications. For example, a user's body movement during exercise may be tracked in three dimensions and along or around various axes to record movement with six degrees of freedom (6 DOF) comprising both translation along, and rotation about, each of three spatial axes. This may be used with torso tracking as described above (referring to FIGS. 3-7) to produce a 6 DOF "torso joystick" virtual device that directs movement or other inputs within a software application. This may be used in a number of ways, for example including but not limited to aiding exercise through interactive coaching (either with a human coach or using software to simulate a coach by providing feedback to detected user movements), providing physical therapy, interacting with games or other applications during exercise, or using exercise combined with software interaction for an immersive virtual reality or mixed reality experience. For example, a user may control movement or expression of a virtual avatar or other user representation within a software application, such as using their own body movements to direct movement of a virtual character. Physical therapy or fitness coaching may utilize detected movements to assist a user with improving their abilities or technique, or to measure progress. Social interaction applications may utilize body movements during exercise, for example a chat or voice call application may utilize body movement as a form of nonverbal expression similar to emoji or other icons. Safety may also be enhanced by controlling the operation of software in response to detected user movements, for example displaying caution information or pausing an application if a user is detected to move outside a configured safety parameter (such as stepping off a running treadmill, for example).

Figure 8:
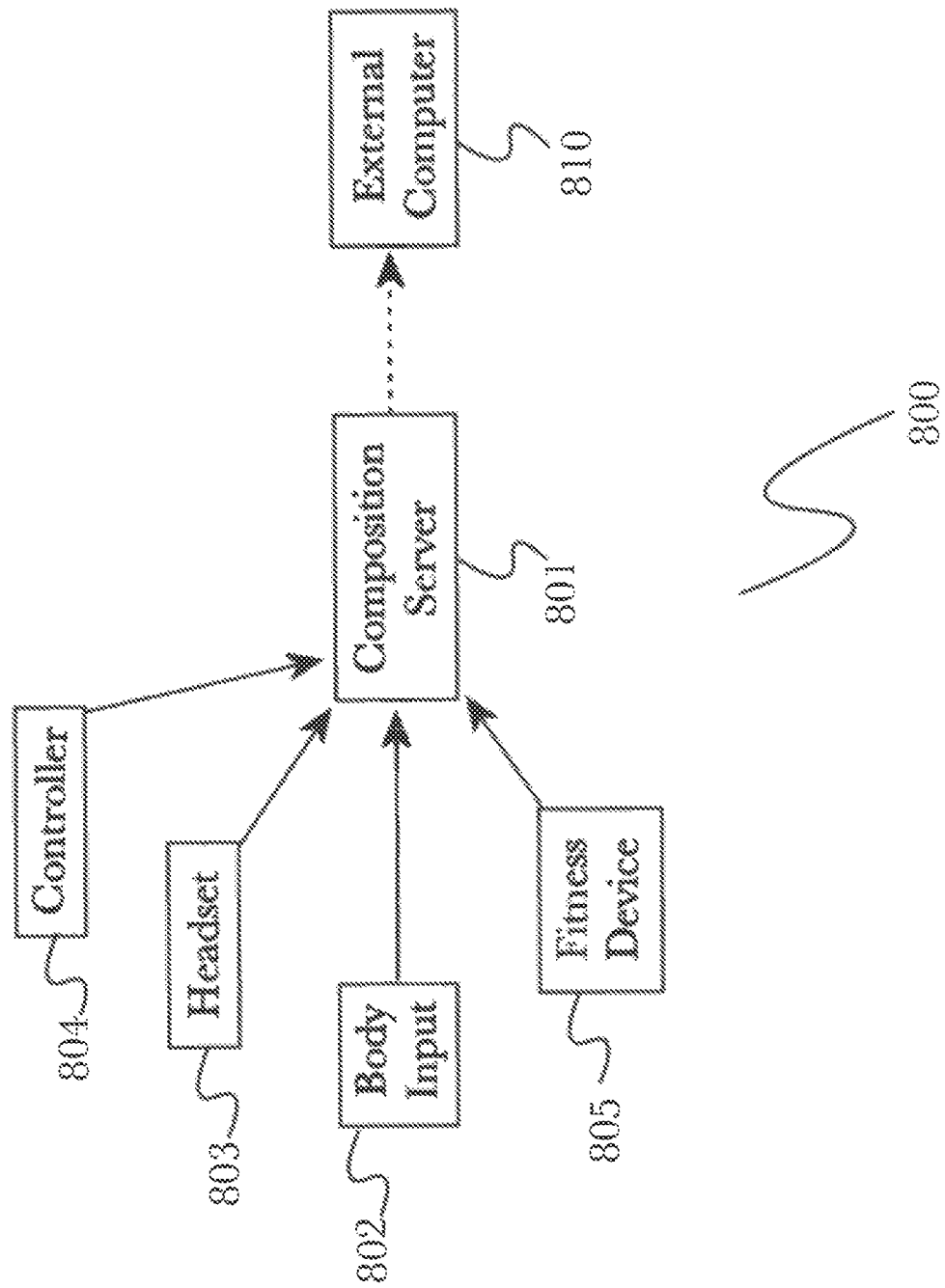
FIG. 8 is a block diagram of an exemplary system architecture for natural body interaction for mixed or virtual reality applications.

FIG. 8 is a block diagram of an exemplary system architecture 800 for natural body interaction for mixed or virtual reality applications of the invention. According to the embodiment, a composition server 801 comprising programming instructions stored in a memory 11 and operating on a processor 12 of a computing device 10 (as described below, with reference to FIG. 13), may be configured to receive a plurality of input data from various connected devices. Such input devices may include (but are not limited to) a variety of hardware controller devices 804 (such as a gaming controller [such as GOJI PLAY™ controllers], motion tracking controller, or traditional computer input devices such as a keyboard or mouse), a headset device 803 such as an augmented reality or mixed or virtual reality headset (for example, OCULUS RIFT™, HTC VIVE™, SAMSUNG GEAR VR™, MICROSOFT MIXED REALITY™, or other headset devices), a variety of fitness devices 805 (for example, fitness tracking wearable devices such as FITBIT™, MICROSOFT BAND™, APPLE WATCH™, or other wearable devices), or a variety of body input 802 tracking devices or arrangements, such as using a plurality of tethers attached to the environment and a harness worn by a user, configured to track movement and position of the user's body.

Various input devices may be connected to composition server 801 interchangeably as desired for a particular arrangement or use case, for example a user may wish to use a controller 804 in each hand and a headset 803 but omit the use of fitness devices 805 altogether. During operation, composition server 801 may identify connected devices and load any stored configuration corresponding to a particular device or device type, for example using preconfigured parameters for use as a default configuration for a new controller or using historical configuration for a headset based on previous configuration or use. For example, a user may be prompted (or may volunteer) to provide configuration data for a particular device, such as by selecting from a list of options (for example, "choose which type of device this is", or "where are you wearing/holding this device", or other multiple-choice type selection), or composition server 801 may employ machine learning to automatically determine or update device configuration as needed. For example, during use, input values may be received that are determined to be "out of bounds", for example an erroneous sensor reading that might indicate that a user has dramatically shifted position in a way that should be impossible (for example, an erroneous reading that appears to indicate the user has moved across the room and back again within a fraction of a second, or has fallen through the floor, or other data anomalies). These data values may be discarded, and configuration updated to reduce the frequency of such errors in the future, increasing the reliability of input data through use.

Composition server 801 may receive a wide variety of input data from various connected devices, and by comparing against configuration data may discard undesirable or erroneous readings as well as analyze received input data to determine more complex or fine-grained measurements. For example, combining input from motion-sensing controllers 804 with a motion-sensing headset 803 may reveal information about how a user is moving their arms relative to their head or face, such as covering their face to shield against a bright light or an attack (within a game, for example), which might otherwise be impossible to determine with any reliability using only the controllers themselves (as it may be observed that a user is raising their hands easily enough, but there is no reference for the position or movement of their head). These derived input values may then be combined into a single composite input data stream for use by various software applications, such as augmented reality or mixed or virtual reality productivity applications (for example, applications that assist a user in performing manual tasks by presenting virtual information overlays onto their field of vision, or by playing audio directions to instruct them while observing their behavior through input devices, or other such applications), or mixed or virtual reality applications or games, such as simulation games that translate a user's movement or position into in-game interaction, for example by moving a user's in-game character or avatar based on their physical movements as received from input devices. In some arrangements, composition server 801 may operate such software applications in a standalone manner, functioning as a computer or gaming console as needed. In other arrangements, composition server 801 may provide the composite data for use by an external computer 810, such as a connected gaming console, mixed or virtual reality device, personal computer, or a server operating via a network in the cloud (such as for online gaming arrangements, for example). In this manner, the composite data functions of the embodiment may be utilized with existing hardware if desired, or may be provided in a standalone package such as for demonstrations or public use, or for convenient setup using a single device to provide the full interaction experience (in a manner similar to a household gaming console, wherein all the functions of computer components may be prepackaged and setup to minimize difficulty for a new user).

It should be appreciated that while reference is made to virtual reality applications, a wide variety of use cases may be possible according to the embodiment. For example, torso tracking may be used for fitness and health applications, to monitor a user's posture or gait while walking, without the use of additional virtual reality equipment or software. In some arrangements, some or all interaction between a user and a software application may be nonvisual, and in some arrangements no display device may be present. In such an arrangement, a user may interact with software entirely using feedback and movement of a worn harness 420 or tethers 304a-n, using resistance or software-guided actuation of tethers 304a-n (as described below, with reference to FIGS. 4-7) or other elements. In other arrangements, various combinations of display devices and other electronic devices may be used for a mixed-reality setup, for example where a user's movement and interaction may be used by software to incorporate elements of the physical world into a digital representation of the user or environment. For example, a user may interact with games or fitness applications, participate in social media such as chat, calls, online discussion boards, social network postings, or other social content, or they may use body tracking to navigate user interface elements of software such as a web browser or media player. Software used in this manner may not need to be specially-configured to utilize body tracking, for example to navigate a web browser a user's body movements or reactions to feedback may be processed by a composition server 801 and mapped to generic inputs such as keystrokes or mouse clicks, for use in any standard software application without the need for special configuration.

It should be further appreciated that while reference is made to a treadmill-type exercise machine 100, such an exercise machine is exemplary and any of a number of exercise machines may be utilized according to the aspects disclosed herein, for example including (but not limited to) a treadmill, a stationary bicycle, an elliptical machine, a rowing machine, or even non-electronic exercise equipment such as a pull-up bar or weight machine. Traditional exercise equipment may be outfitted with additional components to facilitate virtual reality or mixed reality interaction according to the aspects disclosed herein, for example by affixing a plurality of tethers 304a-n to a weight machine so that a user's movement during exercise may be used as interaction as described below (with reference to FIGS. 3-7).

Figure 25:
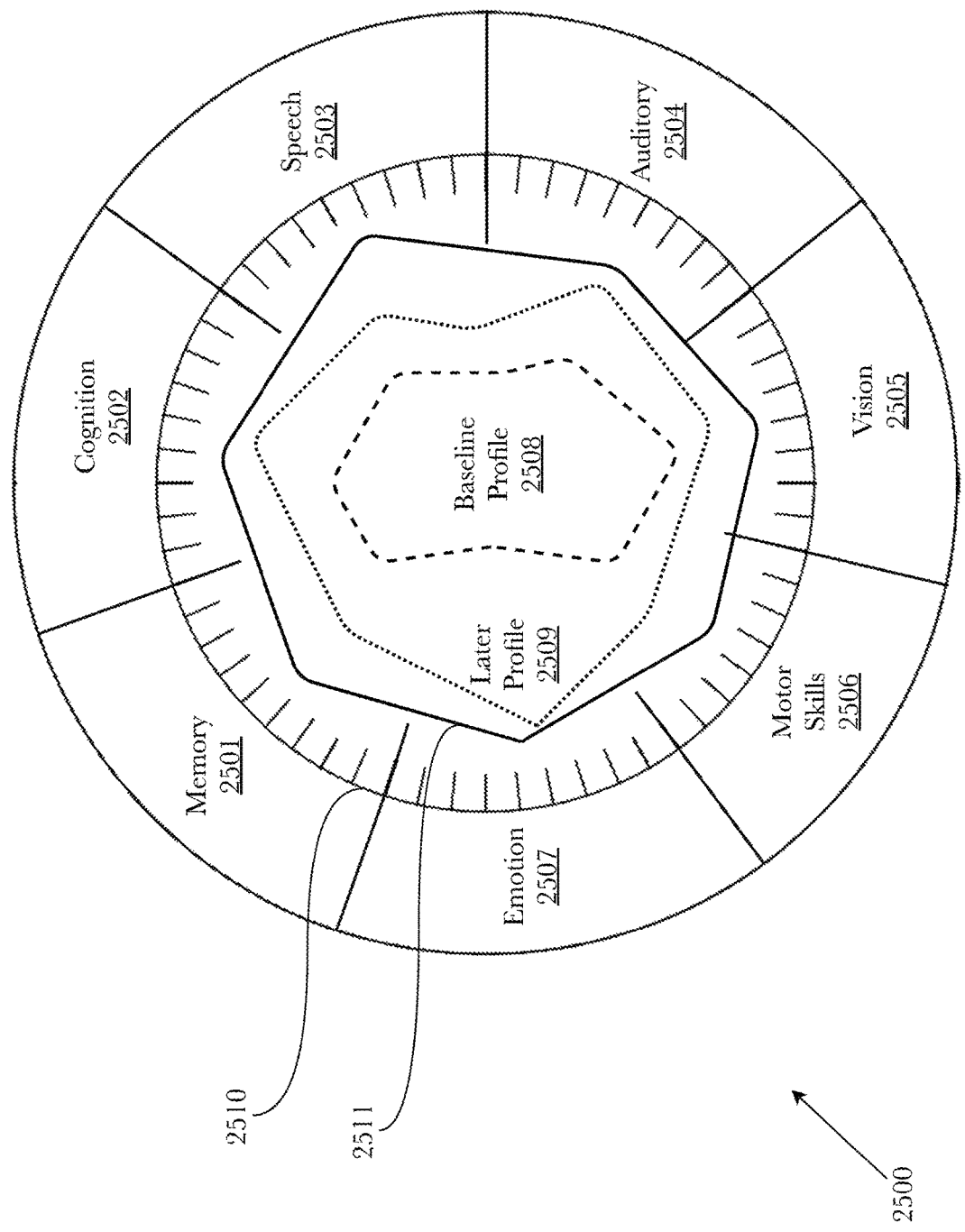
FIG. 25 is a composite functioning score spatial map showing the relative ability of an individual in several physical and mental functional measurement areas.

FIG. 25 is a composite functioning score spatial map 2500 showing the relative ability of a user in several physical and mental functional measurement areas (also referred to herein as "composite functioning scores" or "composite functioning score groups") 2501-2507. The composite functioning score spatial map is a visual representation of a person's ability in several functional measurement areas 2501-2507. The center of the composite functioning score spatial map 2500 represents zero ability, while the inner circle 2510 of the composite functioning score spatial map 2500 represents full ability (i.e., maximum functionality of a healthy individual while not dual-tasking). Greater functionality in a given composite functioning score 2501-2507 is represented by a greater profile coverage area in the direction of that functional measurement area. The average profile area of a representative population of individuals (e.g., of the same age as the individual being tested) is shown as the solid line profile average 2511 of the composite functioning score spatial map 2500. The composite functioning score spatial map 2500 is a visual representation of data obtained from other components of the system and placed into a composite functioning score matrix or other data structure (not shown) which organizes the data relative to the various composite functioning scores.

In this example, there are seven groups of composite functioning scores, each representing either a physical ability, a mental ability, or a combined ability, and all of which together represent a picture of an individual's nervous system function. The memory 2501 and cognition 2502 composite functioning score groups represent purely mental activities, and present a picture of the individual's ability to think clearly. The speech 2503, auditory 2504, and vision 2505 composite functioning score groups represent combined physical/mental activities, as each represents some physical/mental interaction on the part of the individual. For example, speech requires the individual not only to mentally generate words and phrases on a mental level, but also to produce those words and phrases physically using the mouth and vocal cords. It is quite possible, for example, that the individual is able to think of the words, but not produce them, which represents one type of neurological condition. The speech 2503 composite functioning score group represents that combined ability, and the auditory 2504 and vision 2505 composite functioning score groups represent a similar combined ability. The motor skills 2506 composite functioning score group represents a mostly-physical ability to move, balance, touch, hold objects, or engage in other non-cognitive activities (recognizing, of course, that the nervous system controls those movements, but is not engaged in higher-level thinking). The emotional biomarker 2507 group represents the individual's emotional responses to certain stimuli during testing, as would be indicated by lack of empathetic responses to virtual reality characters in a story, responses indicating sadness or depression, etc.

From the data obtained from other components of the system, a profile of an individual's functional ability may be created and displayed on the composite functioning score spatial map. For example, a baseline profile 2508 may be established for an individual during the initial use or uses of the system (e.g., pre-treatment evaluation(s)), showing a certain level of ability for certain composite functioning scores. In the baseline profile 2508 example, all composite functioning scores indicate significant impairment relative to the population average 2511, but the composite functioning scores for cognition 2502 and auditory 2504 ability are relatively stronger than the composite functioning scores for memory 2501, speech 2503, vision 2505, and motor skills 2506, and the emotional biomarker group 2507 indicates substantial impairment relative to the population average 2511. Importantly, changes in the profile can show improvements or regressions in functionality, and changes over time in the profile can be tracked to show trends in improvement or regression. For example, a later profile 2509 for the same individual shows improvement in all biomarker groups, with substantial improvement in the cognition 2502, auditory 2504, motor skill 2506 biomarker groups, and dramatic improvement in the emotion 2507 composite functioning score groups, relative to the baseline profile 2508. The biomarker group for emotion 2507 in the later profile 2509 shows performance matching or nearly matching that of the population average 2511.

Figure 26:
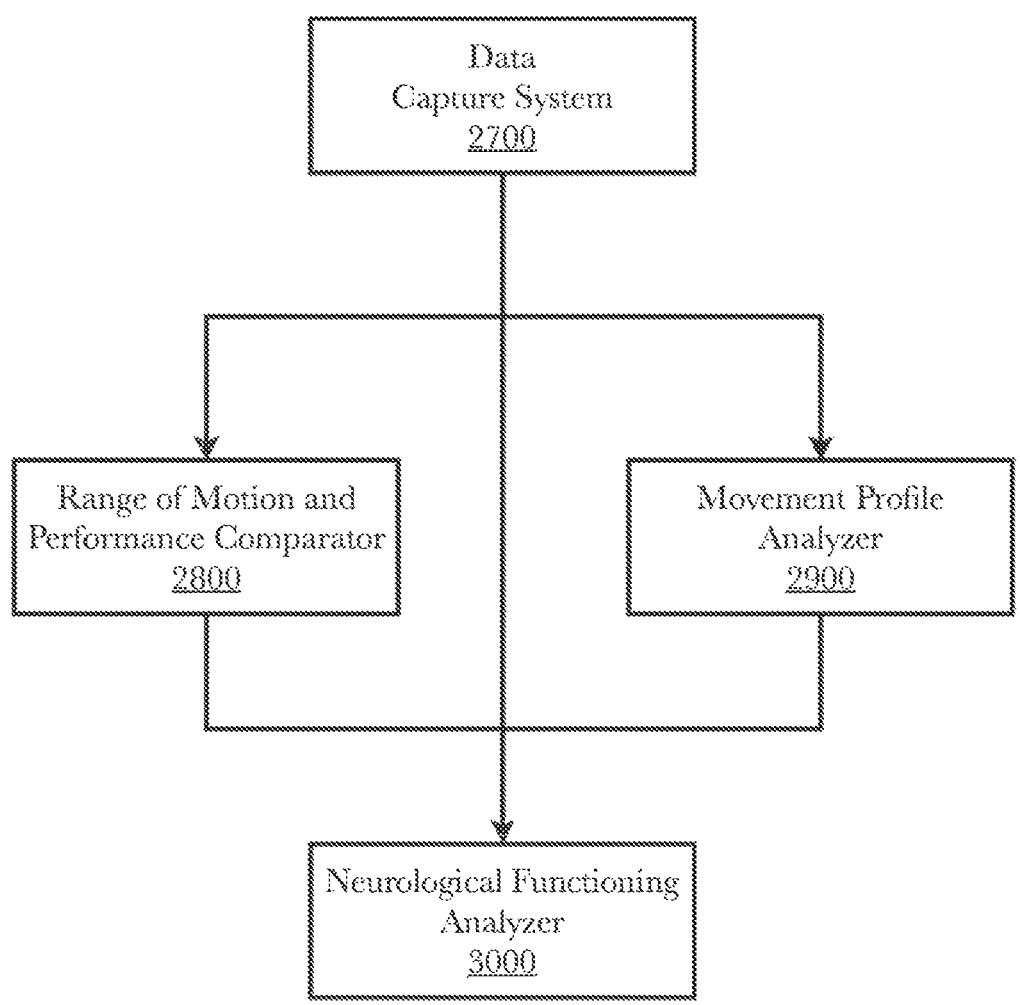
FIG. 26 is an overall system architecture diagram for a neurological functioning analyzer.

FIG. 26 is an overall system architecture diagram for a system for analyzing neurological functioning. In this example, the system comprises a data capture system 2700, a range of motion comparator 2800, a movement profile analyzer 2900, and a neurological functioning analyzer 3000. The data capture system 2700 captures data from sensors on the system such as motor speed sensors, angle sensors, accelerometers, gyroscopes, cameras, and other sensors which provide data about an individual's movement, balance, and strength, as well as information from software systems about tasks being performed by the individual while engaging in exercise. The range of motion comparator 2800 evaluates data from the data capture system 2700 to determine an individual's range of motion relative to the individual's personal history and relative to statistical norms, and to population averages. The movement profile analyzer 2900 evaluates data from the data capture system 2700 to generate a profile of the individual's physical function such as posture, balance, gait symmetry and stability, and consistency and strength of repetitive motion (e.g., walking or running pace and consistency, cycling cadence and consistency, etc.). The neurological functioning analyzer evaluates data from the data capture system 2700, the range of motion comparator 2800, and the movement profile analyzer 2900 to generate a profile of the user's nervous system function as indicated by composite functioning scores which indicate relative ability of an individual in one or more physical and mental functional measurement areas (also referred to herein as "composite functioning scores").

Figure 27:
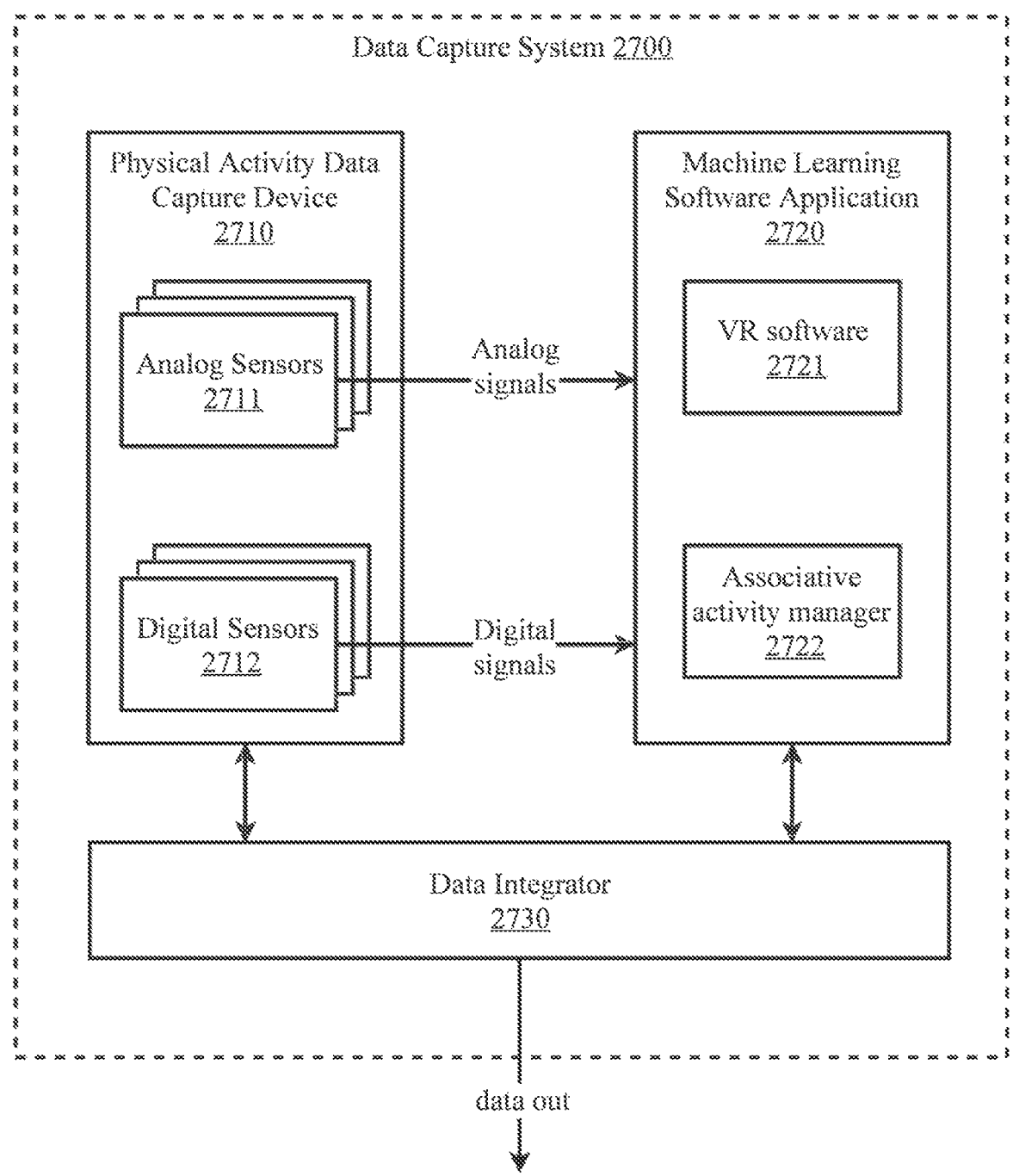
FIG. 27 is a system architecture diagram for the data capture system aspect of a neurological functioning analyzer.

FIG. 27 is a system architecture diagram for the data capture system aspect of a neurological functioning analyzer. In this embodiment, the data capture system 2700 comprises a physical activity data capture device 2710 designed to capture information about an individual's movements while the individual is engaged in a primary physical activity and a software application 2720 designed to assign physical tasks and associative activities, to engage the user in the physical tasks and associative activities, and track and store responses to tasks and activities, as well as a data integrator 2730 configured to convert, calibrate, and integrate data streams from the physical activity data capture device 2710 and software application 2720. The data capture system 2700 captures data from sensors 2711, 2712 on the physical activity data capture device 2710 such as motor speed sensors, angle sensors, accelerometers, gyroscopes, cameras, and other sensors which provide data about the speed, operation, direction and angle of motion of the equipment, and about an individual's movement, balance, and strength.

The physical activity data capture device 2710 may be any type of device that captures data regarding the physical movements and activity of a user. In some embodiments, the physical activity data capture device 2710 may be a stand-alone device not associated with the activity being performed (e.g., a camera, ultrasonic distance sensor, heat sensor, pedometer, or other device not integrated into exercise equipment). In other embodiments, the physical activity data capture device 2710 may be exercise equipment or peripherals that captures motion and activity information of a user engaged in physical activity while using the device. For example, the physical activity data capture device 2710 may be in the form of exercise equipment such as stand-on or ride-on exercise machines like treadmills, stair stepping machines, stationary bicycles, rowing machines, and weight-lifting or resistance devices, or may be other equipment wherein the user stands separately from the equipment and pulls or pushes on ropes, chains, resistance bands, bars, and levers. The physical activity data capture device 2710 may be in the form of computer peripherals (e.g., game controllers, virtual reality headsets, etc.) that capture data while the user is performing physical movements related to a game or virtual reality environment, or exercise equipment that engage the user in physical activity, such as barbells, free weights, etc., which are configured to provide location and/or motion information such an integrated motion sensors or external cameras configured to detect the peripheral. The physical activity data capture device 2710 may be in the form of exercise equipment or peripherals and may be referred to as an exercise device. Sensors in the physical activity data capture device 2710 may be either analog 2711 or digital 2712. Non-limiting examples of analog sensors 2711 are motor voltages and currents, resistors, potentiometers, thermistors, light sensors, and other devices that produce an analog voltages or currents. Most digital sensors are analog sensors 2711 with integrated analog-to-digital converters which output a digital signal, although some sensors are digital in the sense that they measure only discrete steps (e.g., an on/off switch). In most cases, signals from analog sensors 2711 will be converted to digital signals using an analog to digital converter 2701. For signals from digital sensors 2712, conversion is not necessary. In some cases, signals may need to be calibrated by a sensor calibrator, which corrects for sensor drift, out of range errors, etc., by comparing signals to known good values or to other devices.

The software application 2720 is any software designed to assign physical tasks and associative activities, to engage the user in the physical tasks and associative activities, and track and store data from physical tasks and responses to associative activities. The software application 2720 may have, or may use or access, a number of different software components such as a virtual reality game or environment generator 2721, an associative activity manager 2722 which designs, selects, and/or implements testing protocols based on the user's profile. Many different configurations of the software are possible. The software application 2720 may be configured to present tasks to the user independent of inputs from the physical activity data capture device 2710, such as performing playing games, performing math computations, remembering where certain symbols are located, visually following an object on a screen, or reading and speaking a given text. Alternatively, the software application 2720 may be configured to engage the user in mental or combined activities that correspond in some way to the inputs from the physical activity data capture device 2710. For example, the user might be running on a treadmill, and the speed of the treadmill might be used as an input to a virtual reality environment which shows the user virtually running at a rate corresponding to the rate of the real-world treadmill speed. The software application 2720 is configured to record data regarding, or evaluate and assign scores or values to, the user's responses and reactions to the tasks presented by the software application 2720. For example, if the user is assigned the task of performing a mathematical calculation, the correctness of the user's response may be evaluated, scored, and recorded as data. As another example, the user may be presented with the task of speeding up or slowing down a running motion in response to a visual cue, and the speed of the user's reaction may be recorded as data. In such cases, a data integrator 2730 may be used to integrate the data from the physical activity data capture device 2710 with the data from the software application 2720. In some embodiments, the data from the physical activity data capture device 2710 may be used to change the operation of the software application 2720, and vice versa (i.e., the software application 2720 may also be used change the operation of the exercise equipment, for example, providing additional resistance or speeding up the operation of a treadmill). In some embodiments, the data integrator may not be a separate component, and its functionality may be incorporated into other components, such as the software application 2720.

In some embodiments, the software application 2720, another machine-learning based software application such as a task assignment software application (not shown), may be configured to assign physical tasks to the user to be performed in conjunction with the associative activities assigned. Rather than simply continuously performing physical activity and recording the impact on the physical activity of performance of the associative activities, the user may be assigned discrete physical tasks to perform while a mental activity is being performed. For example, the user may be assigned the physical task of pointing to a fixed spot on a display screen while reading aloud a text, and the steadiness of the user's pointing may be measured before, during, and after the reading, thus indicating an impact on the user's physical activity of the mental effort. Such dual-task testing may allow for more precise measurement and evaluation of relative functioning as different combinations of physical and associative activities are evaluated together. In some embodiments, the associative activity may be a second physical task or activity assigned to be performed simultaneously with a primary physical task or activity. Note that the terms "task" and "activity" as used herein are interchangeable, although the phrases "physical task" and "associative activity" are often used for purposes of clarity and convenience.

Figure 28:
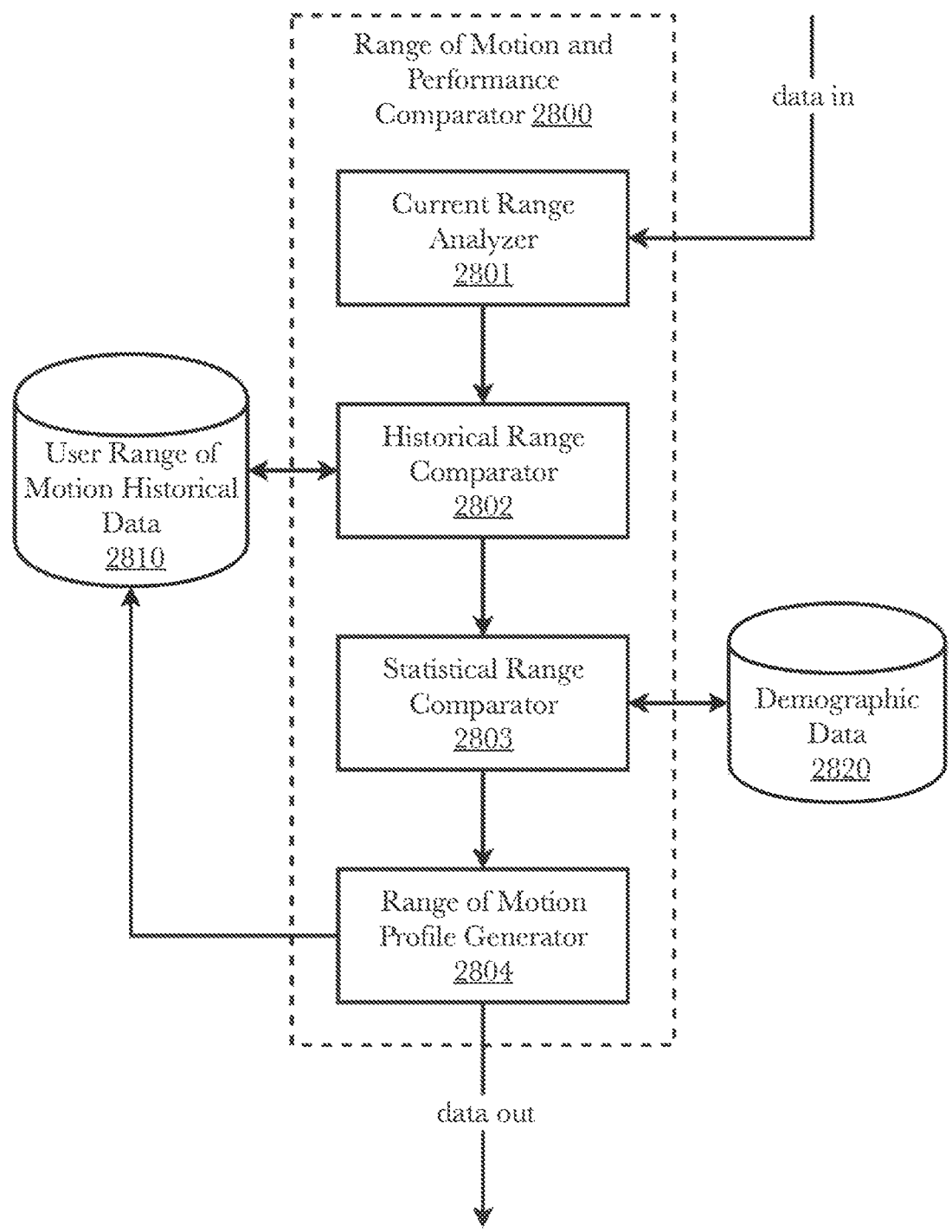
FIG. 28 is a system architecture diagram for the range of motion comparator aspect of a neurological functioning analyzer.

FIG. 28 is a system architecture diagram for the range of motion comparator aspect of a neurological functioning analyzer. The range of motion and performance comparator 2800 evaluates data from the data capture system 2700 to determine an individual's range of motion and performance for the given associative activity relative to the individual's personal history and relative to statistical norms. The range of motion and performance comparator 2800 comprises a current range analyzer 2801, a historical range comparator 2802, a statistical range comparator 2803, and a range of motion and performance profile generator 2804, as well as databases for user range of motion and performance historical data 2810 and demographic data 2820. The current range analyzer 2801 ingests data related to an individual's movement and performance and calculates a range of motion and performance of that individual while performing versus not performing the given associative activity. For example, if an individual is given a primary physical task of standing in balance and an associative activity of popping a virtual balloon of a specific color as it appears randomly in the VR environment, the current range analyzer 2801 will start tracking the individual's balance while performing the associative activity and measure the accuracy and timing of balloon popping (for testing the individual's gross motor and executive functions). To conclude, the individual is instructed to start walking to warm up, and then repeat the same balloon popping activity while walking. The current range analyzer 2801 will finish capturing all the motion and performance data—the differences in the individual's accuracy and timing of balloon popping between standing and walking as well as the nuanced changes in the individual's walking movement during warmup and while balloon popping—and forwarding its analysis to the historical range comparator 2801. The historical range comparator 2802 retrieves historical data for the individual (if such exists) from a user range of motion and performance historical data database 2810 and compares the current data with historical data to determine trends in the individual's motion and performance over time. The statistical range comparator 2803 retrieves statistical range data for populations similar to the individual from a demographic data database 2820, and determines a range of motion and performance of the individual relative to similar individuals by sex, age, height, weight, health conditions, etc. The range of motion and performance profile generator 2804 takes the data from the prior components and generates and stores a range of motion profile for the individual which integrates these analyses into a comprehensive picture of the individual's range of motion functionality.

Figure 29:
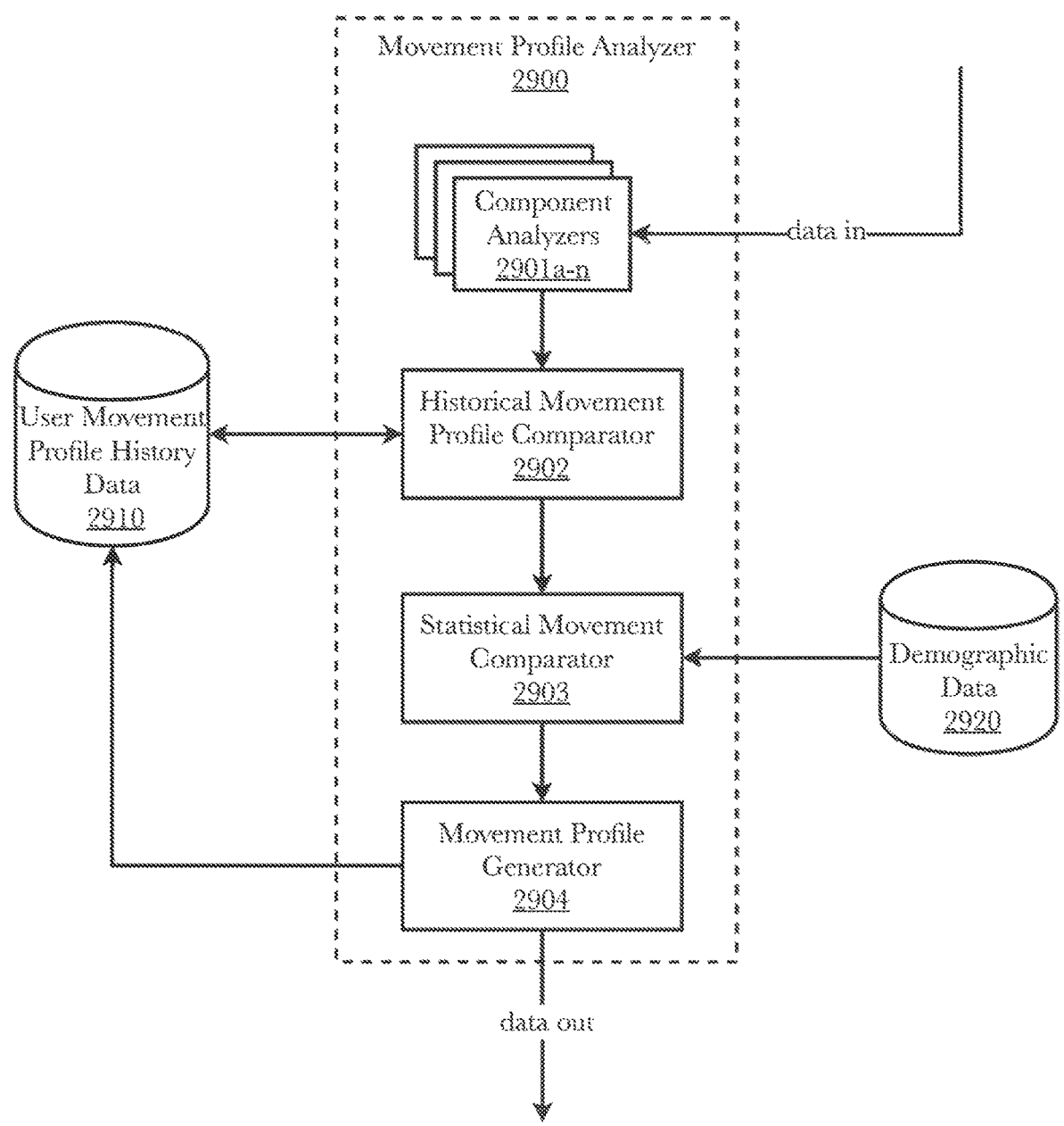
FIG. 29 is a system architecture diagram for the movement profile analyzer aspect of a neurological functioning analyzer.

FIG. 29 is a system architecture diagram for the movement and performance profile analyzer aspect of a neurological functioning analyzer. The movement and performance profile analyzer 2900 evaluates data from the data capture system 2700 to generate a profile of the individual's physical function such as posture, balance, gait symmetry and stability, and consistency and strength of repetitive motion (e.g., walking or running pace and consistency, cycling cadence and consistency, etc.) and mental performance such as executive function, cognitive response, visual and auditory functions, emotional or empathetic reactions, etc. The movement and performance profile analyzer 2900 comprises a number of component analyzers 2901*a-n*, a historical movement and performance profile comparator 2902, a statistical movement and performance comparator 2903, and a movement and performance profile generator 2904, as well as a user movement and performance profile history data database 2910 and a demographic data database 2920.

Many different aspects of movement and performance may be analyzed by the movement and performance profile analyzer 2900 through one or more of its many component analyzers 2901*a-n* such as the gait analyzer, balance analyzer, gross motor analyzer, fine motor analyzer, depth perception analyzer, executive function analyzer, visual function analyzer, auditory function analyzer, memory function analyzer, emotional response analyzer, etc. For example, the gait analyzer of the component analyzers 2901 ingests sensor data related to an individual's ambulatory movements (walking or running) while performing the given associative activity, and calculates a step frequency, step symmetry, weight distribution, and other metrics related to an individual's gait. These calculations are then compared to expected calculations for an individual without performing the given the associative activity. If an individual exhibits a limp while performing the given associative activity (e.g., popping virtual balloons), the step frequency, step symmetry, and weight distribution will all be skewed with the impaired side showing a shorter step duration and less weight applied. The expected calculations may be determined from the full range of sensor values, per-exercise calibrations, statistical data, or other means appropriate to the specific application. The balance analyzer of the component analyzer 2901 performs a similar function with respect to an individual's balance. Wobbling, hesitation, or partial falls and recoveries while performing a range of associative activities can be calculated from the data. The historical movement and performance comparator 2902 retrieves historical data for the individual (if such exists) from a user movement and performance historical data database 2910 and compares the current movement and performance data with historical data to determine trends in the movements and performances over time. The statistical movement and performance comparator 2903 retrieves statistical range of motion and performance data for populations similar to the individual from a demographic data database 2920, and compares movements and performances of the individual to similar individuals by sex, age, height, weight, health conditions, etc. The movement and performance profile generator 2905 takes the data from the prior components and generates and stores a movement and performance profile for the individual which integrates these analyses into a comprehensive picture of the individual's movement and performance functionality.

Figure 30:
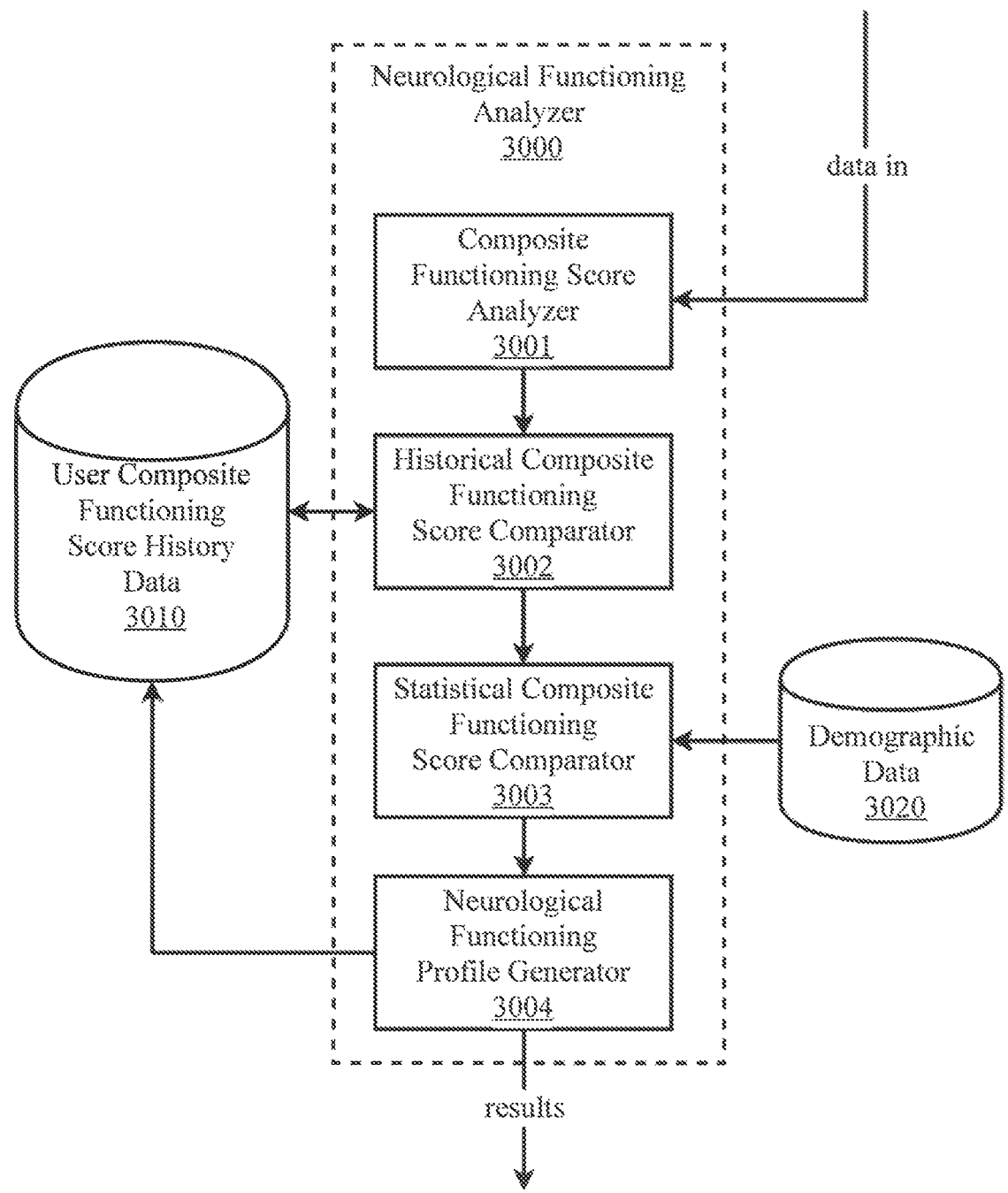
FIG. 30 is a system architecture diagram for the neurological functioning analyzer aspect of a neurological condition evaluator.

FIG. 30 is a system architecture diagram for the neurological functioning analyzer aspect of a neurological condition evaluator. The neurological functioning analyzer evaluates data from the data capture system 2700, the range of motion and performance comparator 2800, and the movement and performance profile analyzer 2900 to generate a profile of the user's nervous system function as indicated by composite functioning scores which indicate relative ability of an individual in one or more physical and mental functional measurement areas (also referred to herein as "composite functioning scores"). The current composite functioning score analyzer 3001 ingests sensor data related to an individual's movement and performance and calculates a set of current composite functioning scores for that individual based on the sensor data, the range of motion and performance profile, the movement and performance profile, and input from the software 2720 regarding associative activities associated with physical movement data. The historical composite functioning score comparator 3002 retrieves historical data for the individual (if such exists) from a user composite functioning score historical data database 3010 and compares the current composite functioning score data with historical data to determine trends in the individual's bio-makers over time. The statistical composite functioning score comparator 3003 retrieves statistical composite functioning score data for populations similar to the individual from a demographic data database 3020, and determines a range of composite functioning score functionality of the individual relative to similar individuals by sex, age, height, weight, health conditions, etc. The neurological functioning profile generator 3004 takes the data from the prior components and generates and stores a neurological functioning profile for the individual which integrates these analyses into a comprehensive picture of the individual's composite functioning score functionality. In some embodiments, one or more of the composite functioning scores may be determined from dual-task testing, in which a physical task and a mental task are performed simultaneously to detect areas of abnormal nervous system function, and/or identify which areas of the nervous system may be affected. For example, while performing mathematical tasks, an individual slows down significantly in his/her walk compared to the population data. It will indicate that the individual's composite functioning score for logical and mathematic functions is worse than his/her population cohort (by sex, age, height, weight, health conditions, etc.). The neurological functioning profile may include a composite functioning score spatial map as described above. In some embodiments, the neurological functioning analyzer may receive data directly from the data capture system 2700 and may perform independent neurological analyses without inputs from the range of motion and performance comparator 2800 or the movement and performance profile analyzer 2900 or may incorporate some or all of the functionality of those components.

Figure 33:
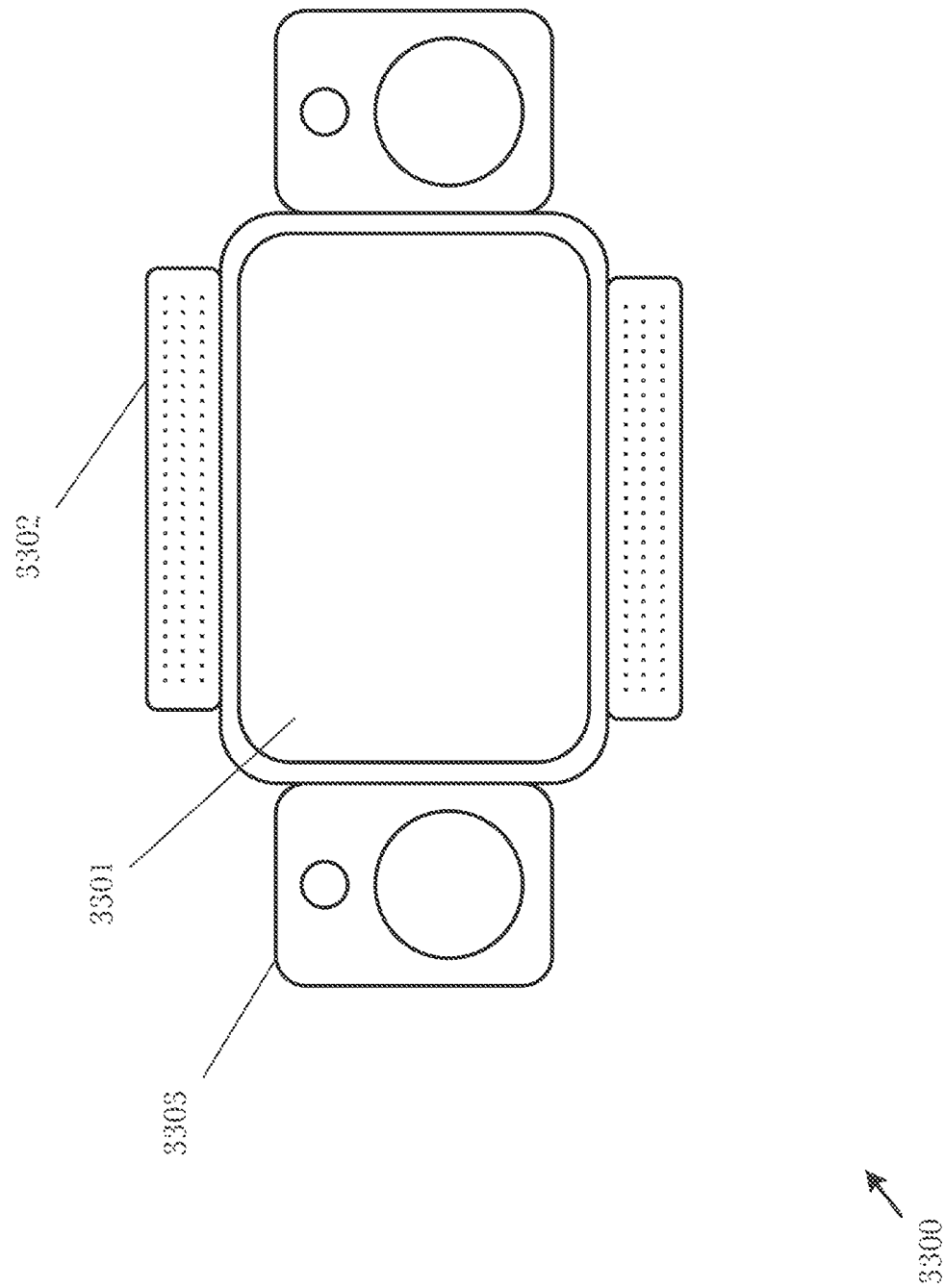
FIG. 33 is a diagram of an exemplary brainwave entrainment therapy device that can be attached to an exercise machine for targeted brainwave entrainment therapy with light and/or sound using dual-tasking methodologies.

FIG. 33 is a diagram of an exemplary brainwave entrainment therapy device that can be attached to an exercise machine for targeted brainwave entrainment therapy with light and/or sound using dual-tasking methodologies. In this embodiment, the brainwave entrainment therapy device comprises a screen 3301, one or more lights 3302, and one or more speakers or headphones 3303. The screen 3301 is used for display of activities designed to engage the user in one or more mental tasks associated with particular brain functionality. The lights 3302, shown here as light bars comprising multiple light-emitting diodes (LEDs) can be programmed to emit a visible stimulus (e.g., flashes, on/off cycles, etc.) at frequencies appropriate for brainwave entrainment. The speakers 3303 can be programmed to emit an audible stimulus (e.g., rectangular wave sound pulses, sine wave sound oscillations, etc.) at frequencies appropriate for brainwave entrainment. In some configurations, both light and sound may be used as stimuli. The stimuli need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus)

The device of this embodiment is designed such that can be mounted on an exercise machine (that may or may not be otherwise equipped for dual task stimulation purposes), whereby it can be used to provide dual task stimulation. The combination of the dual task stimulation with brainwave entrainment allows for stimulation of certain portions of the brain associated with certain neurological functions and allows for targeted brainwave entrainment by enhancing and concentrating the effect of the brainwave entrainment on the stimulated areas of the brain. As one example, a person with memory loss may be provided dual task stimulation such as walking on a treadmill (physical task) while playing a memory-based card matching or tile matching game (associated mental activity). While the person is engaged in the dual task stimulation, brainwave entrainment is applied via the lights 3302 (or via the screen in some applications) and/or the speakers 3303. As the neurological functions in the brain associated with memory are being stimulated), the neurons in the brain associated with those functions are in an already-stimulated state, and the brainwave entrainment's stimulation of oscillations in the electrochemical state of neurons in those already-stimulated areas will have a more pronounced effect than on other areas of the brain. In this way, the already-stimulated areas of the brain will experience a greater reduction in degenerative conditions (i.e., reductions in amyloid plaques and tau phosphorylation) and greater increases in synaptic density.

Figure 34:
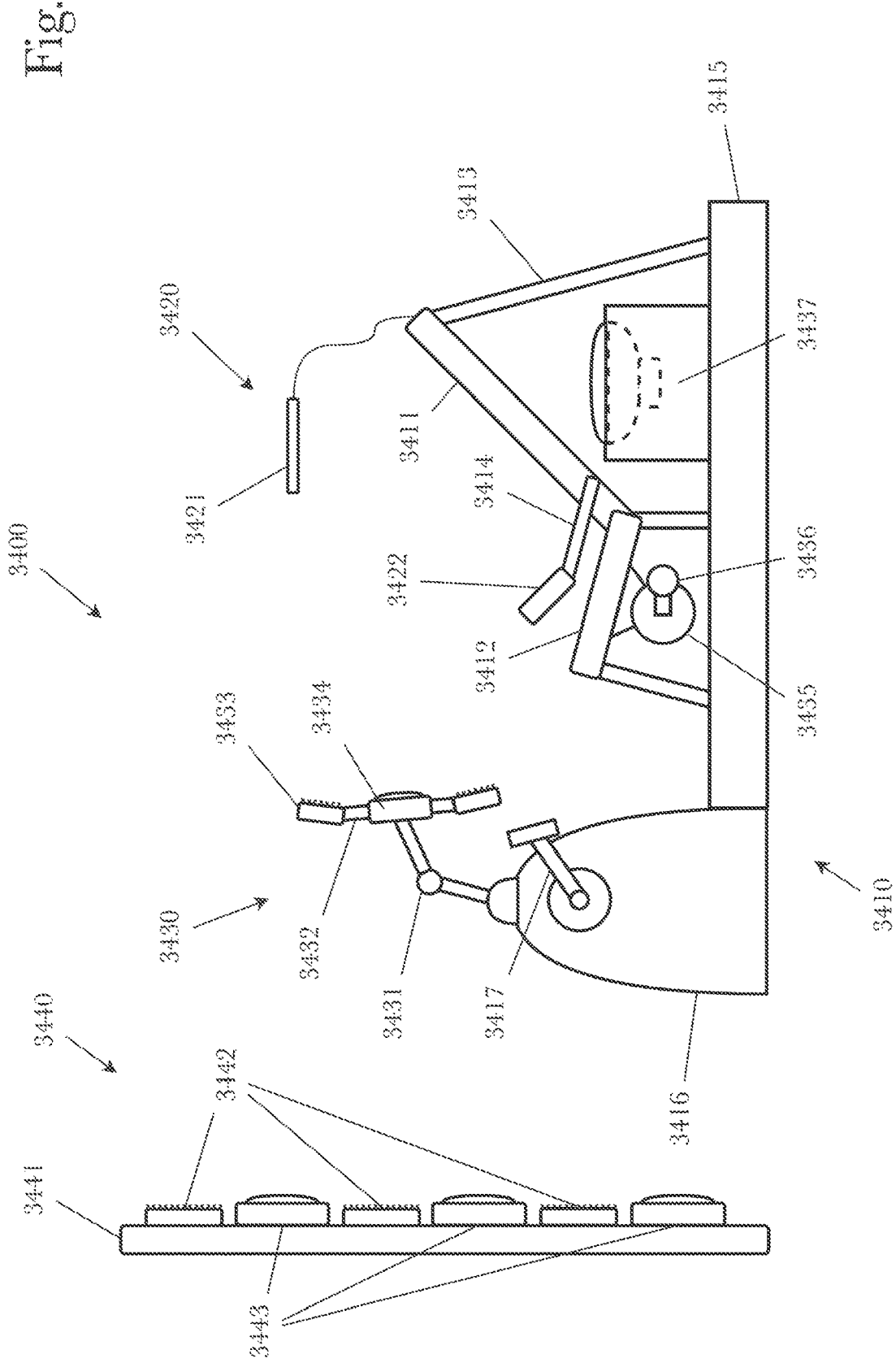
FIG. 34 is a diagram of an exemplary brainwave entrainment therapy system for targeted brainwave entrainment therapy that allows for multi-modal, multi-intensity treatment using dual-tasking methodologies.

FIG. 34 is a diagram of an exemplary brainwave entrainment therapy system for targeted brainwave entrainment therapy that allows for multi-modal, multi-intensity treatment using dual-tasking methodologies. The system 3400 of this embodiment comprises a stationary recumbent bicycle 3410, and three different scales of brainwave entrainment stimulators: localized and/or individual stimulation transducers 3420, small area stimulation transducers 3430, and large area stimulation transducers 3440.

The stationary recumbent bicycle 3410 comprises a base 3415, a chair back 3411, a seat 3412, arm rests 3414, a plurality of supports 3413 connecting the chair back 3411 and seat 3412 to the base 3415, a resistance mechanism 3416 allowing for resistance to a pedaling motion of the user, and a pedal system 3417 for the user to pedal in a cycling motion. The stationary recumbent bicycle 3410 thus provides the means for the user to engage in a physical task for dual task stimulation (and/or dual task assessment).

The localized and/or individual stimulation transducers 3420 of this embodiment are a headband 3421 with vibratory stimulation and hand grips 3422 which provide electrical stimulation. These provide localized stimulation which can only be perceived by the user, which also makes them individual stimulation transducers (as opposed to the other scales, which can be perceived by others, and which could be used to provide brainwave entrainment to more than one person using the same transducer(s)). The headband may produce simple vibratory (i.e., tactile) stimulation to the head, or may be configured to produce vibrations at certain locations on the head and at certain intensities so as to be perceptible by the middle and inner ear, which causes the stimulation to be both tactile and auditory in nature. This double stimulation (tactile and auditory) amplifies the effect of a single type of transducer, increasing the efficiency of brainwave entrainment from applications of that transducer.

The small area stimulation transducers 3430 of this embodiment are devices attached to the exercise machine 3410, but not directly attached to or in contact with the user. For example, a console comprising a screen 3432, light bars 3433, and speakers 3434 similar to that of the device of FIG. 33 may be used. The console may be attached to the exercise machine using an adjustable arm 3431 that allows for optimal positioning of the console for viewing and/or interaction by the user. Other small area stimulation transducers include a large electric motor 3435 with an offset weight 3436 attached to the seat 3412 that allows for full-body vibratory stimulation to be applied, and a subwoofer 3437 under the chair back 3411 that allows for both audible (regular sound) and inaudible (infrasound) stimulation to be applied. Small area stimulation transducers are particularly useful in situations where direct contact with a user is not desirable, or when multiple users will be using the device sequentially, or when brainwave entrainment will be applied to a small number of users (e.g., those directly in front of the stimulation transducers).

The large area stimulation transducers 3440 of this embodiment are devices that can be used over a large area and potentially a large number of persons such as a room or auditorium. In this embodiment, the large area stimulation transducers are large LED light bars 3442 and large speakers 3443 attached to a wall 3441 of the room in which the stimulation will be applied. The large area stimulators such as the LED light bars 3442 and large speakers 3443 on the wall 3441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

It is important to note that any type of transducer can be applied at any scale. For example, light stimulation can be configured such that it is seen only by one person (e.g., in glasses or goggles), or is seen by a small number of persons (e.g., a single LED light bar), or is seen by many people (e.g., room lights, stadium lights, etc.). Further, the intensity of stimulation can be largely varied separately from the scale of stimulation. However, depending on the circumstances and application, brainwave entrainment at certain scales and/or intensities may be more useful or effective than at others.

The different scales of stimulation transducers allow for a choice of the level of immersion the user experiences with respect to the brainwave entrainment, and to some degree, the level of intensity of the brainwave entrainment. Immersion is the quality of being surrounded by or absorbed in an experience. Intensity is the magnitude of the experience. They are separate qualities (e.g., a localized electric stimulation can be intense, but not immersive), but there can be an increase in intensity with an increase in scale (for example, if light stimulation comes from all directions, it will tend to be both more immersive and more intense, although the intensity of the lights can be reduced to offset this tendency). For example, a localized, subtle electrical stimulation through electrically-conducting hand grips 3422 provides minimal immersion of the user in the brainwave entrainment. This may be useful, for example, where intense concentration on the dual task stimulation is necessary. Small area stimulation transducers such as the LED light bars 3433 on the screen console are useful for mid-level immersion and mid-level intensity of brainwave entrainment. The LED light bars 3433 cover a small, but significant, area of the user's view, and the speakers 3434 are large enough to provide a substantial auditory stimulus. The large area stimulators such as the LED light bars 3442 and large speakers 3443 on the wall 3441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

Further, it is important to note that the modalities (types of stimulation), scales, and intensities allows for tremendous flexibility in selecting suitable therapies regimens for different situations. For high-immersion scenarios (e.g., maximum brainwave entrainment with fewer cognitive demands such as listening to music), multiple modalities, scales, and intensities may be used at the same time. For example, while a user is listening to classical music, localized electrical stimulation may be applied to the wrist, small area visual stimulation may be applied using a single LED light bar, and large area tactile stimulation may be applied using subwoofers which produce sounds (infrasounds) which are inaudible to the human ear but can be perceived through the sense of touch (e.g., as oscillating pressure on the torso).

Further, modalities can be chosen to either amplify certain tasks or activities or to supplement them. For amplification, treatment modalities are chosen to include those corresponding to a given task or activity in dual task stimulation. As an example, if a dual task stimulation activity assigned to a user is listening to music, a 40 Hz auditory signal can be used as gamma entrainment therapy. As the user is already focused on listening, the user is focusing more intensely on auditory activities (and the brain areas and functions associated with auditory activities are stimulated), enhancing the effect of the auditory gamma entrainment modality. For supplementation, treatment modalities are chosen to exclude those corresponding to a given task or activity in dual task stimulation. As an example, if a dual task stimulation activity assigned to a user is listening to specific songbirds for the purpose of identifying or counting them, adding a 40 Hz auditory signal may interfere with the listening process, thus either disrupting the dual task stimulation or causing the gamma entrainment to be ineffective. In such circumstances, a non-conflicting modality may be chosen such as light therapy or vibratory therapy.

Figure 35:
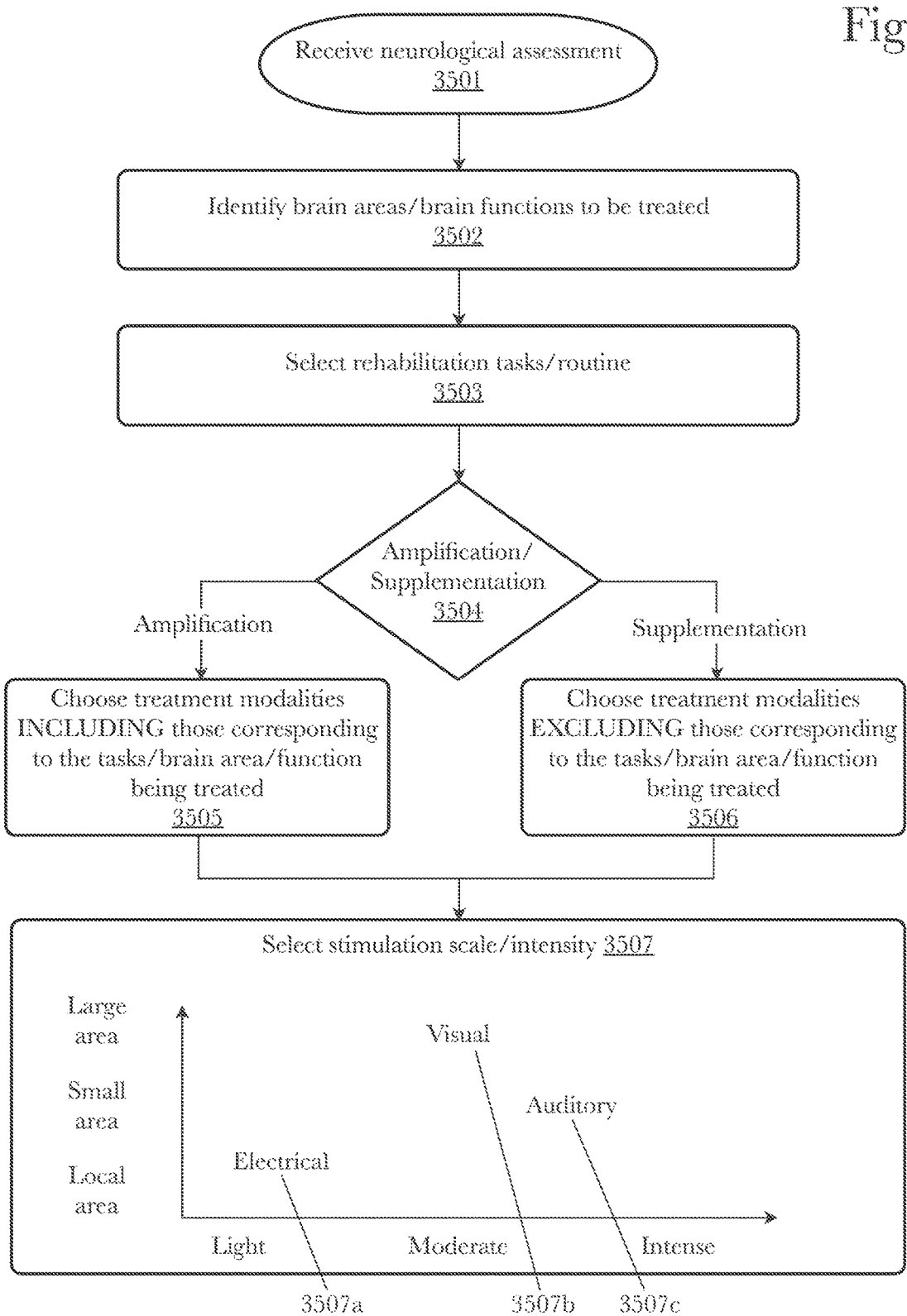
FIG. 35 is a flow diagram showing an algorithm for selection of modalities and routines for targeted brainwave entrainment therapy using dual-tasking methodologies.

FIG. 35 is a flow diagram showing an algorithm for selection of modalities and routines for targeted brainwave entrainment therapy using dual-tasking methodologies. As a first step, a neurological assessment is received 3501, comprising an evaluation of neurological function of at least one aspect of an individual. The neurological assessment may be in any number of different forms. One possible form is a report of a physician or other health professional identifying a deficiency in neurological function such as a cognitive or motor-physical decline associated with neurological disease or degradation. Another possible form is a report from a coach or other sports professional recommending an improvement in some area of training or physical performance. Another possible form is the results of a dual task assessment. After the neurological assessment is received, the areas of the brain or neurological functions to be treated are identified 3502. Where the neurological assessment is a dual task assessment or obvious neurological deficiency (i.e., disease or degradation), the deficient neurological functions will be known, and brain areas associated with those neurological functions may also be known. Where the neurological assessment is a training or physical performance improvement recommendation, a neurological function may be selected which is believed to be associated in some form with that recommended improvement.

A treatment regimen is then created by selecting appropriate dual task stimulation to stimulate the areas of the brain to be treated 3503, selecting amplification or supplementation 3504 as appropriate for the dual task stimulation, choosing appropriate treatment modalities (e.g., light therapy, sound therapy, vibrational therapy, electrical therapy, or combinations of such modalities) either for amplification 3505 (treatments including those corresponding to the tasks, activities, or neurological function) or for supplementation 3506 (treatments including those corresponding to the tasks, activities, or neurological function), and selecting a stimulation scale and intensity 3507 for each modality appropriate for the treatment goals. In this example, three modalities are shown with different scales and intensities, localized electrical stimulation at a light intensity 3507a, large area visual stimulation at a moderate intensity 3507b, and small area auditory stimulation at a moderately intense intensity 3507c. Brainwave entrainment is then applied using the chosen regimen, providing targeted treatment of particular areas of the brain and/or particular neurological functions via stimulation of those areas or functions using dual task stimulation.

Figure 36:
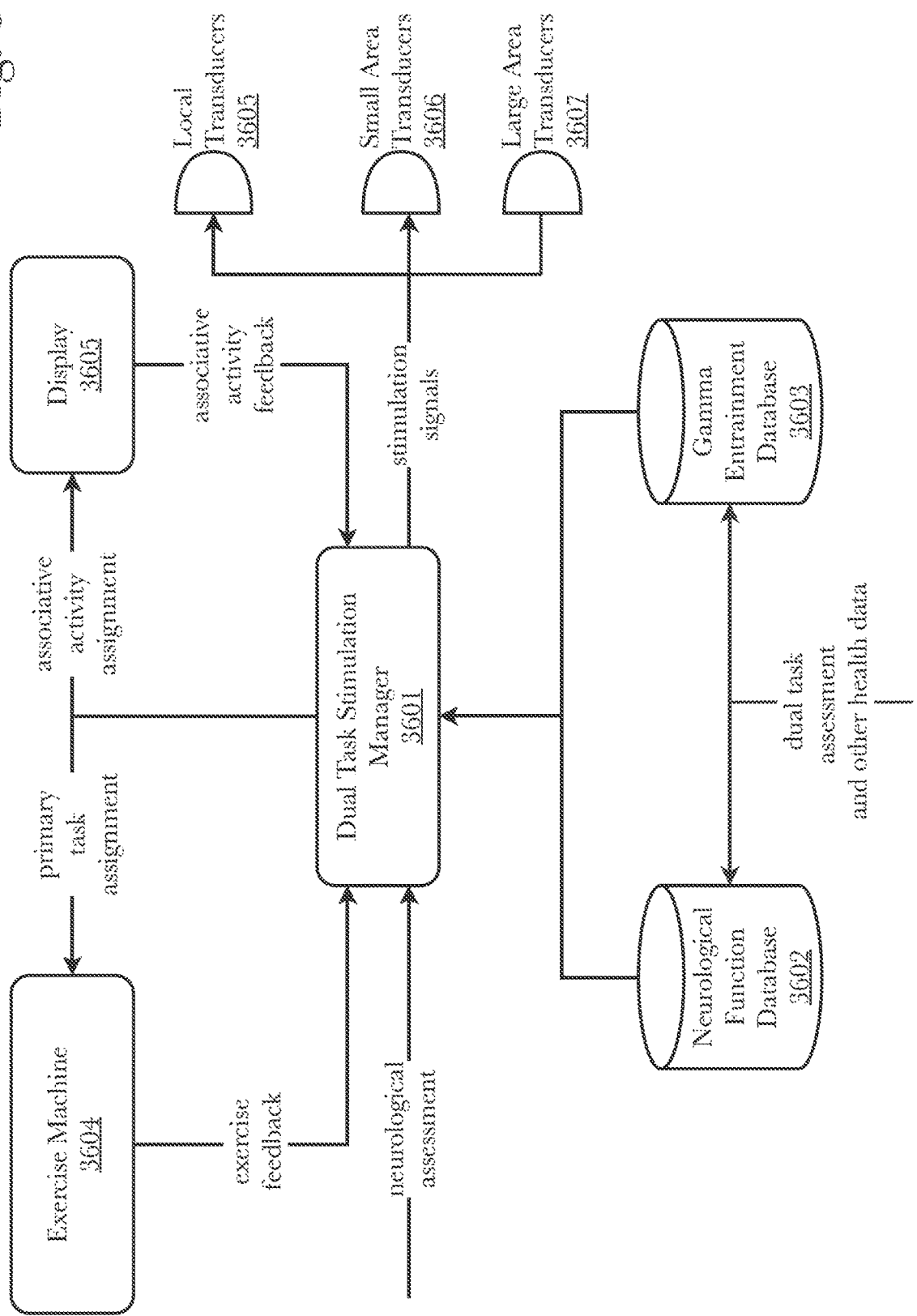
FIG. 36 is a diagram showing an exemplary system architecture diagram for targeted brainwave entrainment therapy using dual-tasking methodologies.

FIG. 36 is a diagram showing an exemplary system architecture diagram for targeted brainwave entrainment therapy using dual-tasking methodologies. In this embodiment, the system architecture 3600 comprises a dual task stimulation manager 3601, a neurological function database, a brainwave entrainment database, an exercise machine 3604, and three scales of transducers, localized stimulation transducers 3605, small area stimulation transducers 3606 and large area stimulation transducers 3607.

The dual task stimulation manager 3601 is responsible for receiving neurological assessments, each comprising a neurological condition to be treated, and creating therapy regimens to treat the neurological condition. The neurological assessment may be in any number of different forms. One possible form is a report of a physician or other health professional identifying a deficiency in neurological function such as a cognitive or motor-physical decline associated with neurological disease or degradation. Another possible form is a report from a coach or other sports professional recommending an improvement in some area of training or physical performance. Another possible form is the results of a dual task assessment. It is important to note that a neurological assessment does not necessarily mean an assessment of a deficiency. It may note normal function but indicate a neurological condition for improvement. The dual task manager 3601 creates a therapy regimen based on the neurological condition by consulting the neurological database 3602 and the brainwave entrainment database.

The neurological database 3602 is a database containing information that associates neurological conditions with primary tasks and associative activities (i.e., dual tasking tasks and their associated activities). This database may be developed from pre-existing information or may be built up over time from dual task assessments. The brainwave entrainment database 3603 is a database of information about brainwave entrainment therapies (i.e., modalities, immersion, intensity, and stimulation frequencies) tending to be more or less effective under certain conditions and in certain situations, including conditions and situations associated with dual task stimulation. The brainwave entrainment database may likewise be developed from pre-existing information or may be built up over time from dual task assessments. Importantly, both the neurological database 3602 and the brainwave entrainment database may store neurological assessment data for particular individuals over time and use the results of the neurological assessments of each such individual to create therapy regimens for that individual. This provides concrete information about the effectiveness of created therapy regimens on a given individual and allows for future therapy regimens to be adjusted to meet the needs of that individual.

Once a therapy regimen is created, the dual task stimulation manager assigns dual task stimulation to the individual undergoing treatment comprising a primary task and an associative task. In this case the primary task involves exercise on an exercise machine 3604, and the associative task involves solving puzzles on a display 3605. The exercise machine provides feedback to the dual task stimulation manager 3601 as to whether the primary task is being performed, and the display provides feedback as to whether the associative activity is being performed. While the dual task stimulation is being performed, the dual task stimulation manager sends signals to the appropriate transducers 3605-3607 to operate them according to the appropriate stimulation frequency.

Figure 39:
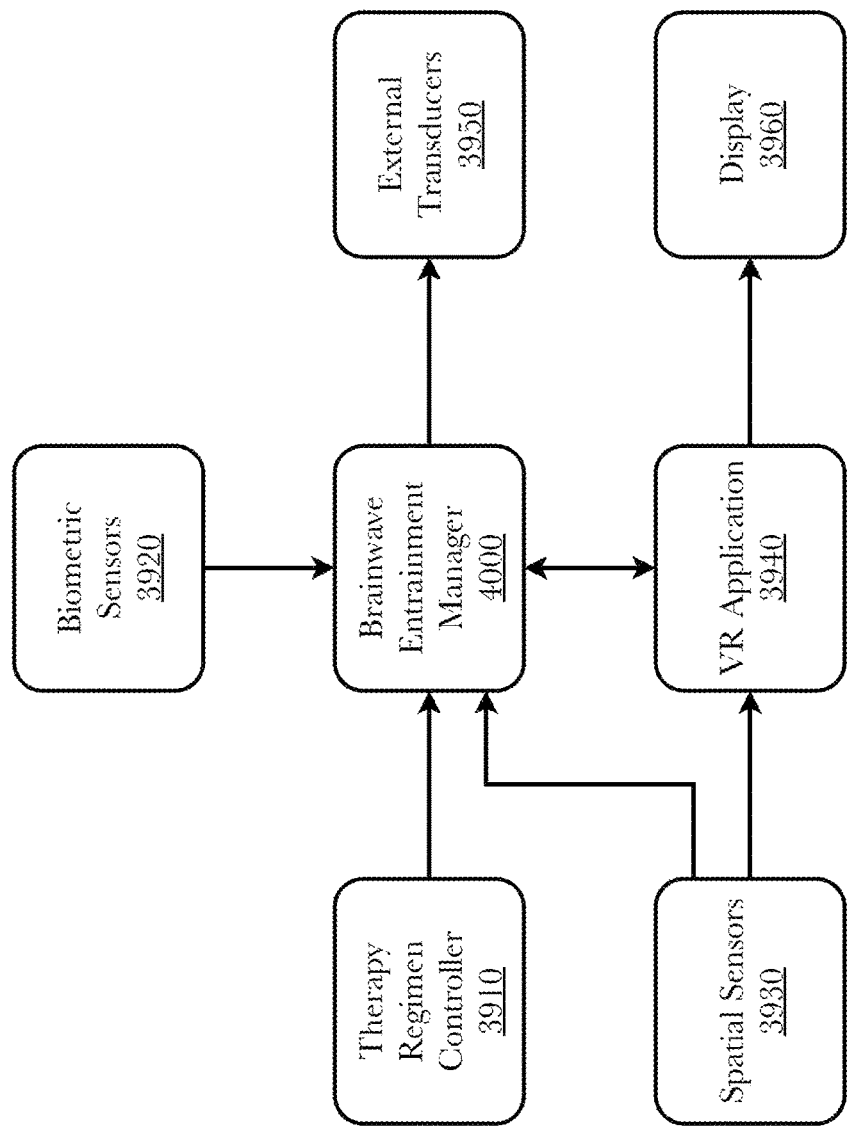
FIG. 39 is a diagram showing an exemplary overall system architecture for a brainwave entrainment system using virtual objects and environments as visual, stimulation transducers.

FIG. 39 is a diagram showing an exemplary overall system architecture 3900 for a brainwave entrainment system using virtual objects and environments as visual stimulation transducers. In this embodiment, the system comprises a brainwave entrainment manager 4000, a virtual reality (VR) application 3940, a therapy regimen controller 3910, one or more spatial sensors 3930, one or more biometric sensors 3920, and one or more external transducers, and a display 3960.

The brainwave entrainment manager 4000 is the core of the system, and manages inputs from, and outputs to, other components of the system. It is responsible for selection of entrainment routines, evaluation of the user's attention, and activation of both virtual and physical stimulation transducers.

The therapy regimen controller 3910 is an administrative interface that allows an administrator (e.g., a physician, therapist, masseuse, or other service provider) to select therapy regimens for application to the user (who may be a patient, client, etc., of the administrator). The therapy regimen controller 3910 may be used, for example, to select a regimen for brainwave entrainment that emphasizes alpha wave stimulation to induce relaxation in an overstimulated user.

The biometric sensors 3920 are sensors that measure a physical or physiological characteristic of the user, such as heart rate, temperature, sweat production, brain activity (using an electroencephalograph, or EEG), etc. Biometric sensors 3920 are used to provide feedback to the brainwave entrainment manager 4000 as to the physical or physiological state of the user, which may be used to infer the user's mental state. For example, a biometric sensor 3920 that measures the user's heart rate may be used to infer the user's level of relaxation (or lack thereof), thus providing feedback as to the effectiveness of alpha brainwave entrainment intended to induce relaxation.

Spatial sensors 3930 are sensors that measure a user's physical location in space or a location at which the user is focusing his or her attention. For two dimensional screens, eye movement may be tracked, and the location of the user's gaze may be calculated. In the case of virtual reality (VR), the user's body may be tracked, or if the user is wearing a VR headset, the orientation of the headset can be used to detect the user's head movements. Spatial sensors 3930 are used to detect the user's engagement with virtual objects and virtual environments, such that brainwave entrainment using those objects and environments can be adjusted, accordingly.

The VR application 3940 is used for gamification of brainwave entrainment. While a VR application 3940 is shown here, in principle any computer game, puzzle, display, or animation can be used, whether interactive or not, and whether three-dimensional or two-dimensional. The VR application 3940 can be a specially-designed program intended for use with the system, or can be an off-the-shelf game or application adapted for use with the system. In either case, the VR application 3940 will either have an interface with the brainwave entrainment manager 4000, or will have a brainwave entrainment manager 4000 integrated into it, whereby the brainwave entrainment manager 4000 is used to control brainwave entrainment using the virtual objects in the VR application 3940.

The external transducers 3950 are physical stimulation transducers that may be used to complement brainwave entrainment using virtual objects. A non-limiting list of external transducers 3950 includes lights or LEDs, speakers or other audio-producing devices, vibratory or other pressure-producing devices, and electrical stimulators. As an example, while brainwave entrainment is being applied visually using virtual objects on a screen, the brainwave entrainment may be supplemented or complemented by audible brainwave entrainment using speakers.

The display 3960 may be any type of display producing an output visible to a user of the system. A non-limiting list of displays 3960 includes computer and tablet screens, VR headsets, and projectors. The display 3960 is the means by which visual brainwave entrainment may be applied using virtual objects.

Figure 40:
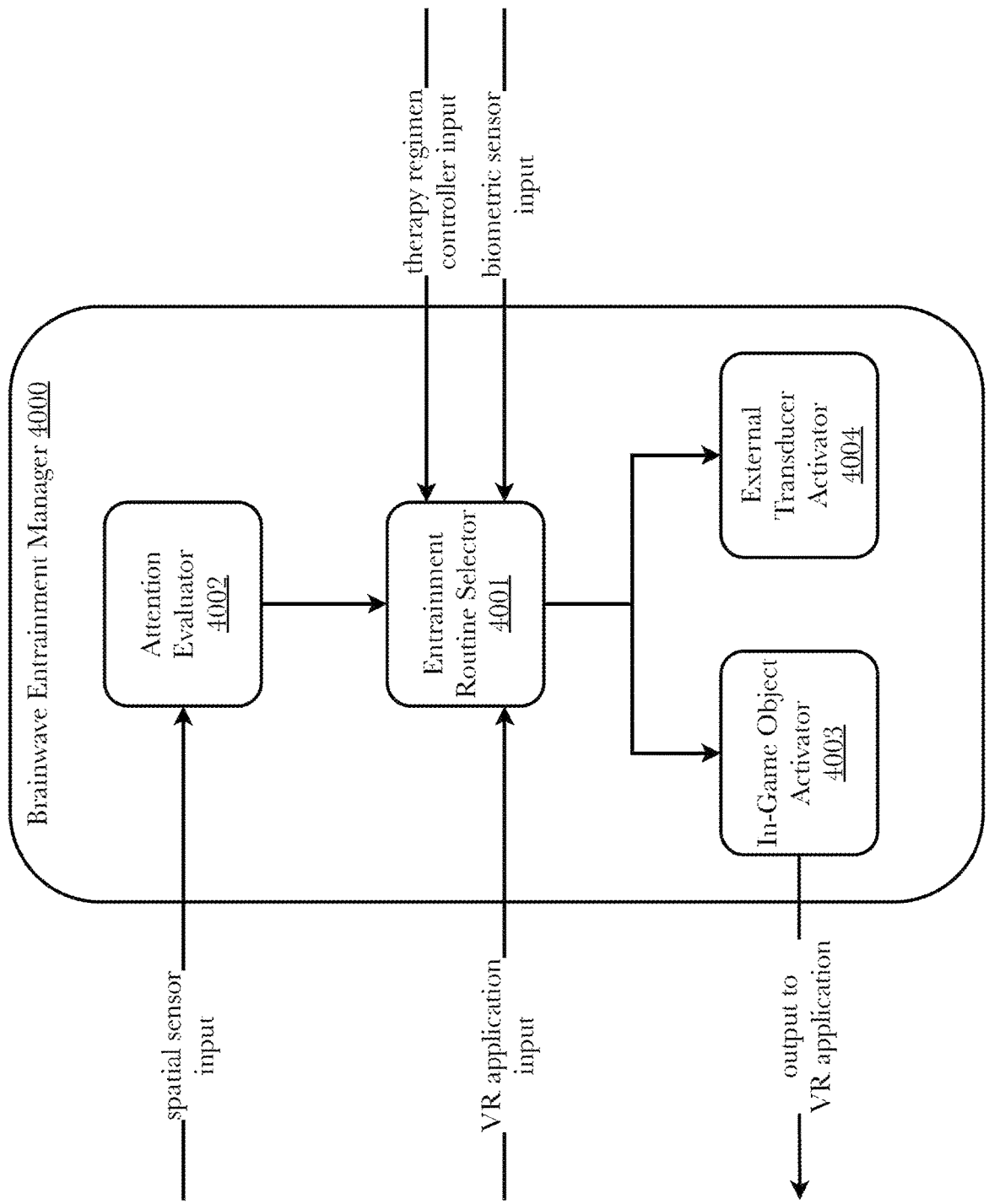
FIG. 40 is a diagram showing an exemplary architecture for the brainwave entrainment manager aspect of the brainwave entrainment using virtual objects and environments as visual, stimulation transducers.

FIG. 40 is a diagram showing an exemplary architecture for the brainwave entrainment manager aspect of the brainwave entrainment using virtual objects and environments as visual stimulation transducers. In this embodiment, the brainwave entrainment manager 4000 comprises an entrainment routine selector 4001, an attention evaluator 4002, an in-game object activator 4003, and an external transducer activator 4004. The entrainment routine selector 4001 receives input VR application input, therapy regimen controller input, and biometric sensor input, and input from the attention evaluator 4002. Based on those inputs, the entrainment routine selector chooses and/or modifies a brainwave routine appropriate for the circumstances. For example, if the therapy regimen controller input specifies that the overall brainwave entrainment goal is relaxation, the entrainment routine selector 4001 may select alpha wave entrainment as the primary entrainment therapy, and may choose to apply alpha wave entrainment to a background virtual object, as flashing of background objects will be less intrusive (and possibly more relaxing) to the user than flashing of objects to which the user's attention is directed. To determine which objects are not the subject of the user's attention, the attention evaluator 4002 receives input from a spatial sensor (e.g., a camera used to track eye movements) to determine where the user is looking on the screen at a given moment. The entrainment routine selector 4001 then modifies the entrainment routine to flash an object or objects at which the user is not looking using an in-game object activator 4003 which interfaces with the VR application to identify which objects should be flashed.

The user's attention need not be tracked via a camera and may be tracked through other means. For example, the user's attention may be tracked by monitoring the user's interaction with the virtual objects or virtual environment in the form of mouse clicks, keyboard activity, orientation of the user's head or body (e.g., when a virtual reality headset is being used), orientation and/or movement of hand-held trackable devices such as game controllers with integrated accelerometers, gyroscopes, etc. In some embodiments, the user's attention may be tracked not in terms of visual direction or attention, but in the more general sense of focus, consistency, ability to concentrate, level of interest, response times, or other factors not necessarily associated with the direction of the user's vision. All of these things may be incorporated into decisions by the entrainment routine selector 201 as to changes to be made to the entrainment routine.

Simultaneously, the entrainment routine selector 4001 may activate one or more external transducers 4004 using an external transducer activator 4004, where the entrainment routine selector 4001 determines that external transducers may supplement or complement the brainwave entrainment using virtual objects. The entrainment routine selector 4001 may further use feedback to determine whether the selected entrainment routine is having the desired effect. As an example, the entrainment routine selector 4001 may use biometric feedback such as a user's heart rate (e.g., a lowering heart rate may be used to infer relaxation) to change the entrainment routine. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation.

Many other types and implementations of feedback are possible including, but not limited to, changing of entrainment routines based on user reactions to, or interactions with, virtual objects and virtual environments; user attention attributes such as the location, intensity, focus, and consistency of user attention to virtual objects and virtual environments; game scores and other gaming metrics; physical biofeedback such as monitoring heart rate, perspiration, respiration; cognitive biofeedback such as monitoring changes in an EEG; exercise equipment feedback such as treadmill speed, cycling cadence and/or power, rowing strokes per minute and/or power. Further, entrainment routines can be changed to use different types of stimulation (e.g., if the feedback indicates that visual stimulation is less effective at certain points in a game, it can be supplemented with auditory or haptic feedback). Multiple stimulation devices can be used to augment or supplement the visual stimulation including, but not limited to, haptic headbands or vest, speakers or headphones, and other stimulation devices. In this way, the system can be programmed to automatically adapt to users based on a variety of feedback sources.

Figure 41:
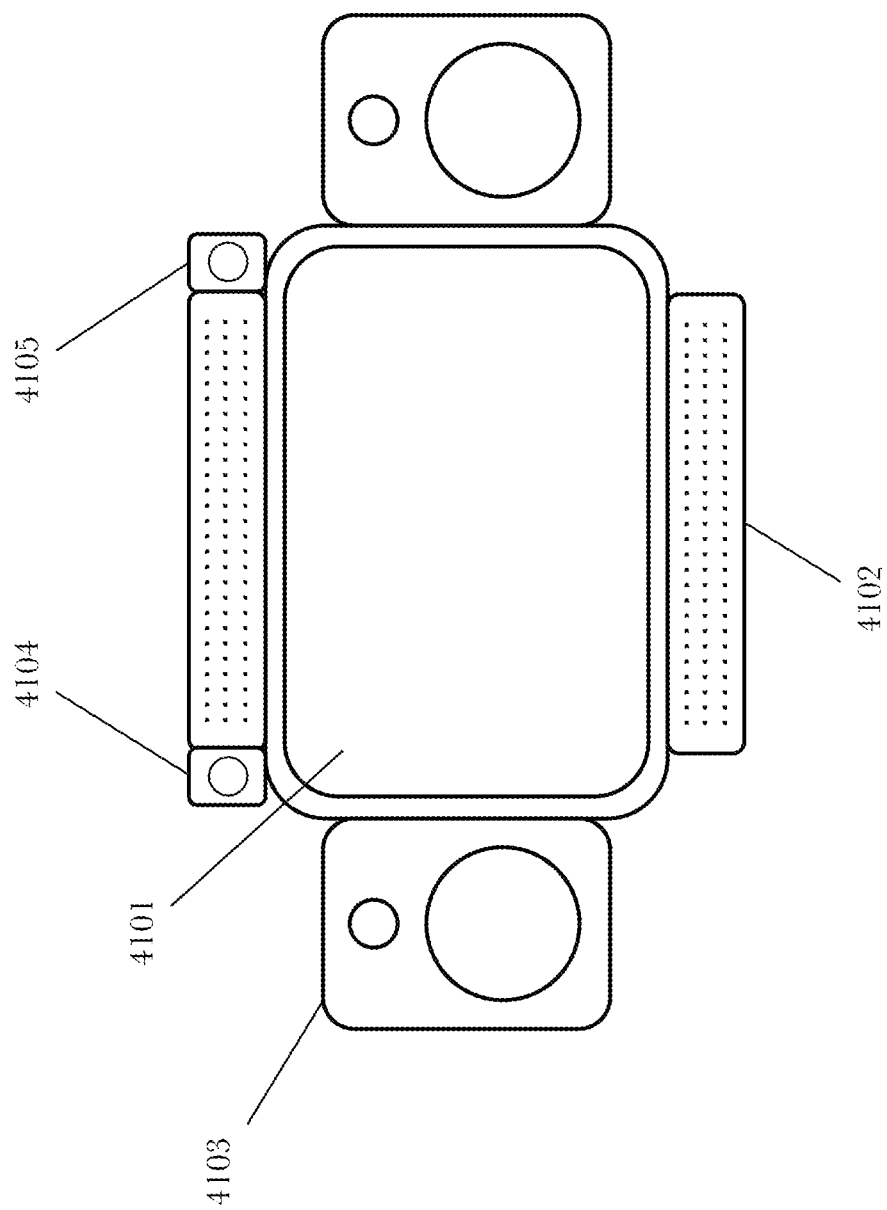
FIG. 41 is a diagram of an exemplary brainwave entrainment therapy device that can be attached to an exercise machine for targeted brainwave entrainment therapy with attention tracking and virtual objects.

FIG. 41 is a diagram of an exemplary brainwave entrainment therapy device that can be attached to an exercise machine for brainwave entrainment therapy with light and/or sound, including brainwave entrainment using virtual objects. In this embodiment, the brainwave entrainment device comprises a display 4101, one or more lights 4102, and one or more speakers or headphones 4103. The display 4101 is used for display of activities designed to engage the user in games or other activities while brainwave entrainment is applied using virtual objects on the display. The lights 4102, shown here as light bars comprising multiple light-emitting diodes (LEDs) can be programmed to emit a supplemental visible stimulus (e.g., flashes, on/off cycles, etc.) at frequencies appropriate for brainwave entrainment. The speakers 4103 can be programmed to emit a supplemental audible stimulus (e.g., rectangular wave sound pulses, sine wave sound oscillations, etc.) at frequencies appropriate for brainwave entrainment. In some configurations, both light and sound may be used as stimuli, separately or in conjunction with brainwave entrainment using virtual objects on the display 4101. The stimuli need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus)

The device of this embodiment is designed such that can be mounted on an exercise machine (that may or may not be otherwise equipped for brainwave entrainment purposes), whereby it can be used to provide brainwave entrainment using virtual objects on the display 4101, optionally with supplemental brainwave entrainment from the lights 4102 and/or speakers 4103. The use of virtual objects with brainwave entrainment allows for flexibility in applying brainwave entrainment. Brainwave entrainment using virtual objects provides essentially unlimited variability in terms of stimulator sizes, shapes, colors, movements, and allows for the use of multiple stimulators simultaneously, each with different characteristics. Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the virtual objects, stimulation can be applied based on where the user's attention is focused. Attention-based stimulation provides opportunities for both direct stimulation (e.g., flashing an object at which the user is looking) and indirect stimulation (e.g., flashing an object in the user's periphery of vision). For example, eye tracking technology can be used to determine where the user is looking on the screen at any given time, and objects at which the user is looking can be used to provide visual stimulation even if the user changes his or her attention to a different object on the screen. In this embodiment, an infrared emitter 4104 emits an infrared light, which is reflected off the user's eye and cornea, and is received at an infrared-sensitive camera 4105. The center of the eye is tracked in relation to a reflection from the cornea (the outer surface of the eye). The distance and direction of the difference between the center of the eye and the corneal reflection can be used to calculate the eye's position. Combined with a known distance to and size of the display 4101 the location at which the user is looking can be determined. The user's attention to objects on the screen can be monitored over time to determine whether the user is remaining focused on the activity, or is getting tired and losing focus, and the determined level of user attention can be used to change the type, intensity, directness, and other characteristics of the stimulation.

Brainwave entrainment using virtual objects may be further enhanced by using multiple objects, each capable of providing complementary types of stimulation, and/or by intentionally directing the user's attention to objects providing certain types of stimulation. For example, if the user is playing a first-person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Application of brainwave entrainment using virtual objects and gamification allows for brainwave entrainment to target certain neurological functions by enhancing and concentrating the effect of the brainwave entrainment on the stimulated areas of the brain. As one example, a person with memory loss may be asked to play a memory-based card matching or tile matching game (mental activities which stimulate certain portions of the brain). While the person is engaged in the mental activity, brainwave entrainment is applied via the game objects on the display 4101 and/or the lights 4102 and/or speakers 303. As the neurological functions in the brain associated with memory are being stimulated, the neurons in the brain associated with those functions are in an already-stimulated state, and the brainwave entrainment's stimulation of oscillations in the electrochemical state of neurons in those already-stimulated areas will have a more pronounced effect than on other areas of the brain. In this way, the already-stimulated areas of the brain may experience a greater reduction in degenerative conditions (i.e., reductions in amyloid plaques and tau phosphorylation) and greater increases in synaptic density.

Figure 42:
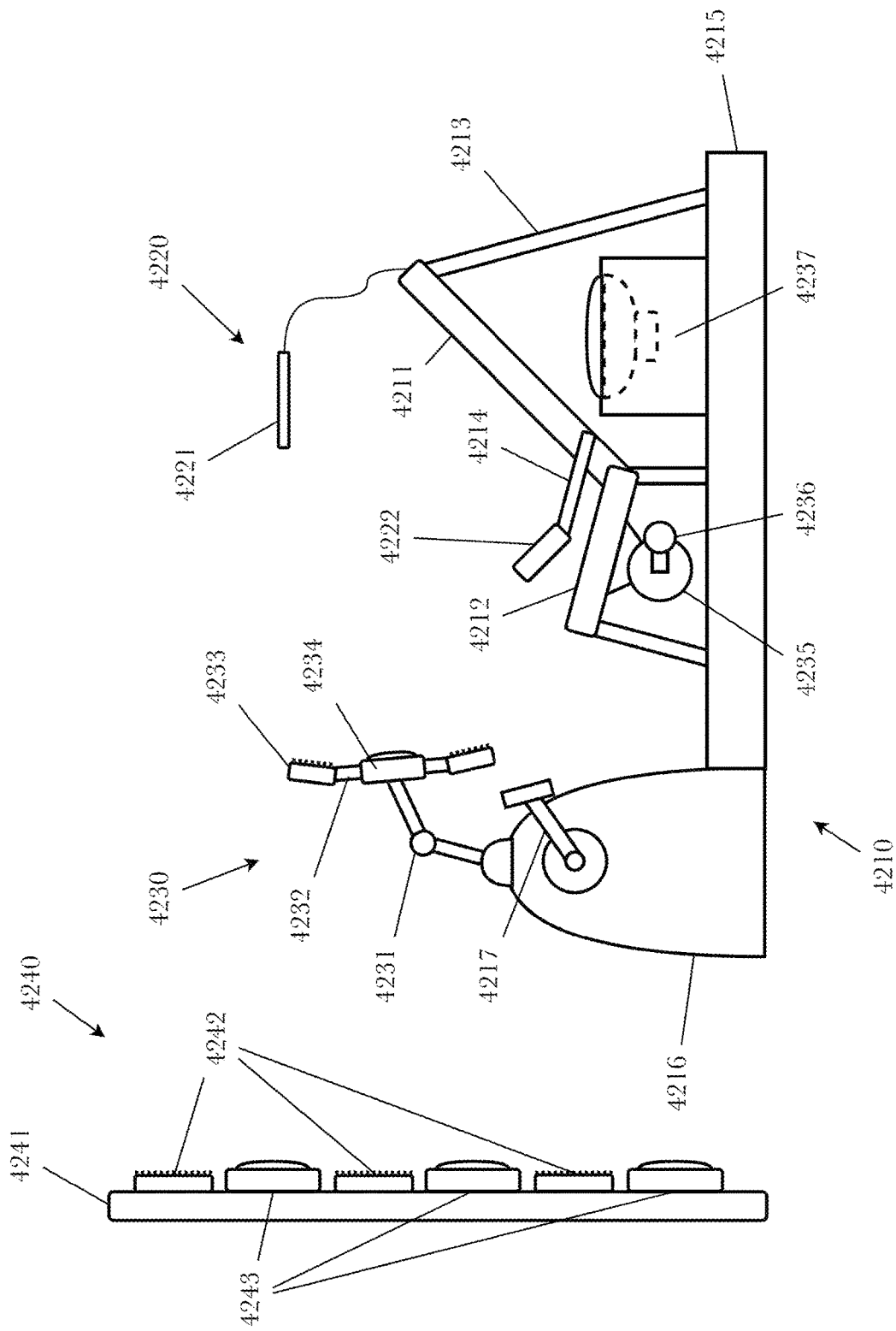
FIG. 42 is a diagram of an exemplary brainwave entrainment therapy system for brainwave entrainment therapy with attention tracking and virtual objects plus external stimulation transducers that allows for multi-modal, multi-intensity treatment.

FIG. 42 is a diagram of an exemplary brainwave entrainment therapy system for brainwave entrainment therapy that allows for multi-modal, multi-intensity therapies. The system of this embodiment comprises a stationary recumbent bicycle 4210, and three different scales of brainwave entrainment stimulators: localized and/or individual stimulation transducers 4220, small area stimulation transducers 4320, and large area stimulation transducers 4240.

The stationary recumbent bicycle 4210 comprises a base 4215, a chair back 4211, a seat 4212, arm rests 4214, a plurality of supports 4213 connecting the chair back 4211 and seat 4212 to the base 4215, a resistance mechanism 4216 allowing for resistance to a pedaling motion of the user, and a pedal system 4217 for the user to pedal in a cycling motion. The stationary recumbent bicycle 4210 thus provides the means for the user to engage in a physical task in the case where dual task stimulation (and/or dual task assessment) is being applied.

The localized and/or individual stimulation transducers 4220 of this embodiment are a headband 4221 with vibratory stimulation and hand grips 4222 which provide electrical stimulation. These provide localized stimulation which can only be perceived by the user, which also makes them individual stimulation transducers (as opposed to the other scales, which can be perceived by others, and which could be used to provide brainwave entrainment to more than one person using the same transducer(s)). The headband 4221 may produce simple vibratory (i.e., tactile) stimulation to the head, or may be configured to produce vibrations at certain locations on the head and at certain intensities so as to be perceptible by the middle and inner ear, which causes the stimulation to be both tactile and auditory in nature. This double stimulation (tactile and auditory) amplifies the effect of a single type of transducer, increasing the efficiency of brainwave entrainment from applications of that transducer.

The small area stimulation transducers 4230 of this embodiment are devices attached to the exercise machine 4210, but not directly attached to or in contact with the user. For example, a console comprising a display 4232, light bars 4233, and speakers 4234 similar to that of the device of FIG. 33 may be used. The console may be attached to the exercise machine using an adjustable arm 4231 that allows for optimal positioning of the console for viewing and/or interaction by the user. Other small area stimulation transducers include a large electric motor 4235 with an offset weight 4236 attached to the seat 4212 that allows for full-body vibratory stimulation to be applied, and a subwoofer 4237 under the chair back 4211 that allows for both audible (regular sound) and inaudible (infrasound) stimulation to be applied. Small area stimulation transducers are particularly useful in situations where direct contact with a user is not desirable, or when multiple users will be using the device sequentially, or when brainwave entrainment will be applied to a small number of users (e.g., those directly in front of the stimulation transducers). The display 4232 may be used to provide brainwave entrainment using virtual objects in conjunction with gamification.

The large area stimulation transducers 4240 of this embodiment are devices that can be used over a large area and potentially a large number of persons such as a room or auditorium. In this embodiment, the large area stimulation transducers are large LED light bars 4242 and large speakers 4243 attached to a wall 4241 of the room in which the stimulation will be applied. The large area stimulators such as the LED light bars 4242 and large speakers 4243 on the wall 4241 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

It is important to note that any type of transducer can be applied at any scale. For example, light stimulation can be configured such that it is seen only by one person (e.g., in glasses or goggles), or is seen by a small number of persons (e.g., a single LED light bar), or is seen by many people (e.g., room lights, stadium lights, etc.). Further, the intensity of stimulation can be largely varied separately from the scale of stimulation. However, depending on the circumstances and application, brainwave entrainment at certain scales and/or intensities may be more useful or effective than at others.

The different scales of stimulation transducers allow for a choice of the level of immersion the user experiences with respect to the brainwave entrainment, and to some degree, the level of intensity of the brainwave entrainment. Immersion is the quality of being surrounded by or absorbed in an experience. Intensity is the magnitude of the experience. They are separate qualities (e.g., a localized electric stimulation can be intense, but not immersive), but there can be an increase in intensity with an increase in scale (for example, if light stimulation comes from all directions, it will tend to be both more immersive and more intense, although the intensity of the lights can be reduced to offset this tendency). For example, a localized, subtle electrical stimulation through electrically-conducting hand grips 4222 provides minimal immersion of the user in the brainwave entrainment. This may be useful, for example, where intense concentration on the dual task stimulation is necessary. Small area stimulation transducers such as the LED light bars 4233 on the screen console are useful for mid-level immersion and mid-level intensity of brainwave entrainment. The LED light bars 4233 cover a small, but significant, area of the user's view, and the speakers 4243 are large enough to provide a substantial auditory stimulus. The large area stimulators such as the LED light bars 4242 and large speakers 4243 on the wall 4241 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

Further, it is important to note that the modalities (types of stimulation), scales, and intensities allows for tremendous flexibility in selecting suitable therapies regimens for different situations. For high-immersion scenarios (e.g., maximum brainwave entrainment with fewer cognitive demands such as listening to music), multiple modalities, scales, and intensities may be used at the same time. For example, while a user is listening to classical music, localized electrical stimulation may be applied to the wrist, small area visual stimulation may be applied using a single LED light bar, and large area tactile stimulation may be applied using subwoofers which produce sounds (infrasounds) which are inaudible to the human ear but can be perceived through the sense of touch (e.g., as oscillating pressure on the torso).

Further, modalities can be chosen to either amplify certain tasks or activities or to supplement them. For amplification, treatment modalities are chosen to include those corresponding to a given task or activity in gamification. As an example, if a user is assigned a game activity wherein the user must follow a moving object on the display with his or her eyes, the object can be flashed at 40 Hz for gamma entrainment therapy. As the user is already focused on the object, the user is focusing more intensely on visual activities (and the brain areas and functions associated with visual activities are stimulated), enhancing the effect of the visual gamma entrainment modality. For supplementation, treatment modalities are chosen to exclude those corresponding to a gamification task. As an example, if game activity assigned to a user is identifying songbirds presented on the display, flashing the birds at 40 Hz (or otherwise changing their colors or visual appearance) may interfere with the identification process. In such circumstances, a non-conflicting modality may be chosen such as flashing of background objects or supplementation with audible entrainment.

FIG. 51 is a block diagram illustrating an exemplary system architecture for extended reality therapy using physical interactivity, according to an embodiment. According to the embodiment, the extended reality therapy system 5100 comprises: a virtual reality (VR) engine 5200 configured to generate an various models which allow for the generation of a shared virtual environment in which two or more users can be immersed and interact with real-world objects mapped to the shared virtual environment; a therapeutic engine 5300 configured to generate a distinct therapeutic layer within the shared virtual environment for each of the two or more users, wherein each distinct therapeutic layer comprises one or more tasks for a user to complete; a plurality of sensors 5140 configured to capture and transmit various types of data to at least the VR engine 5200 and the therapeutic engine 5300; a plurality of transducers 5160 that may be configured to provide various types of stimulation to at least one of the two or more users in the shared virtual environment; a display (e.g., head mounted display) 5155 configured to display the shared virtual environment to the two or more users; and one or more exercise machines 5150 configured to receive and transmit data from extended reality therapy system 5100.

While this particular embodiment of the architecture is illustrated as having all the components collocated, purely for simplicity and ease of description, it should be appreciated that various implementations and arrangements are possible. For example, extended reality therapy system 5100 may be offered as a server which host services such as data capture system 5110, VR engine 5200, and therapeutic engine 5300. It should be further understood that in such an arrangement the extended reality therapy server and its services need not be located on the same machine, or even in the same physical location, wherein the services may be stored and operated on a separate computing device from the computing device operating as the extended reality therapy server. The extended reality therapy system 5100 may also be configured in a cloud-based architecture wherein the system may be spread across one or more computing devices that may be located in the same location (e.g., data center) or distributed across locations (e.g., multiple data centers).

VR engine 5200 constructs and maintains various real-time environmental and tracking models. Real-time environmental models classify geometry, positions, and motions of real-world surfaces and objects. Additionally, VR engine 5200 applies tracking information to generate unified real-time tracking models for each user and any non-participant people in the real-world space.

A plurality of sensors 5140 may be present which are configured to obtain various types of information and transmit that information to at least VR engine 5200 and therapeutic engine 5300. The plurality of sensors includes, but are not limited to, VR display sensors 5141, user-worn sensors 5142 (e.g., body input 802 tracking devices, referring to FIG. 8), environmental sensors 5143, and biometric sensors 5144. Examples of sensors that may be integral to the VR display 5155 device, worn by the user, and/or positioned throughout the real-world space include, but are not limited to, GPS, proximity sensors (e.g., ultrasonic, capacitive, photoelectric, inductive, magnetic, RFID, etc.), motion sensors (e.g., visible light, infrared light, ultrasound, microwave, gyroscopes, radar, accelerometers, inertial sensors, etc.) image sensors, touch sensors, microphones, cameras, etc. Regardless of the source, this sensor data may be provided to a central computing device (e.g., extended reality and therapy system 5100), e.g., local, network based, cloud-based, etc., that manages the shared virtual environment, maps and renders virtual elements to real-world objects and surfaces, and enables the shared interactions between users.

Present in this embodiment is a data capture system 5110 which may be specifically configured embodiment of data capture system 2700 as described above in FIG. 27. Data capture system 5110 is configured to receive a plurality of sensor data from various types of sensors in order to determine a few things such as, the position and movement of the two or more users in a shared real-world space, the physical activity of the two or more users, the cognitive activity of the two or more users, and the position and movement of ancillary components such as controllers, harnesses, transducers, exercise equipment, headsets (e.g., head mounted display [HMD]), and non-participants (e.g., other people in the real-world environment that are not participating in the shared virtual environment). Data capture system 5110 may also provide a data integrator which is configured to convert, calibrate, and integrate data streams from the plurality of sensors 5140, physical activity data capture device 2710 (referring to FIG. 27) and therapeutic engine 5300. The data integrator of data capture system 5110 may also provide sensor fusion functionality to support the generation of the shared virtual environment for two or more users. Data integrator performs a sensor fusion process that integrates the various sensor inputs, applies scene understanding techniques to obtain a semantic understanding of surfaces, objects (e.g., furniture, control devices, exercise equipment, electronics, inert objects, transducer arrays, etc.). In some aspects, the sensors 5140 being managed by data capture system 5110 applies mutually exclusive sets or groups of sensors (e.g., one group sees part of the room and another group sees a different part. In either aspect, data capture system 5110 dynamically manages multiple coordinate systems corresponding to each group of sensors, until the time that they are merged via the sensor fusion process. In a very simplified example of sensor fusion, sensors coupled to the VR display device of all users are used to track and model each user and any other users, non-participants, surfaces, and objects in the shared real-world space.

According to the embodiment, one or more exercise machines 5150 are present and configured to be operated by an extended reality therapy system 5100 user while the user is in the simulated shared virtual environment. In various implementations, users (e.g., patients, athletes, etc.) can perform physical tasks within an extended reality (e.g., augmented reality, virtual reality, etc.) game context presented through the shared virtual environment. For example, a patient on an exercise machine (such as those disclosed in FIG. 12, FIG. 17-19, FIG. 31, FIG. 34, and FIG. 42) can perform coordination exercises within the shared virtual environment by simultaneously using the exercise machine 5150 and performing other tasks (e.g., dual-task stimulation, brainwave entrainment, etc.) in a simulated environment. This type of system design with a shared virtual environment is advantageous in that it allows direct engagement between a therapist (or physician, coach, trainer, etc.) and a patient (e.g., user) within a shared simulated environment.

Another advantage of the extended reality therapy system 5100 is that it allows for physical therapy to be combined with cognitive therapy to form a multifaceted approach to therapeutic engagement within a shared virtual environment. As previously discussed, the extended reality therapy system 5100 supports multiple players (e.g., users) with a shared virtual environment. In various implementations, each player receives brainwave entrainment treatment distinctly, even though the players are all in the same virtual world/game (e.g., shared virtual environment). Thus, each player has shared game experience with tailored therapeutic treatment. This results in a shared reality layer and individual therapeutic layers for each player. These two distinct layers can share information between each other, e.g., therapy layer shares its data so that the shared virtual environment layer can change or react to the user's therapeutic response. Two or more players can coordinate together to perform a joint task within the shared virtual environment, but with each player having a distinct therapeutic treatment. For example, two players are placed into a shared virtual environment where their joint goal is to defend the moon against an alien invasion and are each given a virtual cannon that they can use to combat the alien forces. In this example, the first player may have a therapeutic layer that tracks their heart rate as they use an exercise machine, and if they maintain their heart rate at or above a level determined by an therapist, then the virtual cannon will fire and the first player can assist in the joint task of defending the moon while performing therapy tailored to their physical and cognitive needs. The second player may have a therapeutic layer that performs brainwave entrainment by displaying aliens flashing at certain frequencies to induce gamma waves in the second players brain, and if they maintain focus (determined by eye tracking sensors in a display device) on the flashing alien for a predetermined time period (e.g., 10 seconds, 30 seconds, etc.) as set by a therapist, then the virtual cannon will fire at the flashing alien. In this example, the first player would not see any blinking aliens, as that is distinct to the second player's therapeutic layer.

Extended reality therapy system 5100 can provide more targeted cognitive therapy using extended reality elements that go beyond what is readily possible in the physical world. A shared virtual environment can manipulate the environment to increase brain functions such as recognition, memory, cognition, recall, emotion response, and motor skills. For example, virtual reality technology allows for the creation of Escher environments, impossible colors, and spatial distortions to stimulate reflexes, spatial awareness, perception of object permanence, navigation, etc. The ability to use virtual reality simulations with targeted cognitive regimens implemented as games and virtual activities and to also monitor and capture the results of such regimens can produce useful and relevant data for researchers and data scientists to study. Additionally, such data capturing capabilities can be used in conjunction with machine and/or deep learning techniques to improve both VR engine 5200 and therapeutic engine 5300 capabilities such as, but not limited to, improved environmental modeling and improved cognitive therapy regime design.

According to the embodiment, extended reality therapy system 5100 further comprises a therapeutic engine 5300 configured to provide both physical and cognitive therapy to users of the shared virtual environment by implementing distinct, individualized therapeutic layers for each user within the shared virtual environment. In some embodiments, therapeutic engine 5300 may be configured as a server with a memory and at least one processor. Therapeutic engine 5300 implements a therapy regimen for each user, tracks the progress and response of each user with respect to their therapy regimen, analyzes each user's progress and response to the therapy regimen, and uses this information to update the therapeutic layer of each user as well as send this information to VR engine 5200 which can use the information to update and alter the shared virtual environmental layer based on each users response to the therapy regimen. Therapeutic engine 5300 can receive sensor data from biometric sensors 5144 which can be used to determine a user's progress and response to a virtual therapy regimen.

Also present in the embodiment is a VR databases 5120 which stores relevant information for the creation of the models that support mapping real-world objects, surfaces, and individuals to a virtual space and the implementation of a shared virtual environment. According to various implementations, VR database 5120 may store the following information, VR application software (e.g., VR games, scenarios, and environments), avatar definitions, VR environment definitions, asset/element definitions, and semantic information which support mapping a real-world space to a shared virtual environment. Each of the VR definitions defines a VR environment, which includes a space-time framework, and an instantiation and layout of objects, lights, viewpoints, zones, semantic groups, links or portals to other VR spaces, images, text, audio, haptics, multimedia content, and other virtual elements that are to be used in the shared virtual environment. The space-time framework defines the physical parameters and 3D constraints of the shared virtual environment. Physical parameters such as gravity, friction, and atmosphere govern virtual physics of objects and users navigating the immersive, shared virtual environment, and a temporal clock that relates the inception and passage of time in a virtual environment, relative to other virtual spaces. Physical constraints include bounds such as terrains, horizons, encompassing skies, and can include walls, floors, ceilings, pillars, steps, and other geometry that typically define a static background or virtual set of the shared virtual environment. Asset definitions typically relate to content stored in the external files that are instantiated one or more times within a shared virtual environment. Assets can be 3D objects, shaders, particles, animations, images, video, audio, text, program scripts, or other multimedia content types. Avatar definitions define parameters and characteristics of avatars represented in the shared virtual environment.

Also present in the embodiment is one or more therapy databases 5130 which store relevant information for the creation of therapy regimens and the implementation of individualized therapeutic layers within a shared virtual environment. For example, therapy databases 5130 may comprise information related to, but not limited to, user composite functioning score historical data, demographic data, user range of motion historical data, user movement profile history data, gamma entrainment data, virtual task performance metrics, and neurological function data.

FIG. 52 is a block diagram illustrating an aspect of the extended reality therapy system 5100, a VR engine 5200. In some implementations, VR engine 5200 is offered as a service or microservice that can be accessed via an extended reality therapy server, which may be a specifically configured implementation of the architecture illustrated in FIG. 51.

According to the aspect, VR engine 5200 constructs and maintains real-time environmental models 5210 of shared real-world spaces. Real-time environmental models classify geometry, positions, and motions of real-world surfaces and objects. VR engine 5200 receives real-time tracking information via integrated sensor data 5201 from a plurality of sensors (e.g., VR display sensors 5141, user-worn sensors 5142, environmental sensors 5143, biometric sensors 5144, etc.). VR engine 5200 applies this tracking information to generate and update a real-time environmental model 5120 of a shared real-world space, and objects and surfaces in that space, in which multiple users are participating in a shared virtual environment. Additionally, VR engine 5200 applies the tracking information to generate unified real-time tracking models 5220 for each user and any non-participant people in the real-world space. VR engine 5200 then utilizes the real-time environmental model and the unified real-time tracking models to generate frames of the shared virtual environment corresponding to a real-time field of view of each user. Generation of these frames of the shared virtual environment are constrained by several factors. For example, VR engine 5200 jointly constrains each frame of the shared virtual environment for each user via both the real-time environmental models and the unified real-time tracking models of users. Additionally, virtual element renderer 5230 map and renders virtual elements of the shared virtual environment to real objects in the shared real-world space that can be touched and manipulated by two or more users to provide shared tactile interaction. VR software applications may be obtained from VR database 5120 and used to overlay a developer specific overlay, theme, etc. over the virtualized real-world environment. For example, some VR applications may turn the shared virtual environment into a jungle, space station, time period, or any other possibility based on the VR applications software instructions.

VR engine 5200 may also send environment data 5203 to a therapeutic engine 5300 which can be used to update or augment the distinct therapeutic layer for each user in the shared virtual environment. Likewise, therapeutic engine 5300 can send user response data 5202 to VR engine 5200 which can the update and augment the shared virtual environment based on the user response data.

According to the aspect, VR engine 5200 receives, retrieves, or otherwise obtains a plurality of integrated sensor data 5201 collected from various data sources including, but not limited to, a plurality of sensors 5140, an exercise machine 5150, a display 5155, and therapeutic engine 5300. VR engine 5200 applies the integrated sensor data obtained from the real-world space to construct and maintain a scene object model 5240 (SOM) that dynamically evolves in real-time as users and objects move within the real-world space while interacting with the shared virtual environment. In general, the SOM contains various levels of covering the geometric structure of the scene and the objects within it, semantic information deduced about the objects and people present, and accurate tracking information that can cover people (general position), hand and skeleton tracking, and objects used in the simulation. For example, the SOM may be a hierarchal SOM that represents all relevant persons, objects, and surfaces in the shared real-world space. Scene geometry includes both static and dynamic elements. Static elements may be further modeled and categorized to provide a semantic understanding of both the room layout and the interior objects in the room (or other real-world space). The dynamic elements may be further modeled and categorized to provide semantic understanding of moving or movable objects and people. Some of these objects may be designated as non-tracked, while other objects are designated as tracked. Similarly, people are designated as non-participants and participants (i.e., users). VR engine 5200 performs an application dependent determination about whether to designate particular objects as tracked and non-tracked objects. In general, objects are segmented and classified, and then initially marked as non-tracked. Objects that subsequently move may be marked as tracked. Further, the user of the application (or an administrator such as a therapist, coach, physician, etc.) can select or specify objects or object classifications to be designated as tracked.

Given the tracking, modeling, and semantic information of the real-world embodied by the SOM, the VR engine 5200, via a virtual element renderer 5230, can insert virtual objects in the place of real objects, hide particular objects or people (e.g., render other objects or characters in their place, or simply do not render anything in their place), etc. However, VR engine 5200 may not actually model the entire shared real-world space around the user since it might be disruptive to the overall experience intended to be provided by the shared virtual environment. For example, users using a stair-climber exercise device 5150 may see some virtual surfaces in the place of the stair-climber (e.g., virtual stairs, ladder, boxes, logs, etc.) while other portions of the shared real-world space around the users appears (via the shared virtual environment) as a towering temple in a lush jungle, a spacecraft with a heading for the moon with windows that display a cosmic scene, a sports arena with a crowd chanting, etc.

In some embodiments, VR engine 5200 dynamically scans and models some or all of the shared real-world space around the user. The resulting sensor data is used to construct the SOM and the corresponding semantic understanding of the scene that enables virtual element renderer 5230 to render virtual elements (matching some theme specified by the developer) into the corresponding real-world location of the real-world objects, surfaces, users, and non-participants. For example, in various embodiments, real-time tracking and motion data of users and objects in the shared real-world space is used to capture and model users, objects, and surfaces based on environmental tracking and mapping information received from a plurality of sensors 5140. The sensors used for this purpose can include a combination of head mounted sensors (e.g., coupled to the VR display 5155 device), body worn sensors (e.g., body tracking hardware as described in FIG. 4, gloves, harnesses, vests, etc.), sensors dispersed throughout the shared real-world space, etc. The resulting tacking and environmental information are then applied to capture and map the shared real-world space, track and model each user and other real people (e.g., non-participants), and real objects and surfaces in the shared real-world space. Some or all of this tracking and modeling information is then consolidated and synched in real-time to the rendering of the shared virtual environment being presented to the users.

In some embodiments, a tracking system component of VR engine 5200 maintains a global three-dimensional (3D) coordinate system relative to the shared real-world space. This tracking system component maintains a position value for each user in combination with an orientation value for each user relative to the global coordinate system. Furthermore, in various aspects, the tracking system component also tracks a 3D skeleton model of each user and a 3D hand model of each of the user's hands. Synchronizing this tracking and modeling information into the shared virtual environment enables VR engine 5200 to map and render virtual elements to real-world objects and surfaces that may be touched by users to provide shared tactile feedback or other data output 5204. The aforementioned capability to dynamically manage multiple coordinate systems corresponding to different groups of sensors assists this process.

A VR database 5120 which stores relevant information for the creation of the models that support mapping real-world objects, surfaces, and individuals to a virtual space and the implementation of a shared virtual environment. According to various implementations, VR database 5120 may store the following information, VR application software (e.g., VR games, scenarios, and environments), avatar definitions, VR environment definitions, asset/element definitions, and semantic information which support mapping a real-world space to a shared virtual environment. Each of the VR definitions defines a VR environment, which includes a space-time framework, and an instantiation and layout of objects, lights, viewpoints, zones, semantic groups, links or portals to other VR spaces, images, text, audio, haptics, multimedia content, and other virtual elements that are to be used in the shared virtual environment. The space-time framework defines the physical parameters and 3D constraints of the shared virtual environment. Physical parameters such as gravity, friction, and atmosphere govern virtual physics of objects and users navigating the immersive, shared virtual environment, and a temporal clock that relates the inception and passage of time in a virtual environment, relative to other virtual spaces. Physical constraints include bounds such as terrains, horizons, encompassing skies, and can include walls, floors, ceilings, pillars, steps, and other geometry that typically define a static background or virtual set of the shared virtual environment. Asset definitions typically relate to content stored in the external files that are instantiated one or more times within a shared virtual environment. Assets can be 3D objects, shaders, particles, animations, images, video, audio, text, program scripts, or other multimedia content types. Avatar definitions define parameters and characteristics of avatars represented in the shared virtual environment.

VR engine 5200 may receive, retrieve, or otherwise obtain information stored in VR database 5120 and therapy database 5130 to assist in the above processes. Additionally, VR engine 5200 may also store information into the relevant database as necessitated during normal system operations. For example, a virtual mapping and rendering of real-world space into a shared virtual environment may be saved to VR database 5120 so that when extended reality therapy system 5100 is repeatedly operated in the same location, the stored virtual representation of the real-world space can be retrieved and used as a starting point for the next sessions generation of the shared virtual space.

FIG. 53 is a block diagram illustrating an exemplary aspect of the extended reality therapy system 5100, a therapeutic engine 5300. In some implementations, therapeutic engine 5300 is offered as a service or microservice that can be accessed via an extended reality therapy server, which may be a specifically configured implementation of the architecture illustrated in FIG. 51.

According to the aspect, therapeutic engine 5300 is configured to provide both physical and cognitive therapy to users of the shared virtual environment by implementing distinct, individualized therapeutic layers for each user within the shared virtual environment. Therapeutic engine 5300 implements a therapy regimen for each user, tracks the progress and response of each user with respect to their therapy regimen, analyzes each user's progress and response to the therapy regimen, and uses this information to update the therapeutic layer of each user as well as send this information 5303 to VR engine 5300 which can use the information to update and alter the shared virtual environmental layer based on each users response to the therapy regimen. Therapeutic engine 5300 can receive integrated sensor data 5301 from data capture system 5110 collected from various types of sensors, for example biometric sensors 5144 which can be used to determine a user's progress and response to a virtual therapy regimen by tracking biometrics such as a user's heart rate, blood oxygen levels, blood pressure, etc. Therapeutic engine 5300 may also receive environment data 5302 from VR engine 5200 which can be used to update or augment the distinct therapeutic layer for each user in the shared virtual environment. Likewise, therapeutic engine 5300 can send user response data 5303 to VR engine 5200 which can the update and augment the shared virtual environment based on the user response data. For example, if a user response to a dual-task simulation is that their heart rate has risen too high above a predetermined threshold of safety while riding the stationary bicycle of FIG. 34, then the therapeutic layer would send a signal to the exercise machine 5150 to decrease its resistance and also send a signal 5303 to VR engine 5200 which can alter the shared virtual space to reflect the change in resistance.

According to the aspect, therapeutic engine 5300 may comprise one or more microservices and/or modules that can be leveraged to create and apply distinct therapeutic layers for each user of the shared virtual environment. A brainwave entrainment manager 5310 is present and configured to present virtual objects and environments as visual stimulation transducers. Brainwave entrainment manager 5310 chooses and/or modifies a brainwave routine appropriate for each individual user and for the circumstances. For example, if the therapy regimen controller 5330 input specifies that the overall brainwave entrainment goal is relaxation, the entrainment routine selector (referring to FIG. 40) may select alpha wave entrainment as the primary entrainment therapy, and may choose to apply alpha wave entrainment to a background virtual object, as flashing of background objects will be less intrusive (and possibly more relaxing) to the user than flashing of objects to which the user's attention is directed. The therapy regimen controller 5330 is an administrative interface that allows an administrator (e.g., a physician, therapist, masseuse, or other service provider) to select therapy regimens for application to the user (who may be a patient, client, etc., of the administrator). The therapy regimen controller 5330 may be used, for example, to select a regimen for brainwave entrainment that emphasizes alpha wave stimulation to induce relaxation in an overstimulated user. For more information about therapy regimen controller 5330 and brainwave entrainment manager 5310 refer to FIG. 39 and FIG. 40.

Therapeutic engine 5300 may further comprise a dual-task stimulation manager 5320 which, according to various implementations, is responsible for receiving neurological assessments, each comprising a neurological condition to be treated, and creating therapy regimens to treat the neurological condition. Once a therapy regimen is created, the dual task stimulation manager 5320 assigns dual task stimulation to the individual undergoing treatment comprising a primary task and an associative task. In this case the primary task involves physical movement on an exercise machine 5150, and the associative task involves solving puzzles presented in the shared virtual environment. The exercise machine 5155 provides feedback to the dual task stimulation manager 5320 as to whether the primary task is being performed, and the therapeutic engine 5300 provides feedback 5304 as to whether the associative activity is being performed. While the dual task stimulation is being performed, dual task stimulation manager 5320 sends signals 5304 to the appropriate virtual objects as visual stimulation transducers to operate them according to the appropriate stimulation frequency. For more information about the operation of dual-task stimulation manager refer to FIG. 36.

According to the aspect, therapeutic engine 5300 further comprises a neurological functioning analyzer 5340. Neurological functioning analyzer 5340 evaluates data 5301 from data capture system 5110, the range of motion and performance comparator 2800, and the movement and performance profile analyzer 2900 (referring to FIG. 29 and FIG. 30) to generate a profile of the user's nervous system function as indicated by composite functioning scores which indicate relative ability of an individual in one or more physical and mental functional measurement areas (also referred to herein as "composite functioning scores"). The current composite functioning score analyzer 3001 ingests sensor data related to an individual's movement and performance and calculates a set of current composite functioning scores for that individual based on the sensor data, the range of motion and performance profile, the movement and performance profile, and input from the software 2720 regarding associative activities associated with physical movement data. Theses composite functioning scores may be used by VR engine 5300 to select an appropriate therapy regimen (e.g., physical and/or cognitive therapy) as well as to inform the construction of the individualized therapeutic layer for a user with a given composite functioning score.

Therapeutic engine 5300 may receive, retrieve, or otherwise obtain information stored in VR database 5120 and therapy database 5130 to assist in the above processes. Additionally, therapeutic engine 5300 may also store information into the relevant database as necessitated during normal system operations. For example, a user's selected brainwave entrainment therapy regimen and the results thereof may be stored in a user profile stored in therapy database 5130.

Detailed Description of Exemplary Aspects

Figure 2:
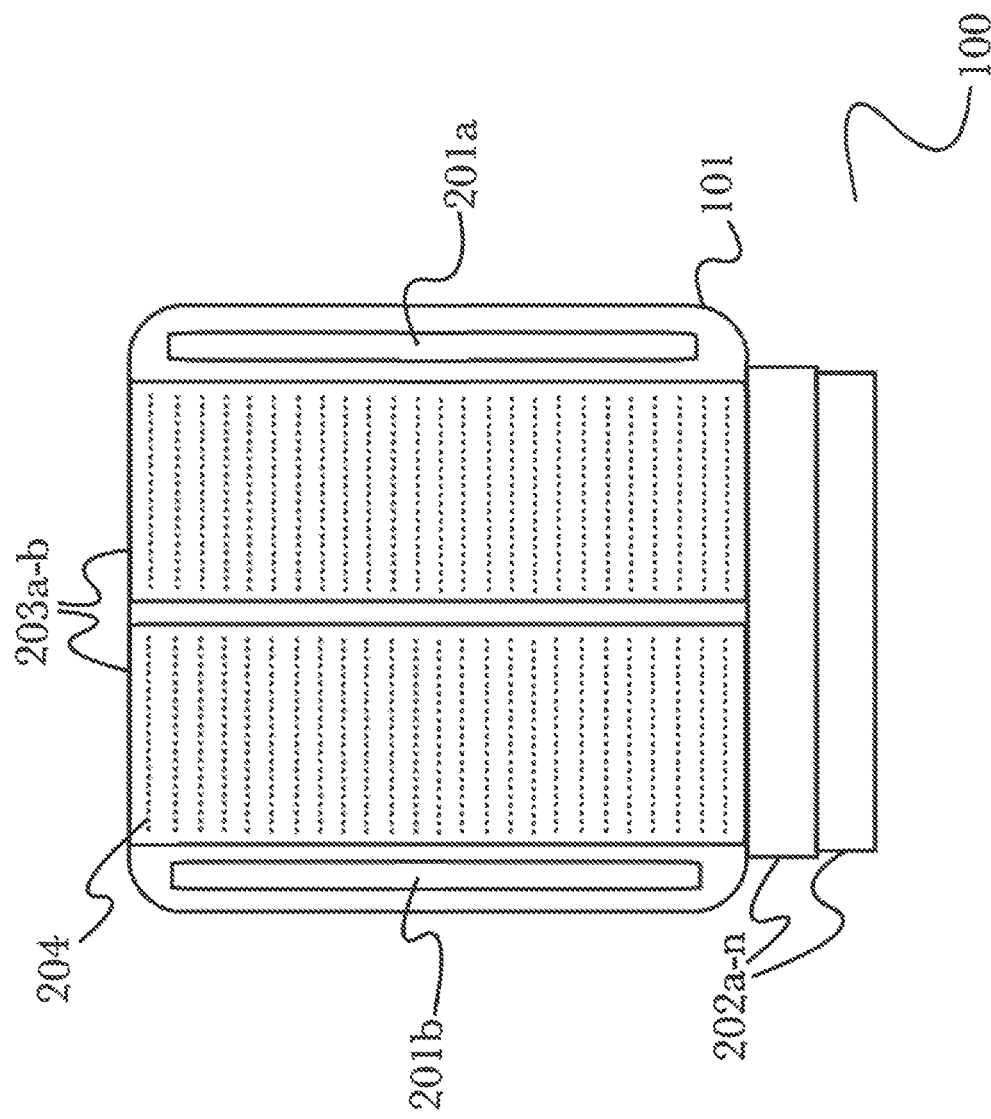
FIG. 2 is a top-down view of an exemplary variable-resistance exercise machine with an embedded or a wireless computing device controlling the interactive software applications of the invention.

FIG. 2 is a top-down view of a variable-resistance exercise machine 100 with wireless communication for smart device control and interactive software applications of the invention. According to the embodiment, exercise machine 100 may comprise a stable base 101 to provide a platform for a user to safely stand or move about upon. Exercise machine 100 may further comprise right 201a and left 201b handrails for a user to brace against or grip during use, to provide a stable support for safety as well as a mounting point for external devices such as a plurality of tethers, as described below with reference to FIG. 3. A plurality of steps 202a-n may be used to provide a user with a safe and easy means to approach or dismount exercise machine 100, as well as a nonmoving "staging area" where a user may stand while they configure operation or wait for exercise machine 100 to start operation. Unlike traditional treadmill machines common in the art, exercise machine 100 may be made with greater width to accommodate a wider range of free movement of a user's entire body (whereas traditional treadmills are designed to best accommodate only a jogging or running posture, with minimal lateral motion), and a plurality of separate moving surfaces 203a-b may be utilized to provide multiple separate surfaces that may move and be controlled independently of one another during use. For example, a user may move each of their legs independently without resistance applied, with separate moving surfaces 203a-b moving freely underfoot as a user applies pressure during their movement. This may provide the illusion of movement to a user while in reality they remain stationary with respect to their surroundings. Another use may be multiple separate moving surfaces 203a-b, with separate speeds of movement or degrees of resistance, so that as a user moves about during use they may experience physical feedback in the form of changing speed or resistance, indicating where they are standing or in what direction they are moving (for example, to orient a user wearing a virtual reality headset, as described below with reference to FIG. 3). Moving surfaces 203a-b may be formed with a texture 204 to increase traction, which may improve user safety and stability during use as well as improve the operation of moving surfaces 203a-b for use in multidirectional movement (as the user's foot is less likely to slide across a surface rather than taking purchase and applying directional pressure to produce movement). Use of multiple, multidirectional moving surfaces 203a-b may also be used in various therapeutic or rehabilitation roles, for example to aid a user in developing balance or range of motion. For example, a user who is recovering from an injury or surgery (such as a joint repair or replacement surgery) may require regular physical therapy during recovery. Use of multidirectional moving surfaces 203a-b along with appropriate guidance from a rehabilitation specialist or physical therapist (or optionally a virtual or remote coach using a software application) may make regular therapy more convenient and accessible to the user, rather than requiring in-home care or regular visits to a clinic. For example, by enabling a therapist or coach to manually vary the movement and resistance of the moving surfaces 203a-b, they can examine a user's ability to overcome resistance to different movements such as at odd angles or across varying range of motion, to examine the user's physical health or ability. By further varying the resistance it becomes possible to assist the user with rehabilitation by providing targeted resistance training to specific movements, positions, or muscle groups to assist in recovery and development of the user's abilities.

Exercise machine 100 may be designed without a control interface commonly utilized by exercise machines in the art, instead being configured with any of a variety of wireless network interfaces such as Wi-Fi or BLUETOOTH™ for connection to a user's smart device, such as a smartphone or tablet computer. When connected, a user may use a software application on their device to configure or direct the operation of exercise machine 100, for example by manually configuring a variety of operation settings such as speed or resistance, or by interacting with a software application that automatically directs the operation of exercise machine 100 without exposing the particular details of operation to a user. Additionally, communication may be bi-directional, with a smart device directing the operation of exercise machine 100 and with exercise machine 100 providing input to a smart device based at least in part on a user's activity or interaction. For example, a user may interact with a game on their smart device, which directs the operation of exercise machine 100 during play as a form of interaction with, and feedback to, the user. For example, in a racing game, exercise machine 100 may alter the resistance of moving surfaces 203a-b as a user's speed changes within the game. In another example, a user may be moving about on moving surfaces 203a-b while playing a simulation or roleplaying game, and their movement may be provided to the connected smart device for use in controlling an in-game character's movement. Another example may be two-way interactive media control, wherein a user may select media such as music for listening on their smart device, and then while using exercise machine 100 their level of exertion (for example, the speed at which they run or jog) may be used to provide input to their smart device for controlling the playback of media. For example, if the user slows down music may be played slowly, distorting the audio unless the user increases their pace. In this manner, exercise machine 100 may be used interchangeably as a control and feedback device or both simultaneously, providing an immersive environment for a wide variety of software applications such as virtual reality, video games, fitness and health applications, or interactive media consumption.

Figure 4:
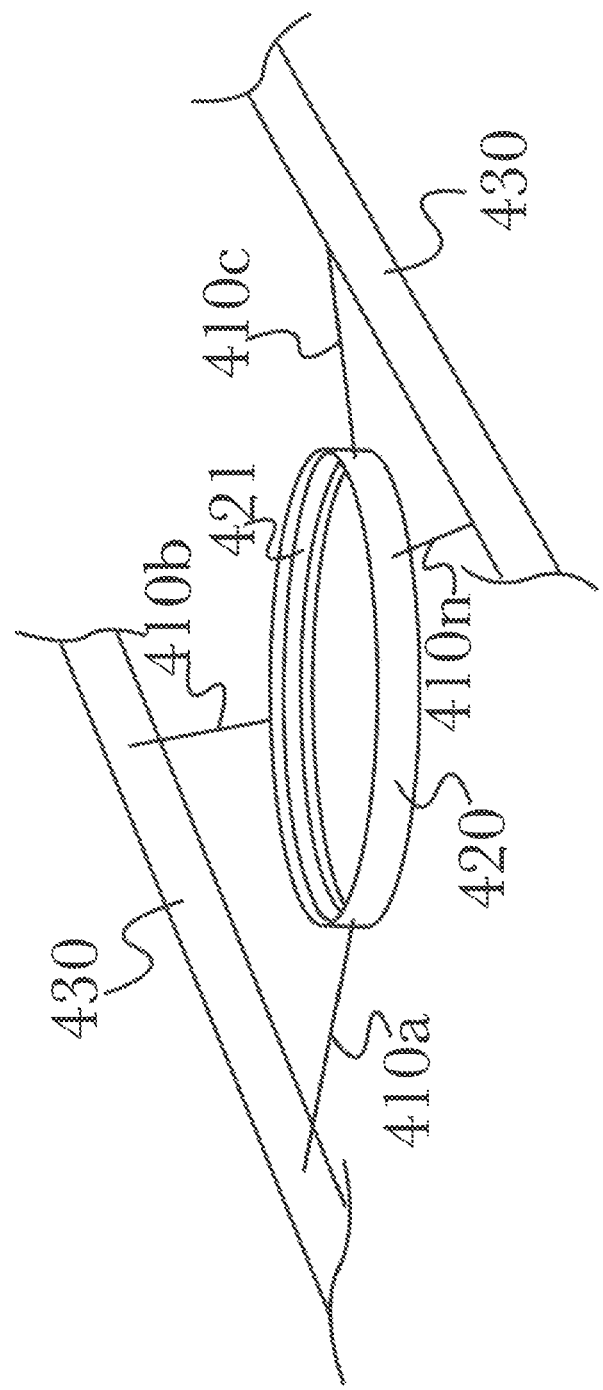
FIG. 4 is a diagram of an exemplary apparatus for natural torso tracking and feedback for electronic interaction, illustrating the use of multiple tethers and a movable torso harness.

FIG. 4 is a diagram of an exemplary hardware arrangement 400 for natural torso tracking and feedback for electronic interaction according to a preferred embodiment of the invention, illustrating the use of multiple tethers 410a-n and a movable torso harness 420. According to the embodiment, a plurality of tethers 410a-n may be affixed or integrally-formed as part of a handle or railing 430, such as handlebars found on exercise equipment such as a treadmill, elliptical trainer, stair-climbing machine, or the like. In alternate arrangements, specifically-designed equipment with integral tethers 410a-n may be used, but it may be appreciated that a modular design with tethers 410a-n that may be affixed and removed freely may be desirable for facilitating use with a variety of fitness equipment or structural elements of a building, according to a user's particular use case or circumstance. Tethers 410a-n may then be affixed or integrally-formed to a torso harness 420, as illustrated in the form of a belt, which may be worn by a user such that movement of their body affects tethers 410a-n and applies stress to them in a variety of manners. It should be appreciated that while a belt design for a torso harness 420 is shown for clarity, a variety of physical arrangements may be used such as including (but not limited to) a vest, a series of harness-like straps similar to climbing or rappelling equipment, a backpack, straps designed to be worn on a user's body underneath or in place of clothing (for example, for use in medical settings for collecting precise data) or a plurality of specially-formed clips or attachment points that may be readily affixed to a user's clothing. Additionally, a torso harness 420 may be constructed with movable parts, for example having an inner belt 421 that permits a user some degree of motion within the harness 420 without restricting their movement. Movement of inner belt 421 (or other movable portions) may be measured in a variety of ways, such as using accelerometers, gyroscopes, or optical sensors, and this data may be used as interaction with software applications in addition to data collected from tethers 410a-n as described below. In some embodiments, a saddle-like surface on which a user may sit may be used, with motion of the saddle-like surface measured as described generally herein.

As a user moves, his or her body naturally shifts position and orientation. These shifts may be detected and measured via tethers 410a-n, for example by detecting patterns of tension or strain on tethers 410a-n to indicate body orientation, or by measuring small changes in strain on tethers 410a-n to determine more precise movements such as body posture while a user is speaking, or specific characteristics of a user's stride or gait. Additionally, through varying the quantity and arrangement of tethers 410a-n, more precise or specialized forms of movement may be detected and measured (such as, for example, using a specific arrangement of multiple tethers connected to a particular area of a user's body to detect extremely small movements for medical diagnosis or fitness coaching). This data may be used as interaction with software applications, such as for virtual reality applications as input for a user to control a character in a game. In such an arrangement, when a user moves, this movement may be translated to an in-game character or avatar to convey a more natural sense of interaction and presence. For example, in a multiplayer roleplaying game, this may be used to facilitate nonverbal communication and recognition between players, as their distinct mannerisms and gestures may be conveyed in the game through detection of natural torso position and movement. In fitness or health applications, this data may be used to track and monitor a user's posture or ergonomic qualities, or to assist in coaching them for specific fitness activities such as holding a pose for yoga, stretching, or proper running form during use with a treadmill. In medical applications, this data may be used to assist in diagnosing injuries or deficiencies that may require attention, such as by detecting anomalies in movement or physiological adaptations to an unrecognized injury (such as when a user subconsciously shifts their weight off an injured foot or knee, without consciously realizing an issue is present).

Through various arrangements of tethers 410a-n and tether sensors (as described below, referring to FIGS. 5-7), it may be possible to enable a variety of immersive ways for a user to interact with software applications, as well as to receive haptic feedback from applications. For example, by detecting rotation, tension, stress, or angle of tethers a user may interact with applications such as virtual reality games or simulations, by using natural body movements and positioning such as leaning, jumping, crouching, kneeling, turning, or shifting their weight in various directions to trigger actions within a software application configured to accept torso tracking input. By applying haptic feedback of varying form and intensity (as is described in greater detail below, referring to FIG. 5), applications may provide physical indication to a user of software events, such as applying tension to resist movement, pulling or tugging on a tether to move or "jerk" a user in a direction, or varying feedback to multiple tethers such as tugging and releasing in varying order or sequence to simulate more complex effects such as (for example, in a gaming use case) explosions, riding in a vehicle, or walking through foliage.

Figure 5:
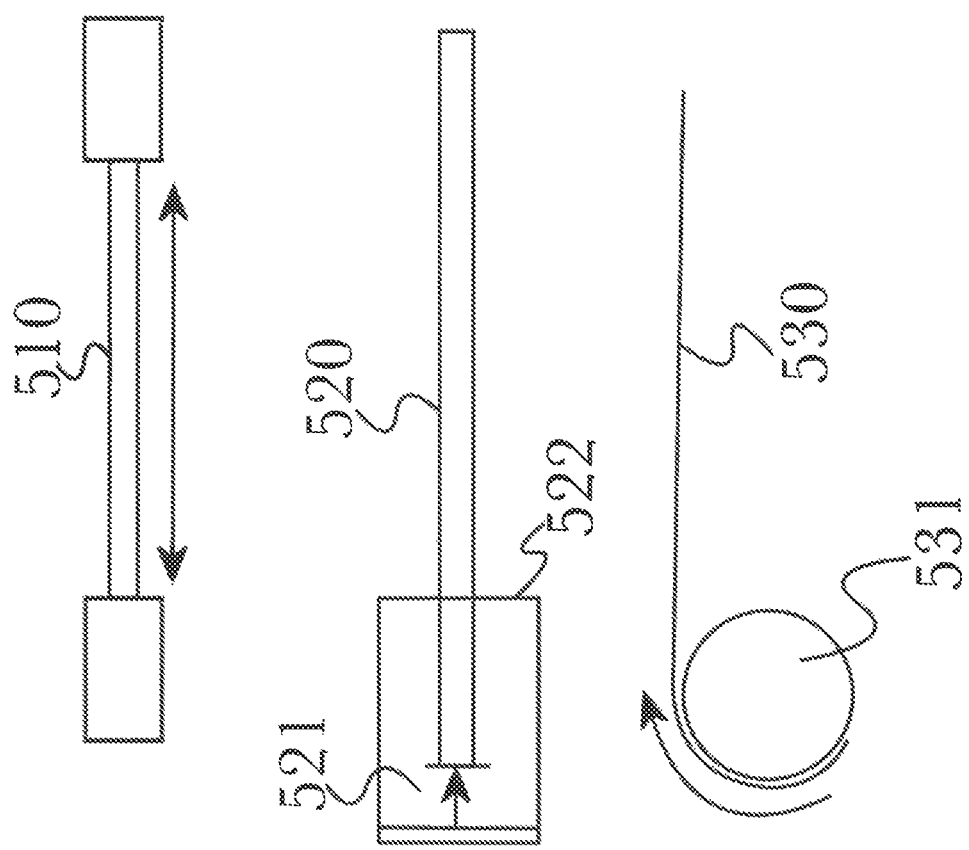
FIG. 5 is a diagram illustrating a variety of alternate tether arrangements.

FIG. 5 is a diagram illustrating a variety of alternate tether arrangements. According to various use cases and hardware arrangements, tethers 410a-n may utilize a variety of purpose-driven designs as illustrated. For example, a "stretchable" tether 510 may be used to measure strain during a user's movement, as the tether 510 is stretched or compressed (for example, using piezoelectric materials and measuring electrical changes). Such an arrangement may be suitable for precise measurements but may lack the mechanical strength or durability for gross movement detection or prolonged use. An alternate construction may utilize a non-deforming tether 520 such as a steel cable or similar non-stretching material. Instead of measuring strain on the tether 520, instead tether 520 may be permitted a degree of movement within an enclosure 522 (for example, an attachment point on a torso harness 420 or handlebar 430), and the position or movement 521 of the tether 520 may be measured such as via optical sensors. In a third exemplary arrangement, a tether 530 may be wound about an axle or pulley 531, and may be let out when force is applied during a user's movement. Rotation of the pulley 531 may be measured, or alternately a tension device such as a coil spring may be utilized (not shown) and the tension or strain on that device may be measured as tether 530 is extended or retracted. In this manner, it may be appreciated that a variety of mechanical means may be used to facilitate tethers and attachments for use in detecting and measuring natural torso position and movement, and it should be appreciated that a variety of additional or alternate hardware arrangements may be utilized according to the embodiments disclosed herein.

Additionally, through the use of various hardware construction it becomes possible to utilize both "passive" tethers that merely measure movement or strain, as well as "active" tethers that may apply resistance or movement to provide haptic feedback to a user. For example, in an arrangement utilizing a coiled spring or pulley 531, the spring or pulley 531 may be wound to retract a tether and direct or impede a user's movement as desired. In this manner, various new forms of feedback-based interaction become possible, and in virtual reality use cases user engagement and immersion are increased through more natural physical feedback during their interaction.

By applying various forms and intensities of feedback using various tether arrangements, a variety of feedback types may be used to provide haptic output to a user in response to software events. For example, tension on a tether may be used to simulate restrained movement such as wading through water or dense foliage, walking up an inclined surface, magnetic or gravitational forces, or other forms of physical resistance or impedance that may be simulated through directional or non-directional tension. Tugging, retracting, or pulling on a tether may be used to simulate sudden forces such as recoil from gunfire, explosions, being grabbed or struck by a software entity such as an object or character, deploying a parachute, bungee jumping, sliding or falling, or other momentary forces or events that may be conveyed with a tugging or pulling sensation. By utilizing various patterns of haptic feedback, more complex events may be communicated to a user, such as riding on horseback or in a vehicle, standing on the deck of a ship at sea, turbulence in an aircraft, weather, or other virtual events that may be represented using haptic feedback. In this manner, virtual environments and events may be made more immersive and tangible for a user, both by enabling a user to interact using natural body movements and positioning, as well as by providing haptic feedback in a manner that feels natural and expected to the user. For example, if a user is controlling a character in a gaming application through a first-person viewpoint, it would seem natural that when their character is struck there would be a physical sensation corresponding to the event; however, this is not possible with traditional interaction devices, detracting from any sense of immersion or realism for the user. By providing this physical sensation alongside the virtual event, the experience becomes more engaging and users are encouraged to interact more naturally as their actions results in natural and believable feedback, meeting their subconscious expectations and avoiding excessive "immersion-breaking" moments, which in turn reduces the likelihood of users adopting unusual behaviors or unhealthy posture as a result of adapting to limited interaction schema.

Haptic feedback may be provided to notify a user of non-gaming events, such as for desktop notifications for email or application updates, or to provide feedback on their posture for use in fitness or health coaching. For example, a user may be encouraged to maintain a particular stance, pose, or posture while working or for a set length of time (for example, for a yoga exercise application), and if their posture deviates from an acceptable range, feedback is provided to remind them to adjust their posture. This may be used in sports, fitness, health, or ergonomic applications that need not utilize other aspects of virtual reality and may operate as traditional software applications on nonspecialized computing hardware. For example, a user at their desk may use an ergonomic training application that monitors their body posture throughout the work day and provides haptic reminders to correct poor posture as it is detected, helping the user to maintain a healthy working posture to reduce fatigue or injuries due to poor posture (for example, repetitive-stress injuries that may be linked to poor posture while working at a computer).

Figure 6:
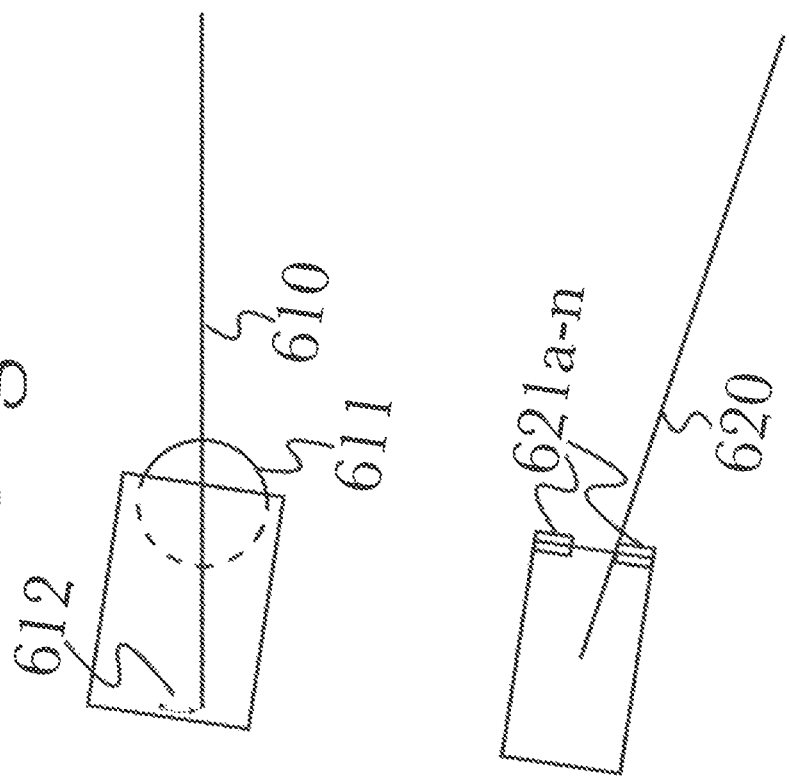
FIG. 6 is a diagram of an additional exemplary apparatus for natural torso tracking and feedback for electronic interaction, illustrating the use of angle sensors to detect angled movement of tethers.

FIG. 6 is a diagram of an additional exemplary hardware arrangement 600 for natural torso tracking and feedback for electronic interaction according to a preferred embodiment of the invention, illustrating the use of angle sensors 612, 621*a*-*n* to detect angled movement of a tether 620. According to one exemplary arrangement, a tether 610 may be affixed to or passed through a rotating joint such as a ball bearing 611 or similar, to permit free angular movement. During movement, the angular movement or deflection 612 of a protruding bar, rod, or tether segment 613 may be measured (for example, using optical, magnetic, or other sensors) to determine the corresponding angle of tether 610. In this manner, precise angle measurements may be collected without impeding range of motion or introducing unnecessary mechanical complexity.

In an alternate hardware arrangement, the use of angle sensors 621*a*-*n* enables tracking of a vertical angle of a tether 620, to detect and optionally measure vertical movement or orientation of a user's torso. When tether 620 contacts a sensor 621*a*-*n*, this may be registered and used to detect a general vertical movement (that is, whether the tether is angled up or down). For more precise measurements, the specific hardware construction of a sensor 621*a*-*n* may be varied, for example using a pressure-sensing switch to detect how much force is applied and use this measurement to determine the corresponding angle (as may be possible given a tether 620 of known construction). It should be appreciated that various combinations of hardware may be used to provide a desired method or degree of angle detection or measurement, for example using a conductive tether 620 and a capacitive sensor 621*a*-*n* to detect contact, or using a mechanical or rubber-dome switch (as are commonly used in keyboard construction) to detect physical contact without a conductive tether 620.

The use of angle detection or measurement may expand interaction possibilities to encompass more detailed and natural movements of a user's body. For example, if a user crouches, then all tethers 410*a*-*n* may detect a downward angle simultaneously. Additionally, data precision or availability may be enhanced by combining input from multiple available sensors when possible (for example, utilizing adaptive software to collect data from any sensors that it detects, without requiring specific sensor types for operation), for example by combining data from tethers 410*a*-*n* and hardware sensors such as an accelerometer or gyroscope, enabling multiple methods of achieving similar or varied types or precision levels of position or movement detection. Similarly, when a user jumps then all tethers may detect an upward angle simultaneously. However, if a user leans in one direction, it may be appreciated that not all tethers 410*a*-*n* will detect the same angle. For example, tethers 410*a*-*n* in the direction the user is leaning may detect a downward angle, while those on the opposite side would detect an upward angle (due to the orientation of the user's torso and thus a worn torso harness 420). In this manner, more precise torso interaction may be facilitated through improved detection and recognition of orientation and movement. Additionally, it may be appreciated that sensors 621*a-n* may be utilized for other angle measurements, such as to detect horizontal angle. For example, if a user is wearing a non-rotating torso harness 420, when they twist their body, a similar stress may be applied to all attached tethers 410*a-n*. Without angle detection the precise nature of this movement will be vague, but with horizontal angle detection it becomes possible to recognize that all tethers 410*a-n* are being strained in a similar direction (for example, in a clockwise pattern when viewed from above, as a user might view tethers 410*a-n* during use), and therefore interpret the interaction as a twisting motion (rather than, for example, a user squatting or kneeling, which might apply a similar stress to the tethers 410*a-n* but would have different angle measurements).

Figure 7:
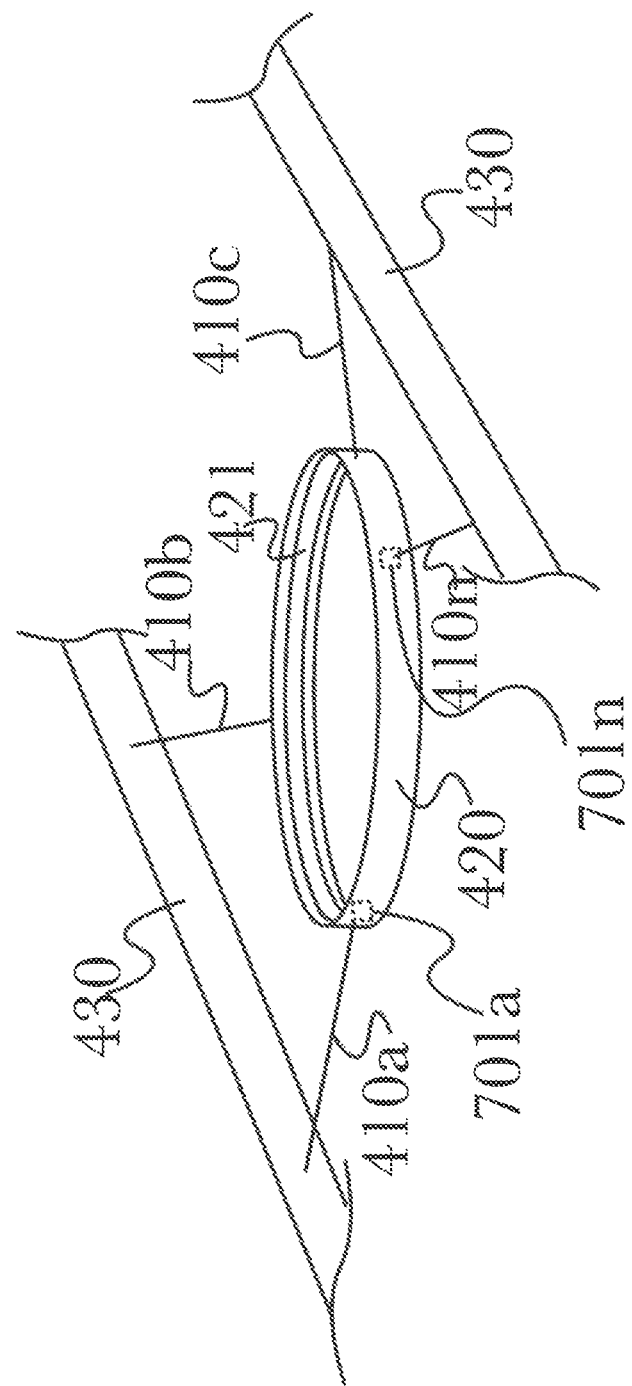
FIG. 7 is a diagram illustrating an exemplary apparatus for natural torso tracking and feedback for electronic interaction, illustrating the use of multiple tethers and a movable torso harness comprising a plurality of angle sensors positioned within the movable torso harness.

FIG. 7 is a diagram illustrating an exemplary hardware arrangement of an apparatus for natural torso tracking and feedback for electronic interaction according to a preferred embodiment of the invention, illustrating the use of multiple tethers 410*a-n* and a movable torso harness 420 comprising a plurality of angle sensors 701*a-n* positioned within the movable torso harness 420. According to the embodiment, a plurality of tethers 410*a-n* may be affixed or integrally-formed as part of a handle or railing 430, such as handlebars found on exercise equipment such as a treadmill, elliptical trainer, stair-climbing machine, or the like. In alternate arrangements, specifically-designed equipment with affixed or integral tethers 410*a-n* may be used, but it may be appreciated that a modular design with tethers 410*a-n* that may be affixed and removed freely may be desirable for facilitating use with a variety of fitness equipment or structural elements of a building, according to a user's particular use case or circumstance as well as weight-holding strength of the tethers. Tethers 410*a-n* may then be affixed or integrally-formed to angle sensors 701*a-n* placed within or integrally-formed as a component of torso harness 420 (as illustrated in the form of a belt) that may be worn by a user such that movement of their body affects tethers 410*a-n* and applies detectable or measurable stress to tethers 410*a-n* and angular motion to angle sensors 701*a-n*. In this manner, it may be appreciated that angle sensors 701*a-n* may be utilized as integral or removable components of a torso harness 420, as an alternative arrangement to utilizing angle sensors 701*a-n* placed or formed within railings 430 or other equipment components connected to distal ends of tethers 410*a-n* (with respect to the user's torso). According to various embodiments, sensors may be placed optionally on a belt, vest, harness, or saddle-like surface or at attachment points on safety railings, or indeed both.

Figure 9:
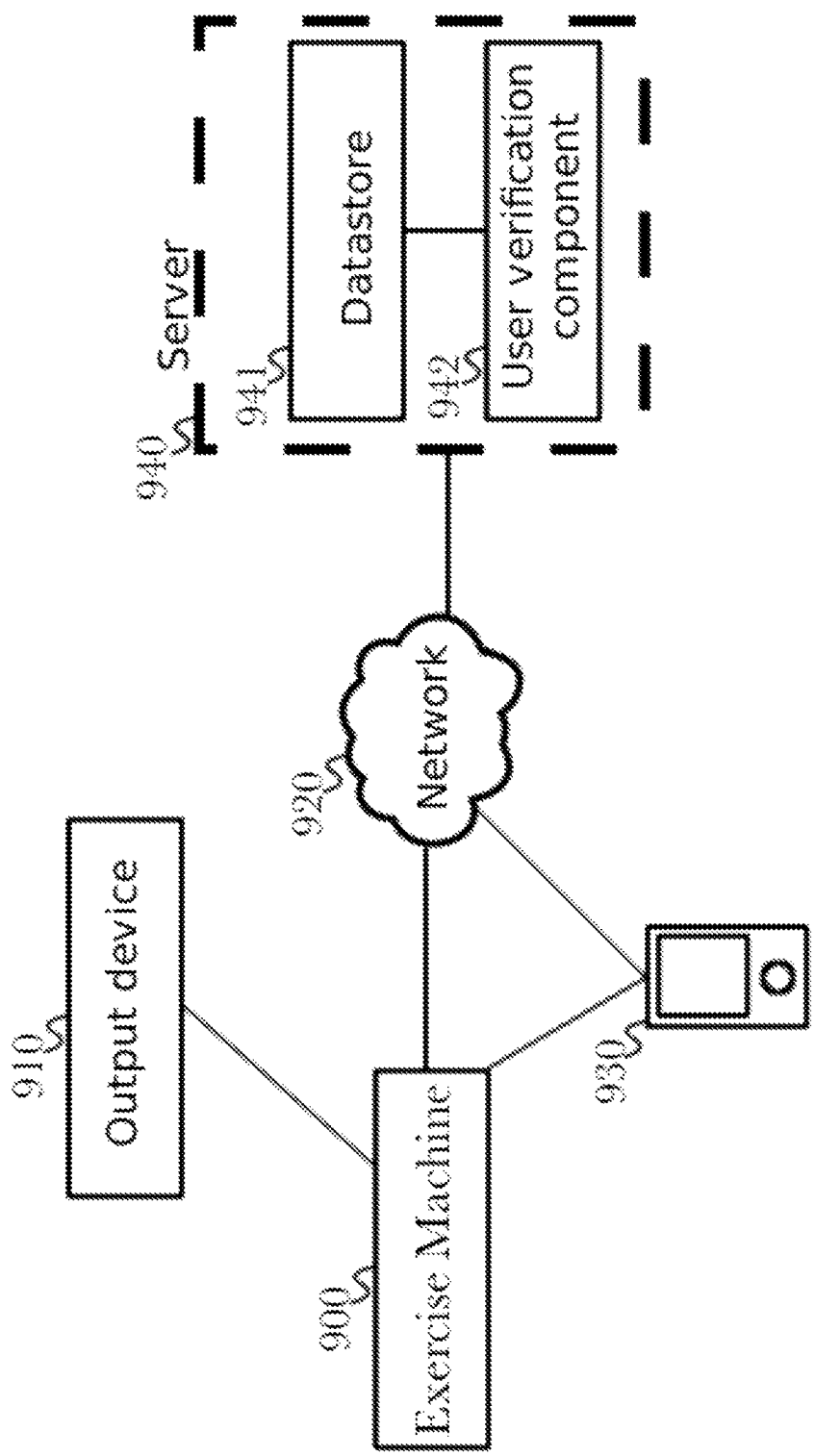
FIG. 9 is a block 1922 diagram of an exemplary system architecture for a stationary exercise bicycle being connected over local connections to a smartphone, an output device other than a phone, and a server over a network, according to an aspect.

FIG. 9 is a block diagram of an exemplary system architecture 900 of an exercise machine 100 being connected over local connections to a smartphone or computing device 930, an output device other than a phone 910, and a server over a network 940. An exercise machine 100 may connect over a network 920, which may be the Internet, a local area connection, or some other network used for digital communication between devices, to a server 940. Such connection may allow for two-way communication between a server 940 and an exercise machine 800. An exercise machine 100 may also be connected over a network 920 to a smartphone or computing device 930, or may be connected directly to a smartphone or computing device 930 either physically or wirelessly such as with Bluetooth connections. An exercise machine 100 also may be connected to an output device 910 which may display graphical output from software executed on an exercise machine 100, including Mixed or virtual reality software, and this device may be different from a smartphone or computing device 930 or in some implementations may in fact be a smartphone or computing device 930. A remote server 940 may contain a data store 941, and a user verification component 942, which may contain typical components in the art used for verifying a user's identity from a phone connection or device connection, such as device ID from a smartphone or computing device or logging in with a user's social media account.

Figure 10:
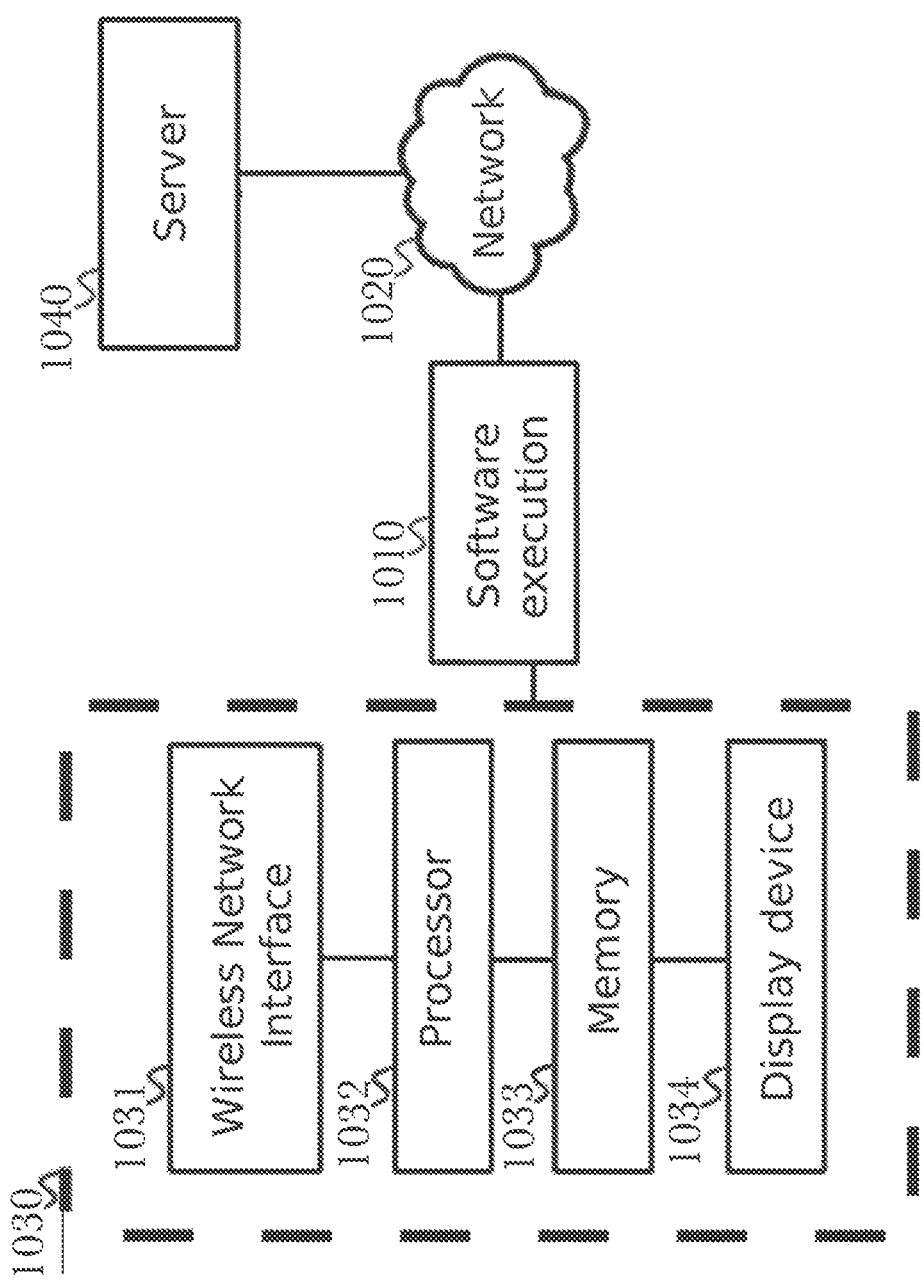
FIG. 10 is a diagram of an exemplary hardware arrangement of a smart phone or computing device running a user identification component and communicating over a network, according to an aspect.

FIG. 10 is a diagram of an exemplary hardware arrangement of a smart phone or computing device 1030 executing software 1010 and communicating over a network 1020. In an exemplary smart phone or computing device 1030, key components include a wireless network interface 1031, which may allow connection to one or a variety of wireless networks including Wi-Fi and Bluetooth; a processor 1032, which is capable of communicating with other physical hardware components in the computing device 1030 and running instructions and software as needed; system memory 1033, which stores temporary instructions or data in volatile physical memory for recall by the system processor 1032 during software execution; and a display device 1034, such as a Liquid Crystal Display (LCD) screen or similar, with which a user may visually comprehend what the computing device 1030 is doing and how to interact with it. It may or may not be a touch enabled display, and there may be more components in a computing device 1030, beyond what are crucially necessary to operate such a device at all. Software 1010 operating on a processor 1033 may include a mixed or virtual reality application, a user verification system, or other software which may communicate with a network-enabled server 1040 and exercise machine 100 software for the purposes of enhanced mixed or virtual reality.

Figure 11:
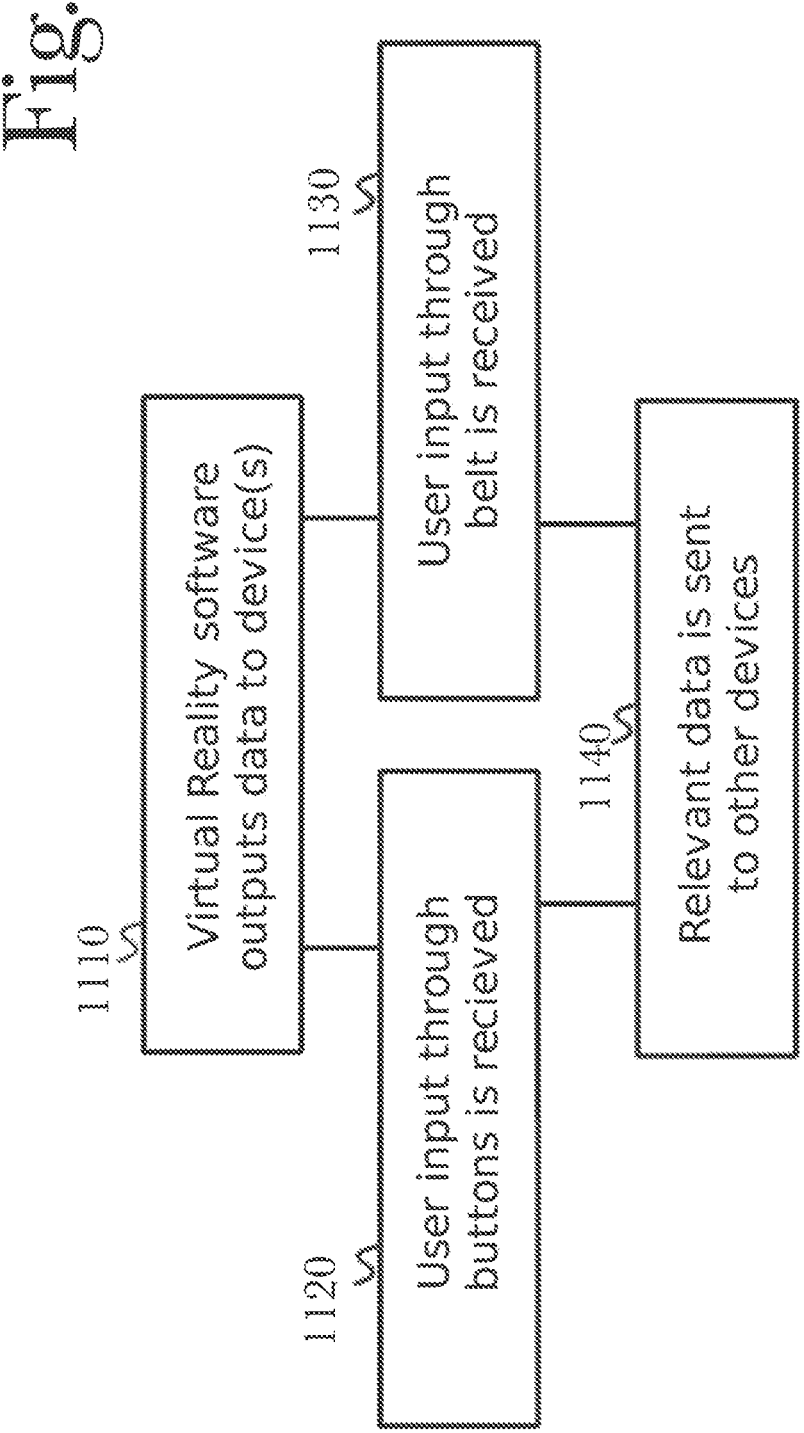
FIG. 11 is a block diagram of a method of mixed or virtual reality software operating to receive input through different sources, and send output to devices, according to an aspect.

FIG. 11 is a block diagram of a method of mixed or virtual reality software operating to receive input through different sources and send output to devices. Mixed or virtual reality software which may be run on a phone or computing device 1030 or another device, outputs data to a visual device for the purpose of graphically showing a user what they are doing in the software 1110. Such display may be a phone display 1034, or a separate display device such as a screen built into an exercise machine 100 or connected some other way to the system, or both display devices. During software execution, user input may be received either through buttons 1130 on the exercise machine 100, 1120, or through input from a belt-like harness 420, such as user orientation or movements. Such received data may be sent 1140 to either a mobile smart phone or computing device 1030, or to a server 1040 over a network 1020, or both, for processing, storage, or both. Data may be stored on a server with a data store device 1041 and may be processed for numerous uses including user verification with a user verification component 1042. Data may be processed either by software running on an exercise machine 100, a smart phone or computing device 1030, or some other connected device which may be running mixed or virtual reality software, when input is received from a user using either buttons on an exercise machine 100, a belt-like harness 420, or both, and optionally using hardware features of an exercise machine 100 such as handlebars, pedals, or other features in mixed or virtual reality software for tasks such as representing movement in a simulation.

Figure 17:
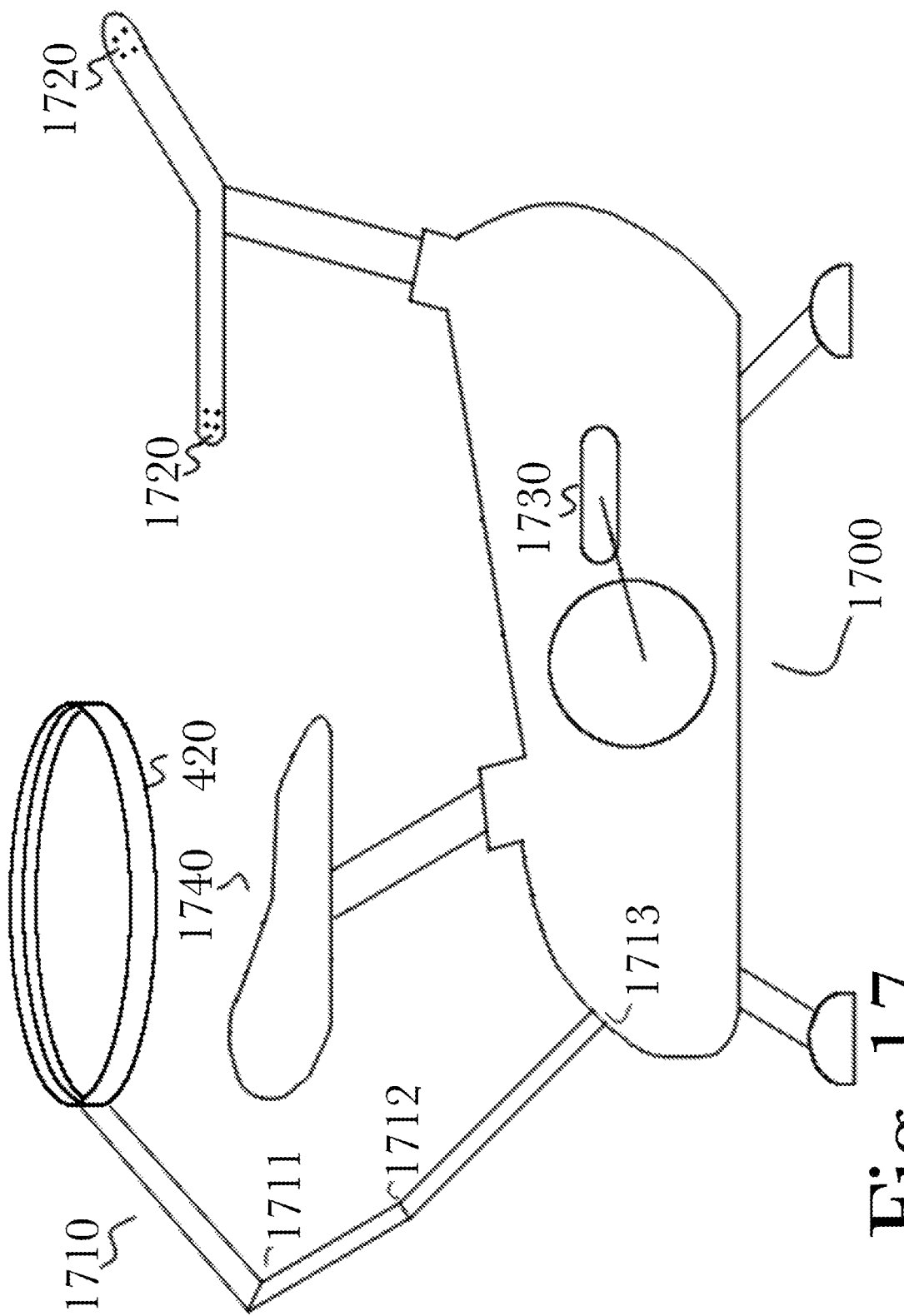
FIG. 17 is a block diagram of an exemplary virtual reality or mixed reality enhanced exercise machine, illustrating the use of a stationary bicycle with hand controls on the handles, and a belt-like harness attachment.

FIG. 17 is a block diagram of an exemplary virtual reality or mixed reality enhanced exercise machine, illustrating the use of a stationary bicycle 1700 with hand controls on the handles 1720, and a belt-like harness attachment 420. A stationary exercise bicycle device 1700, which may be of any particular design including a reclining, sitting, or even unicycle-like design, possesses two pedals 1730 as is common for stationary exercise bicycles of all designs. On handlebars of a stationary exercise bicycle may exist buttons and controls 1720 for interacting with a virtual reality or mixed reality augmented piece of software, allowing a user to press buttons in addition to or instead of pedaling, to interact with the software. A belt-like harness attachment 420 is attached via a mechanical arm 1710 to a stationary exercise bicycle 1700, which may monitor motion and movements from a user during the execution of virtual reality software. A mechanical arm 1710 may have an outer shell composed of any material, the composition of which is not claimed, but must have hinges 1711, 1712, 1713 which allow for dynamic movement in any position a user may find themselves in, and angular sensors inside of the arm at the hinge-points 1711, 1712, 1713 for measuring the movement in the joints and therefore movement of the user. A stationary bicycle device 1700 may also have a pressure sensor in a seat 1740, the sensor itself being of no particularly novel design necessarily, to measure pressure from a user and placement of said pressure, to detect movements such as leaning or sitting lop-sided rather than sitting evenly on the seat.

Figure 18:
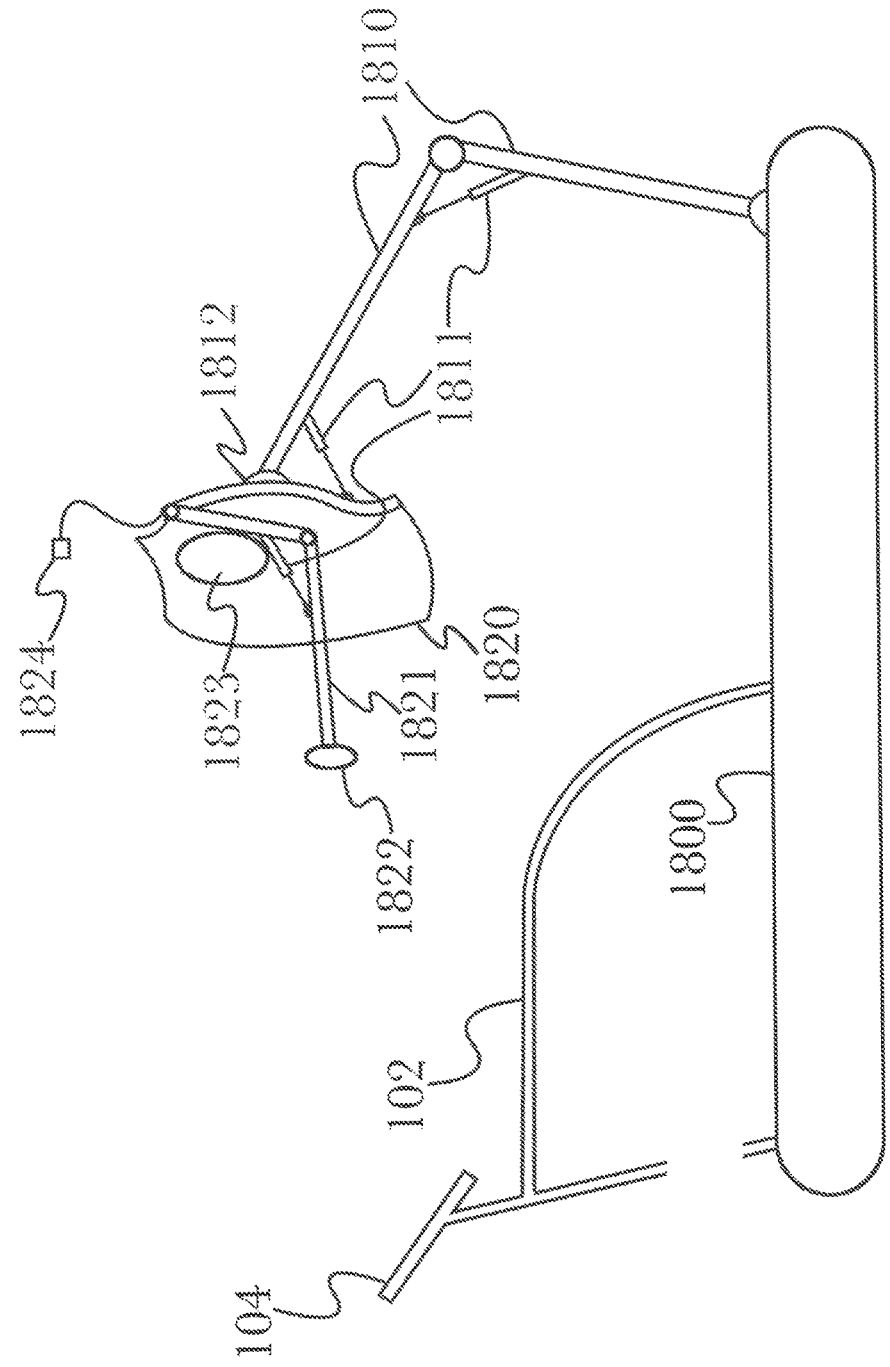
FIG. 18 is a diagram of another exemplary virtual reality or mixed reality enhanced exercise machine, illustrating the use of a treadmill exercise machine with a vest-type harness with a plurality of pistons to provide a hardware-based torso joystick with full-body tracking.

FIG. 18 is a diagram of another exemplary virtual reality or mixed reality enhanced exercise machine, illustrating the use of a treadmill exercise machine 100, 1800 a vest-type harness 1820 with a plurality of pistons 1811 to provide a hardware-based torso joystick with full-body tracking. According to this embodiment, a treadmill or other exercise machine 100, 1800 may comprise a plurality of rigid side tails 102 for a user to grip for support as needed during use (for example, as a balance aid or to assist getting on the machine and setting up other equipment properly) as well as a rigid stand or mount 104 for a user's smartphone or other computing device, that may be used to operate a virtual reality or mixed reality software application. Exercise machine 100, 1800 may further comprise a jointed arm 1810 or similar assembly that may be integrally-formed or removably affixed to or installed upon exercise machine 100, 1800. Arm 1810 may utilize a plurality of pistons 1811 to provide for movement during use in order to follow the movements of a user's body, as well as to provide tension or resistance to motion when appropriate (for example, to resist a user's movements or to provide feedback) and motion detection of a user's movement during use, according to various aspects described previously (referring to FIGS. 3-7, for example) by measuring movement of a piston 1811 or arm 1810 and optionally applying tension or resistance to piston 1811 to retard movement of arm 1810 and constrain user movement or simulate specific forms of physical feedback. For example, if a user is moving an avatar in a virtual reality software application, when the avatar encounters an obstacle such as another avatar, object, or part of the environment, resistance may be applied to piston 1811 to prevent the user from moving further, so that their avatar is effectively prevented from moving through the obstacle and thereby facilitating the immersive experience of a solid object in a virtual environment. Additional arms may be used for a user's limbs 1921 and may incorporate straps 1922 to be affix about a user's arm, wrist, or other body part, to incorporate more detailed movement tracking of a user's arms and/or legs rather than just torso-based tracking. A vest-type harness 1920 may be used in place of a belt 420, to allow for more natural movement or to provide greater area upon which to affix additional arms 1821, pistons 1811, or any of a variety of sensors, for example such as accelerometers 1822 or gyroscopes 1823 for detecting body orientation (not all optional sensors are shown for the sake of clarity). For example, a vest 1820 may have integrated feedback actuators 1812 for use in first-person software applications to simulate impacts or recoil, or it may incorporate heating or cooling elements to simulate different virtual environments while worn. Additionally, vest 1820 may incorporate electrical connectors 1824 for various peripheral devices such as controllers 305*a*-*b* or a headset 302, reducing the risk of tangles or injury by keeping cables short and close to the user so they cannot cause issues during movement or exercise.

Figure 19:
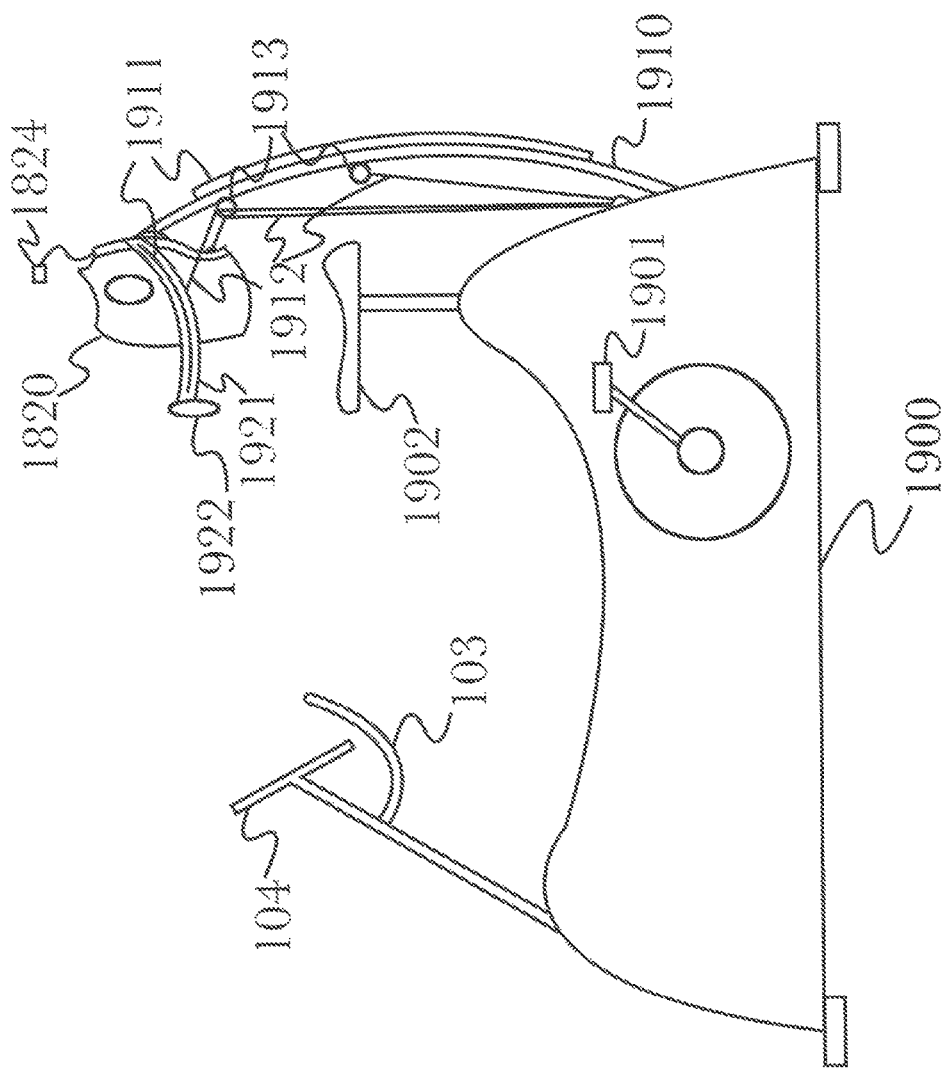
FIG. 19 is a diagram of another exemplary virtual reality or mixed reality enhanced exercise machine, illustrating the use of a stationary bicycle with a vest-type harness with a plurality of strain sensors and tethers.

FIG. 19 is a diagram of another exemplary virtual reality or mixed reality enhanced exercise machine, illustrating the use of a stationary bicycle 1900. This present application is a continuation-in-part of Ser. No. 16/176,511, titled "VIRTUAL REALITY AND MIXED REALITY ENHANCED EXERCISE MACHINE", and filed on Oct. 31, 2018, which with a vest-type harness 1820 with a plurality of strain sensors 1911 and tethers 1912, according to an aspect of the invention. According to this embodiment, rather than a jointed arm 1810 and pistons 1811, a solid flexible arm 1910 may be used to detect user movement while positioned on a seat 1902 to use exercise machine 100, for example while the user is seated to use pedals 1901 on a stationary bike or elliptical training machine. Through a plurality of strain gauges 1911 that detect the flexion or extension of the solid arm. Tethers 1912 may be used for either movement tracking or providing feedback to a user, or both, and may optionally be connected or routed through joints or interconnects 1913 to allow for a greater variety of attachment options as well more precise feedback (for example, by enabling multiple angles from which a tether 1912 may apply force, to precisely simulate different effects). Additional arms may be used for a user's limbs 1921 and may incorporate straps 1922 to be affix about a user's arm, wrist, or other body part, to incorporate more detailed movement tracking of a user's arms and/or legs rather than just torso-based tracking. Additional arms 1921 may also incorporate additional tethers 1912 and strain sensors 1911 to track movement and apply feedback to specific body parts during use, further increasing precision and user immersion. A vest-type harness 1820 may be used in place of a belt 420, to allow for more natural movement or to provide greater area upon which to affix additional arms 1921, tether 1912, or any of a variety of sensors, for example such as accelerometers or gyroscopes for detecting body orientation (not all optional sensors are shown for the sake of clarity). For example, a vest 1820 may have integrated feedback actuators for use in first-person software applications to simulate impacts or recoil, or it may incorporate heating or cooling elements to simulate different virtual environments while worn. Additionally, vest 1820 may incorporate electrical connectors 1914 for various peripheral devices such as controllers 305*a*-*b* or a headset 302, reducing the risk of tangles or injury by keeping cables short and close to the user so they cannot cause issues during movement or exercise.

Figure 20:
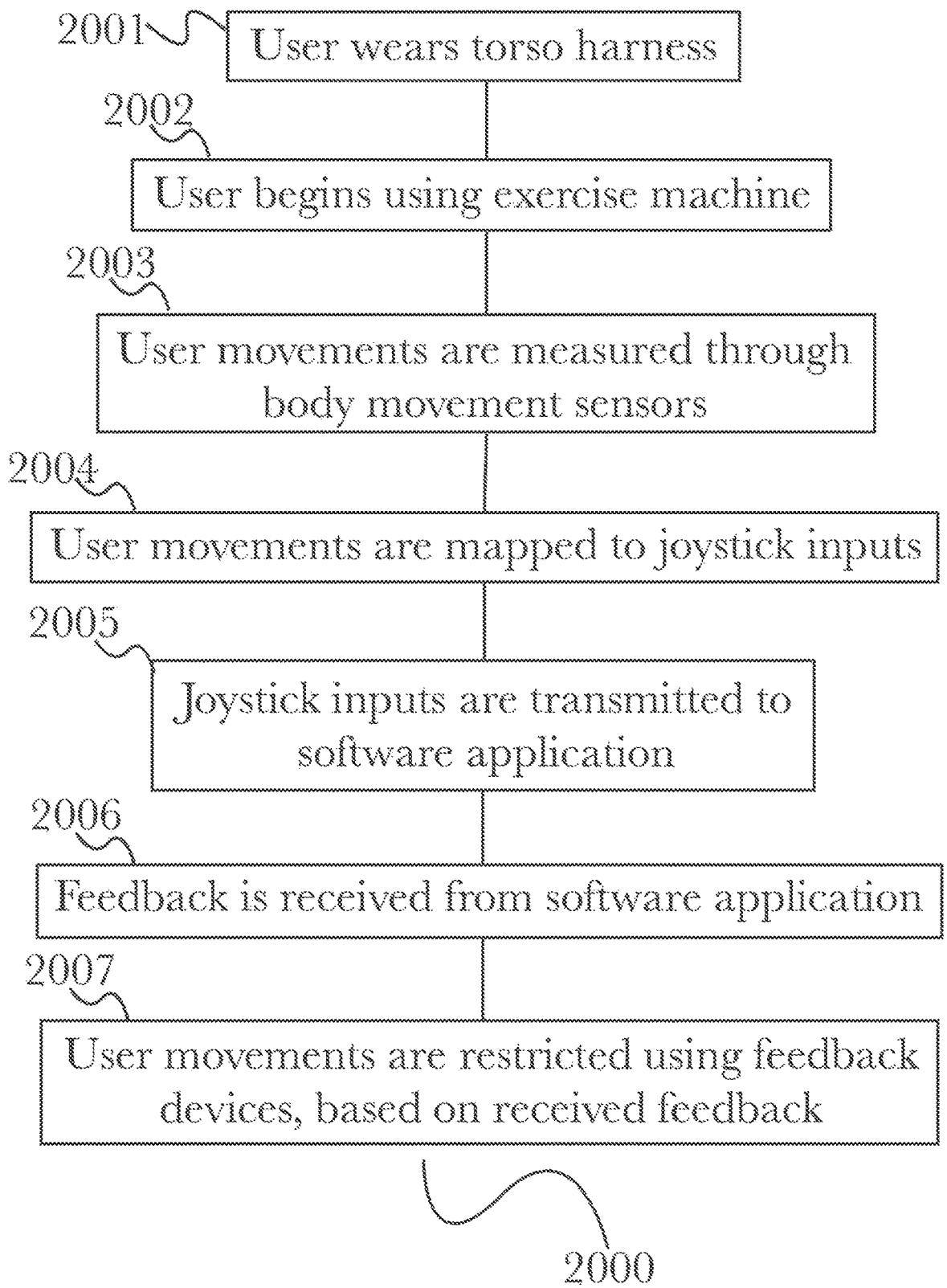
FIG. 20 is a flow diagram illustrating an exemplary method for operating a virtual and mixed-reality enhanced exercise machine.

FIG. 20 is a flow diagram illustrating an exemplary method 2000 for operating a virtual and mixed-reality enhanced exercise machine, according to one aspect. According to the aspect, a user may wear 2001 a torso harness such as a belt 420 or vest 1820 harness, while they engage in the use 2002 of an exercise machine 100. While using the exercise machine 100, the user's movements may be detected and measured 2003 through the use of a plurality of body movement sensors such as (for example, including but not limited to) strain sensors 1911, tethers 410*a*-*c*, 1912, pistons 1811, or optical sensors 1201*a*-*n*. These measured user movements may then be mapped by a composition server 801 to correspond to a plurality of movement inputs of a virtual joystick device 2004. These virtual joystick inputs may then be transmitted 2005 to a software application, for example a virtual reality or mixed reality application operating on a user device such as (for example, including but not limited to) a smartphone 930, personal computing device, or headset 302. Composition server 801 may then receive feedback from the software application 2006 and may direct the operation of a plurality of feedback devices such as tethers 410a-c, 1912 or pistons 1811 to resist or direct the user's movement 2007 to provide physical feedback to the user based on the received software feedback.

Figure 21:
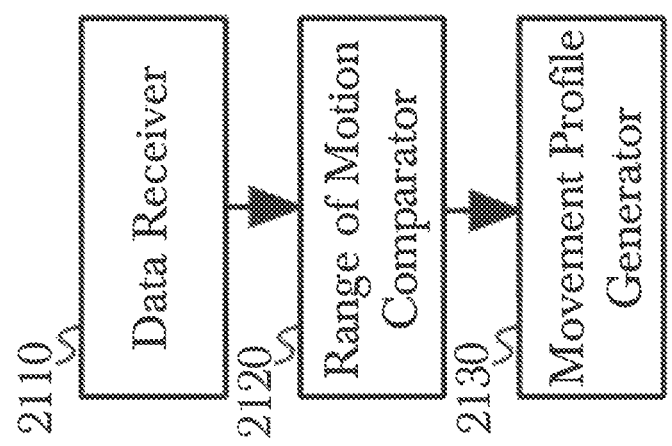
FIG. 21 is a system diagram of a key components in the analysis of a user's range of motion and balance training.

FIG. 21 is a system diagram of a key components in the analysis of a user's range of motion and balance training. A datastore containing statistical data 2110 on a user's age category, gender, and other demographic data, as well as a datastore containing balancing algorithms 2120, are connected to a collection of components integrated into an exercise system 2130, including a plurality of sensors 2131, a movement profile analyzer 2132, a balance trainer 2133, and a tuner 2134. A plurality of sensors 2131 may be connected to varying parts of an exercise system, tethered to a user, or otherwise connected to or able to sense a user during exercise, and may inform a movement profile analyzer 2132 of the performance of a user's exercise during such exercise. A movement profile analyzer 2132 may use data from a datastore containing statistical data on a user 2110 to generate movement profile of how a user performs and moves during exercise, in comparison with how they may be expected to move, and pass this data on to a balance trainer 2133 which is further connected to a datastore containing balance algorithms 2120. A balance trainer 2133 accesses and utilizes balance algorithms 2120 in conjunction with assembled movement profile data 2132 and determines if a user is in need of correcting their form or balance during exercise. A tuner 2134 is connected to a datastore containing user profile data 2150 and also connected to a balance tuner 2133, enabling a user's individual preferences or specifications, or exercise needs, to inform adjustments for a balance trainer 2133, for example if a user would initially be detected as stumbling by a balance trainer 2133 but the user were to specify that they are not falling, and continue to exercise in this fashion for whatever reason (such as physical limitations), a tuner 2134 may adjust the balance trainer 2133 in this instance. Such information is stored in a user's profile data 2150. A display 2140 is connected to core components 2130 and may display the warnings generated by a balance trainer 2133 or offer a user the opportunity to offer adjustments or physical information to a tuner 2134 for adjusting a balance trainer 2133.

Figure 22:
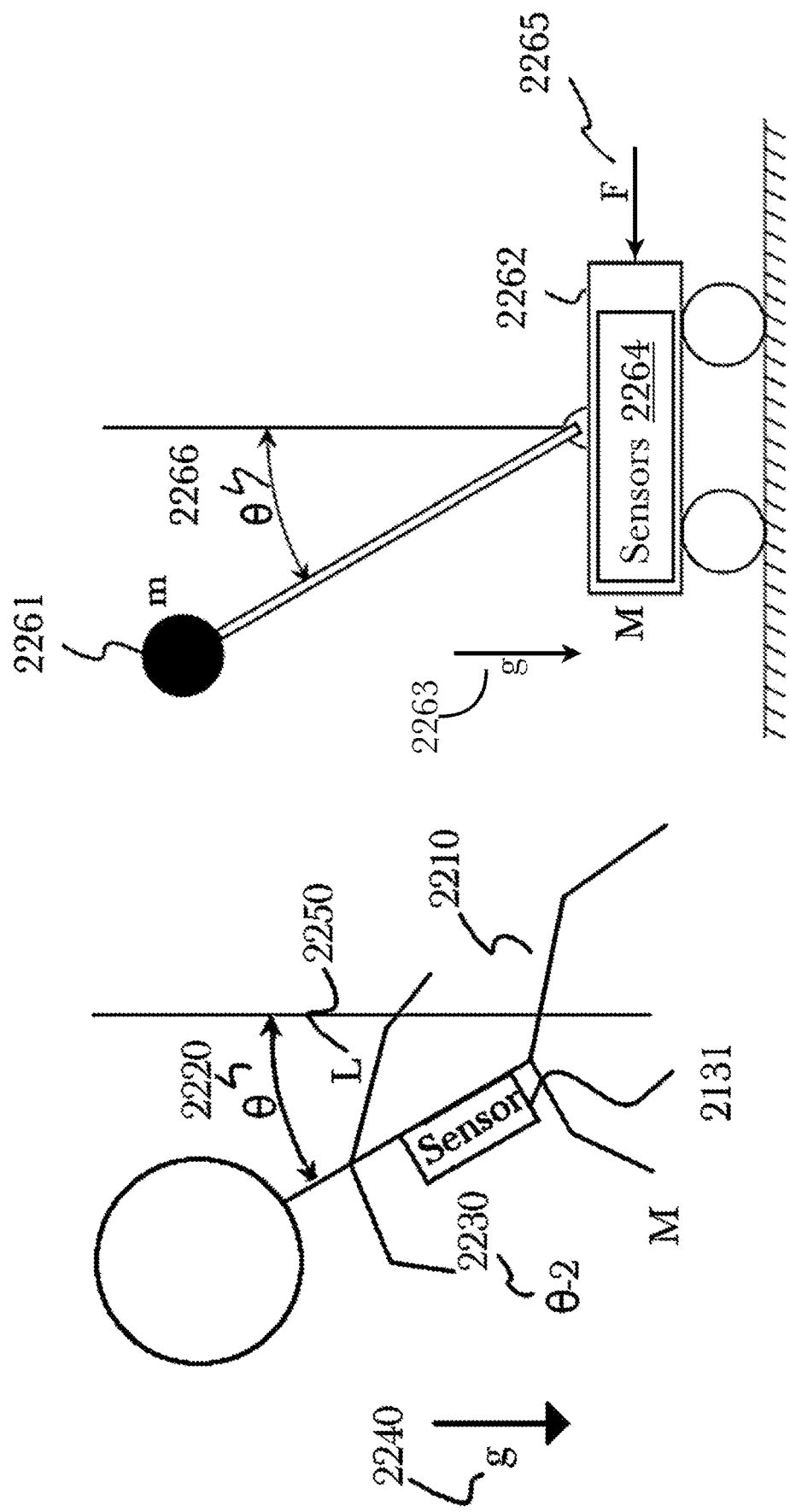
FIG. 22 is a diagram showing a system for balance measurement and fall detection.

FIG. 22 is a diagram showing a system for balance measurement and fall detection. A classic problem in control system theory is controlling an inverted pendulum such that it balances vertically without falling down. On the right side of the diagram is a drawing of the inverted pendulum problem in which a pendulum (a rod having some length, l, and some mass, m) 2261 is attached to a movable platform 2262. Sensors 2264 on the platform 2262 detect at least the angle, $\theta$, 2266 of the pendulum 2261 from vertical, and may also be configured to detect or calculate the rate of change of the angle 2266, the acceleration of the platform 2262, and other variables. As the pendulum 2261 falls away from vertical due to the force of gravity, g, 2263, a control mechanism such as a proportional, integral, differential (PID) controller may calculate and apply a force F 2265 to the platform 2262 sufficient to swing the pendulum 2261 back to vertical against the force of gravity 2262.

A similar system may be used to measure balance and detect and predict falls by a person with impaired balance abilities. A user 2210 may wear a sensor and electronics package 2131, on the torso. The sensor and electronics package 2131 may be simply a collection of sensors (e.g., accelerometers, gyroscopes, etc.) configured to transmit data to an external computing device, or the sensor and electronics package 2131 may itself have a computing device. The user's body mass, m, can be entered manually or obtained from a wireless scale capable of communicating wirelessly with the sensor and electronics package 2131. As the user's torso moves from the vertical position 2220, the angle from vertical and rate of change of the angle, $\theta''$, 2230 from vertical can be measured, tracked, and used to make predictions about the likelihood of a fall. Angular momentum 2230 may be represented by $\theta''$ 2230, a user's angle deviation from vertical being represented by $\theta$ 2220, the force of gravity being represented by g 2240, and the approximate height of a user's body-part acting similar to the bar of an inverted pendulum being represented by L 2250. The data obtained from the sensors and electronics package 2131 may be used in conjunction with various algorithms (e.g., a PID controller) and the user's historical or manually-entered movement ability to determine when the rate of fall is likely to exceed the user's ability to accelerate toward the direction of fall fast enough to right the torso. It is therefore possible to analyze and characterize a user's motions that may lead to a stumble or fall.

Figure 23:
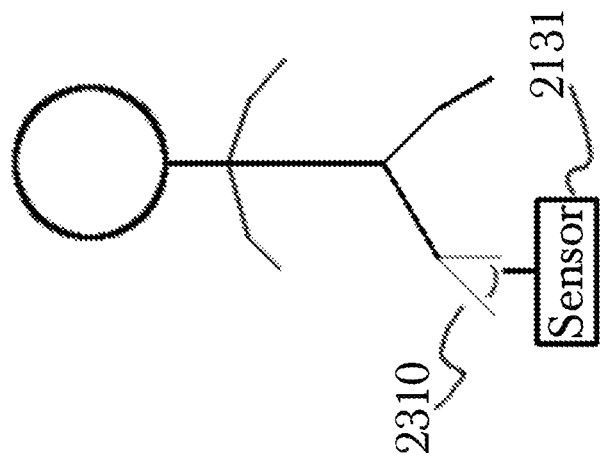
FIG. 23 is a system diagram of a sensor measuring the range of motion of a user during a specific exercise.

FIG. 23 is a system diagram of a sensor measuring the range of motion of a user during a specific exercise. A user performing an exercise with their leg is shown, with a sensor 2131 and angular movement 2310. A sensor 2131 may be used to characterize the angle of the user's motion, or be attached as an ankle weight for a more specific implementation (but by no means the only implementation of this process of using a sensor to measure an individual user's body parts during exercise), to achieve more information about user form in addition to or instead of using an inverted pendulum 2220 with a sensor 2131 inside.

Figure 24:
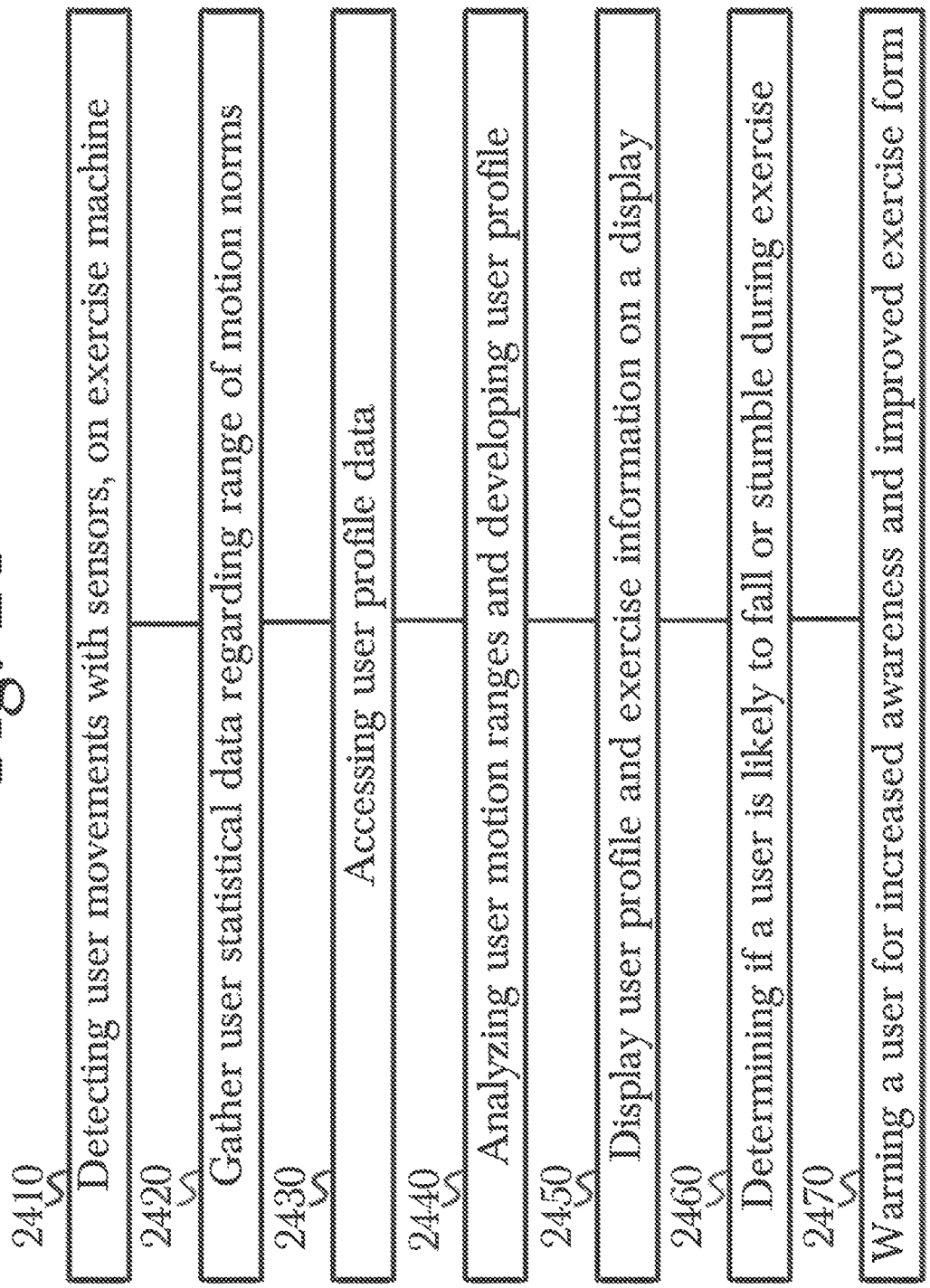
FIG. 24 is a method diagram illustrating behavior and performance of key components for range of motion analysis and balance training.

FIG. 24 is a method diagram illustrating behavior and performance of key components for range of motion analysis and balance training. A user's movements may first be detected on or with an exercise machine, using a plurality of sensors 2131, 2410. Given a user's movements 2410, statistical data on a user's demographics may be gathered 2420 using a datastore containing such information 2110, to compare a user's movements with expected or anticipated norms based on acquired or default statistical data. A user's profile data 2150 may then be accessed 2430 and using a user's profile data 2150 which may contain individual preferences or information beyond statistical norms 2110 or sensor-acquired exercise data 2131, analyses of a user's range of motion may occur 2440. Such analyses may include examining differences between a user's expected motion during an exercise, with their actual motion, measuring individual, anomalous movements during a user's exercise (such as a single motion that does not match with the rest of the user's movements), and other techniques to analyze anomalies in a user's displayed exercise ability. A user's profile is also generated from these analyses 2440, allowing a history of a user's exercise performance to be recorded for future analysis and for comparison with future observed exercise patterns and performance. A user's profile and exercise performance, along with any other notes, may be displayed 2450 with a graphical or textual display 2140, allowing a user to see for themselves their performance and deficiencies as determined by the system. A further step may be to detect if a user is detect to be likely to fall or stumble 2460, such as if a leg movement is not proper for a running motion on a treadmill, and display or sound a warning to a user 2470 using a display 2140 or any other method that may be available to the physical activity data capture device for warning a user of possible injury or failure. These warnings may further be recorded in a user profile 2150 for access by a tuner 2134 and balance trainer 2133 to help the user be aware of patterns of exercise performance that may lead to similar incidents in the future, before they happen, thereby helping to ensure safety of physically at-risk exercise machine users.

Figure 31:
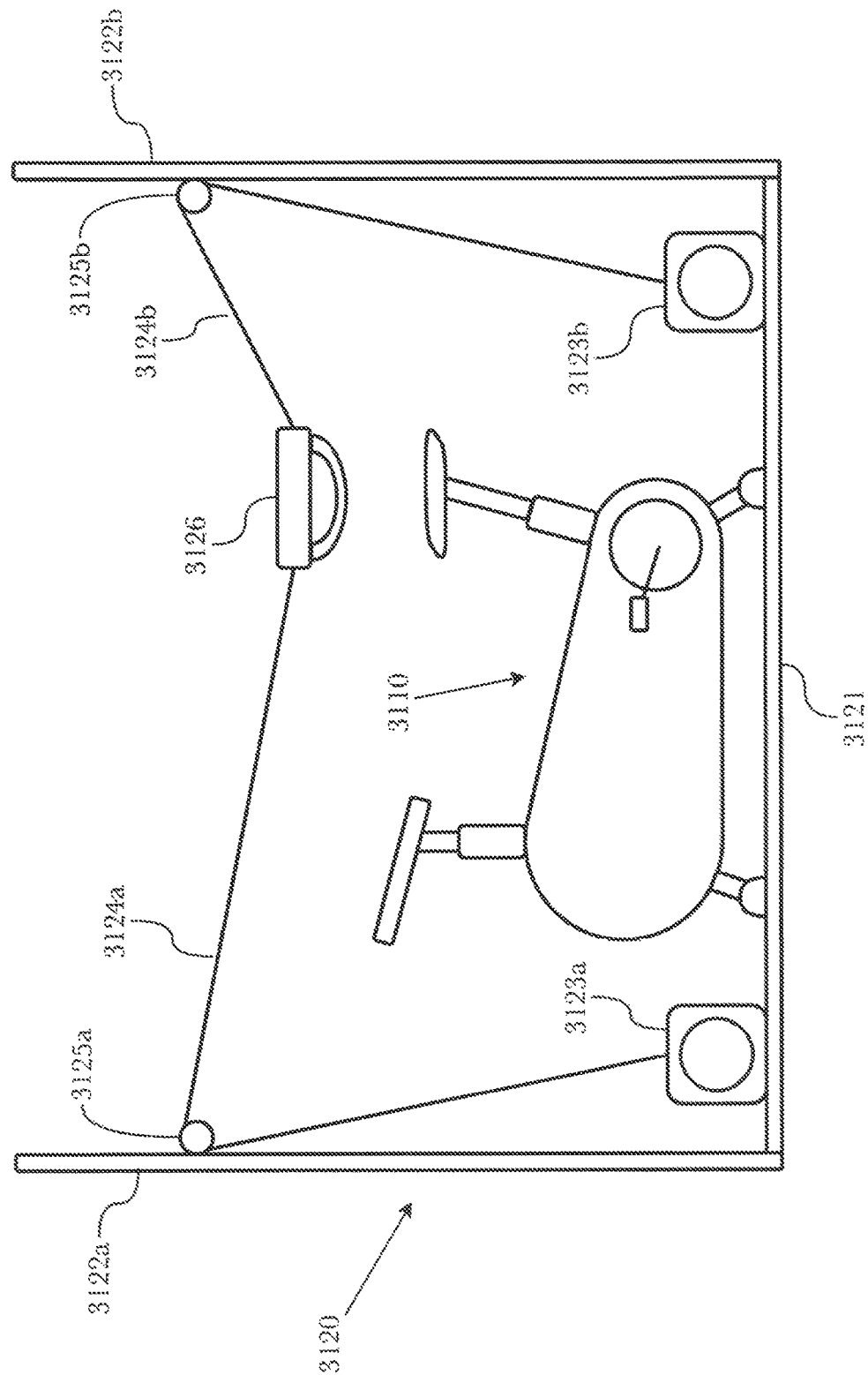
FIG. 31 is an exemplary human/machine interface and support system for using body movements to interface with computers while engaging in exercise.

FIG. 31 is an exemplary human/machine interface and support system for using body movements to interface with embedded or external computers while engaging in exercise. In this embodiment, an exercise machine 3110 is placed inside a frame 3120 which contains components for sensing the movement of an individual, providing haptic feedback, and providing support in case of a fall. In this embodiment, the exercise machine 3110 is depicted as a stationary bicycle, although any type of exercise machine 3110 (e.g., treadmill, stair-stepper, rowing machine, weight-lifting machines, etc.) may be used. The exercise machine 3110 may contain or be in communication with an embedded or external computer that communicates with other components of the system, although in some embodiments, the exercise machine 3110 is not communicatively coupled with other components. In some embodiments, no exercise machine 3110 at all is used, and the individual may freely engage in exercise or other physical movement such as running in place, jumping, dancing, lifting barbells or free weights, etc. The frame 3120 comprises a base 3121 and one or more vertical supports 3122$a,b$. Mounted to a point on the vertical supports are one or more pulleys or routing devices 3125$a,b$, which guide one or more tethers 3124$a,b$ at a height above the waist level of the individual during exercise. The tethers 3124$a,b$ are attached at one end to a belt, harness, vest, or other device 3126 attachable to the body of the individual, and at the other end to sensors/actuators 3123$a,b$. In this embodiment, the sensors/actuators 3126$a,b$ are electric motors fitted with rotary encoders and the tethers 3124$a,b$ are wound around a drum on the shaft of the motors. In this way, body movements of the individual may be sensed and recorded as rotational movements of the drum, and rotational movement data may be sent to a computing device which can perform calculations to determine position, distance of movement, speed of movement, acceleration, and other such calculations. For example, the linear distance of movement may be calculated from the number of rotations and the circumference of the drum. Linear speed may be calculated as the linear distance over time. The position of the individual may be calculated from speed and distance. The rotational movement, linear distance, linear speed, or other calculations may be used to control the computing device or the output from a computing device such as a game, virtual reality environment, etc. Further, the motors of the sensors/actuators 3123$a,b$ may also act as actuators, and varying voltages and currents may be applied to the motors to provide haptic feedback to the individual, such as resistance to movement, jerking, or vibration. This haptic feedback may be provided in response to interactions with the computer, such as to indicate game events, interactions with the virtual reality environment, etc. In one aspect, the belt 3126, tethers 3124$a,b$, and sensors/actuators 3123$a,b$, may be used to support the individual in case of a slip or fall. Such support may be provided passively (e.g., a fixed resistance provided by the motors), actively (e.g., by sensing an acceleration and applying a resistance to the tethers), or by mechanical means (e.g., seatbelt-type mechanical locking mechanism that locks the tether upon a sudden pull). Other embodiments may use additional vertical supports 3122$a,b$, tethers, 3124$a,b$, and sensors/actuators 3123$a,b$. For example, some embodiments may have vertical supports 3122$a,b$ and associated equipment at the front and back, and at the left and right sides of the individual. Many other configurations are possible.

Figure 32:
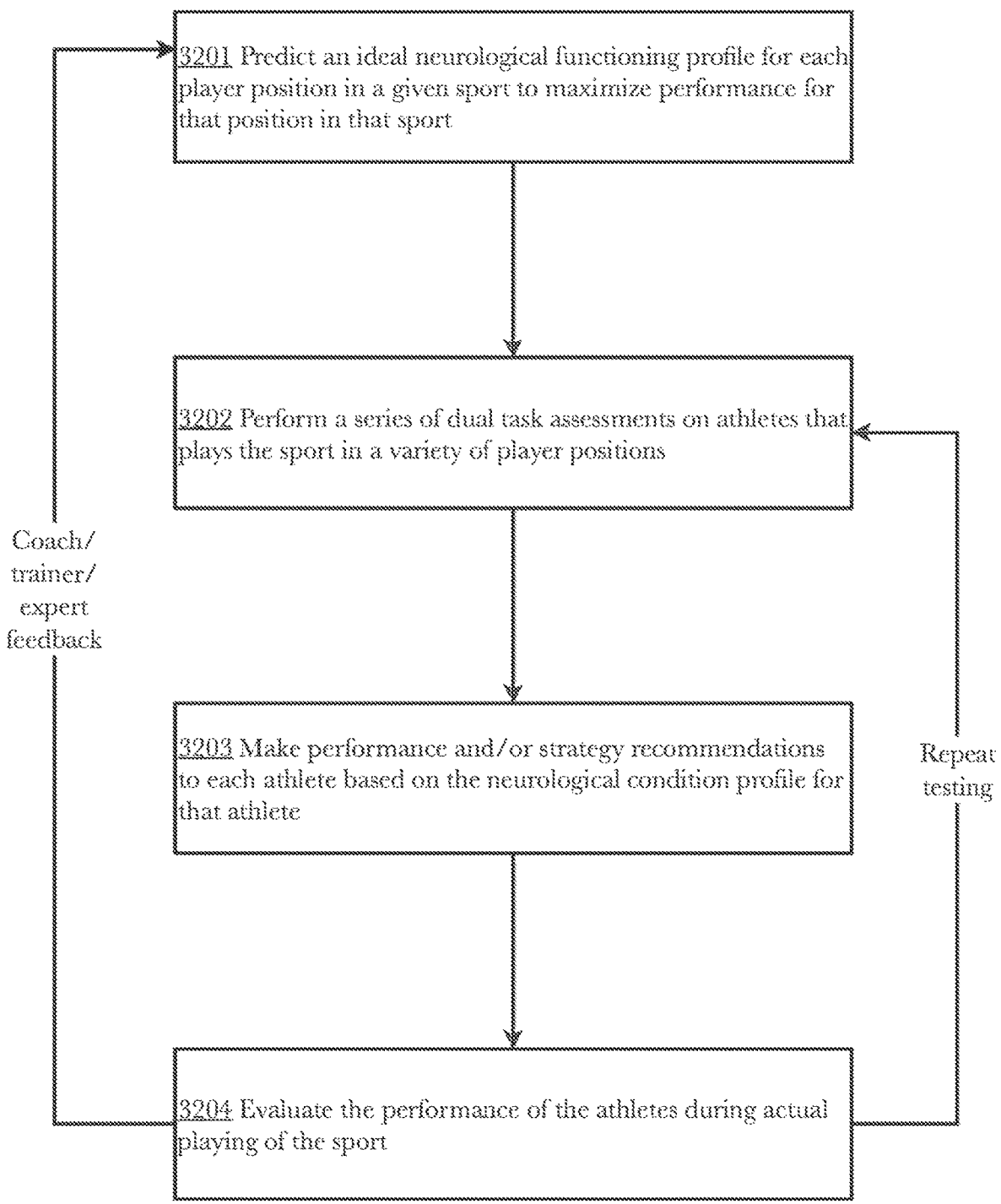
FIG. 32 is an exemplary method for application of the system to improve the performance of a sports team.

FIG. 32 is an exemplary method for application of the system to improve the performance of a sports team. In a first step, an ideal neurological functioning profile for each player position in a given sport is predicted by experts in the sport (e.g., coaches, trainers, athletes, sports bettors, etc.) for maximization of performance for that position in that sport 3201. Then, dual task assessments are performed for athletes from a variety of positions that play the sport 3202. Based on the neurological condition profile generated by the testing, performance and/or play strategy recommendations are made for performance improvements for that player for that position 3203. Performance of the athletes during actual play is evaluated by the experts in the sport 3204. The evaluation feedback from the experts is provided back to step 3201, and athletes are retested at step 3202. All of these steps may be performed repeatedly to continuously refine input and recommendations. In some embodiments, dual task assessments at step 3202 may be specifically selected to condition or train the aspects of neurological functioning determined to be ideal at step 3201 (i.e., step 3202$a$ can be both a conditioning/training step and an evaluation step).

Figure 37:
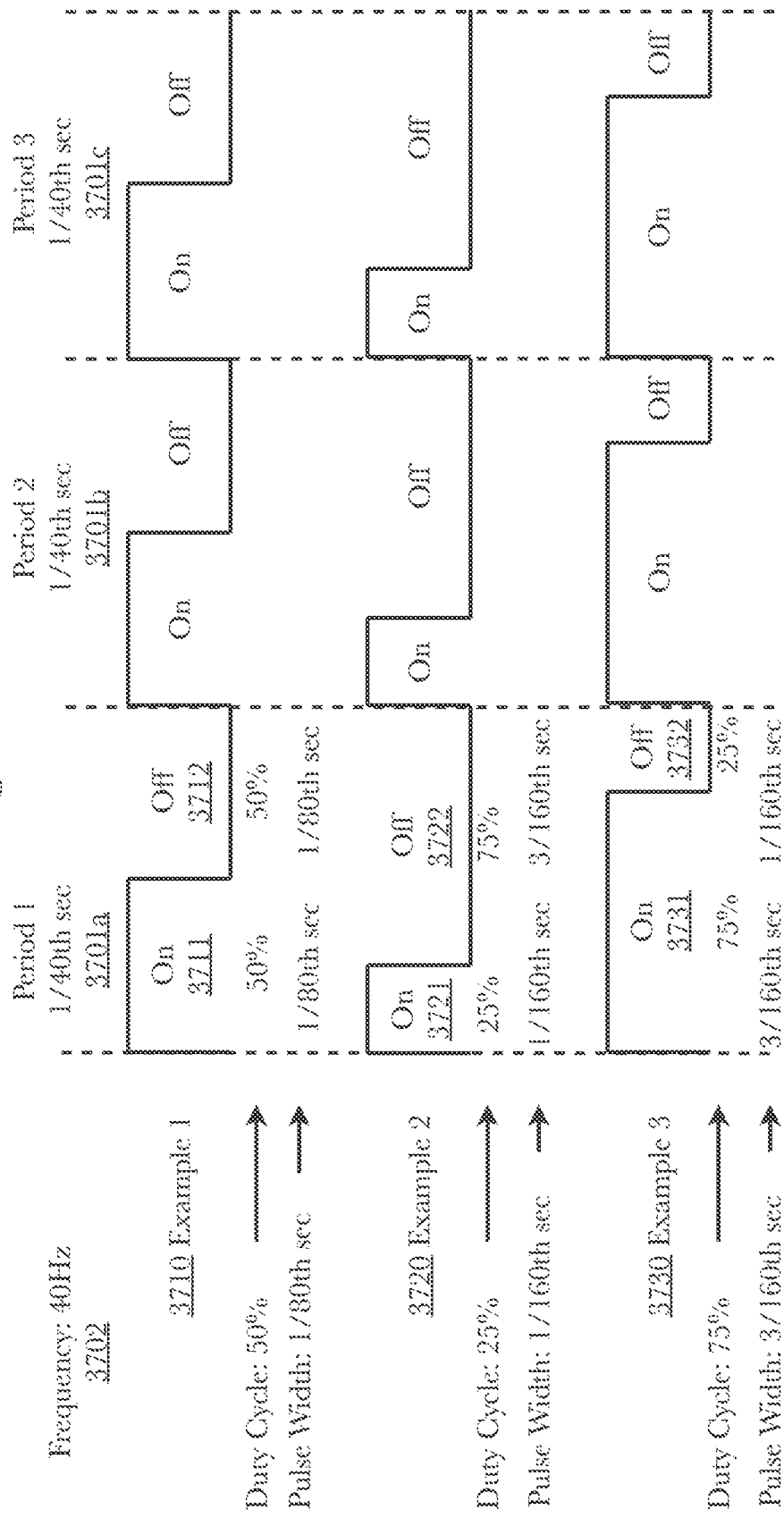
FIG. 37 is a diagram showing explaining the use of duty cycles and pulse width modulations in applying brainwave entrainment.

FIG. 37 is a diagram showing the use of duty cycles and pulse width modulations in applying brainwave entrainment. Here, three examples 3710, 3720, and 3730 of duty cycles/pulse width modulation are shown. The frequency of stimulation 3702 in all three examples is 40 Hz (40 cycles per second), and the wave form of each example is a rectangular wave (i.e., instantaneous or near-instantaneous changes between on and off states). Three periods 3701$a$-$c$ of the stimulation at the 40 Hz frequency 3702 are shown, each period corresponding to one full on/off cycle lasting $\frac{1}{40}^{th}$ of one second. In Example 1 3710, a duty cycle of 50% is shown in which the stimulation is in an on state 3711 for 50% of the period and in an off state 3712 for 50% of the period. For a 40 Hz frequency as shown here, this corresponds to a pulse width of $\frac{1}{80}^{th}$ of a second, wherein the stimulation is in an on state 3711 for $\frac{1}{80}^{th}$ of a second and in an off state 3712 for $\frac{1}{80}^{th}$ of a second. In Example 2 3720, a duty cycle of 25% is shown in which the stimulation is in an on state 3721 for 25% of the period and in an off state 3722 for 75% of the period. For a 40 Hz frequency as shown here, this corresponds to a pulse width of $\frac{1}{160}^{th}$ of a second, wherein the stimulation is in an on state 3721 for $\frac{1}{160}^{th}$ of a second and in an off state 3722 for $\frac{3}{160}^{th}$ of a second. In Example 3 3730, a duty cycle of 75% is shown in which the stimulation is in an on state 3731 for 75% of the period and in an off state 3732 for 25% of the period. For a 40 Hz frequency as shown here, this corresponds to a pulse width of $\frac{3}{160}^{th}$ of a second, wherein the stimulation is in an on state 3731 for $\frac{3}{160}^{th}$ of a second and in an off state 3732 for $\frac{1}{160}^{th}$ of a second.

Figure 38:
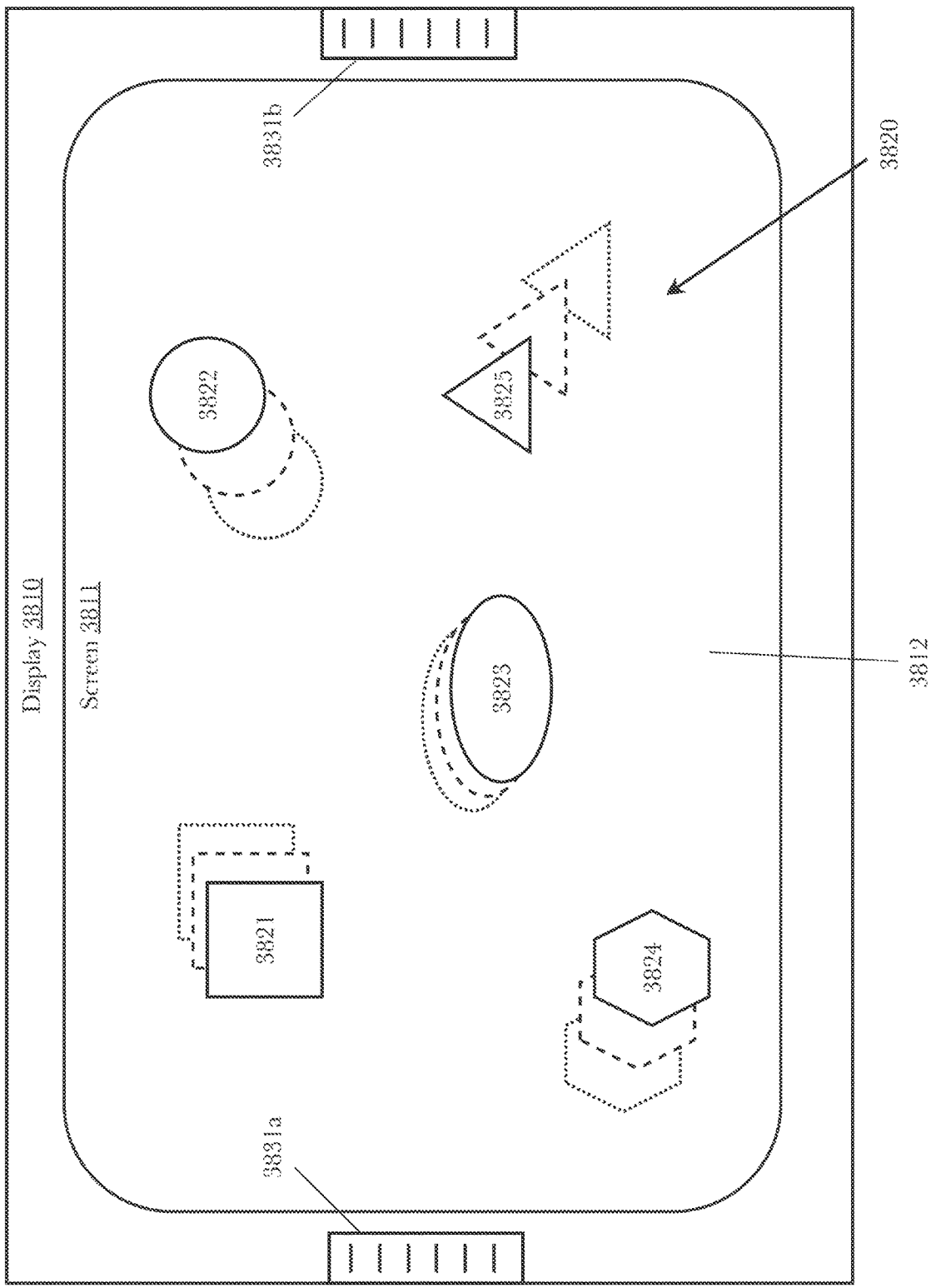
FIG. 38 is a diagram showing an embodiment in which on-screen elements of a display are used to apply brainwave entrainment.

FIG. 38 is a diagram showing an embodiment in which on-screen elements of a display are used to apply brainwave entrainment. In this example, brainwave entrainment is implemented using a display 3810, such as a television computer monitor, or tablet-based device, comprising a screen 3811 and in some configurations, built in speakers 3831a,b. In this embodiment, the screen is used to provide visual brainwave entrainment, either by flashing the background of the screen 3812 or one or more on-screen elements 3820. This embodiment enables the provision of brainwave entrainment without the use of (or in addition to) external devices such as lights and speakers. In this example, five on-screen elements are shown 3821-3825, each comprising a different shape and each moving independently on the screen 3811 as indicated by the dashed and dotted "movement shadows" associated with each on-screen element. The on-screen elements 3821-3825 are generic shapes in this diagram, but may represent any type of on-screen element whether static or movable, permanent or transient. Depending on the configuration, the on-screen element may be any shape or color displayable on a screen, such as game elements, puzzle elements, background elements, regular or irregular portions of the screen. Many possible applications of this embodiment are possible. The built-in speakers, if any, may be used to provide auditory brainwave entrainment in addition to the visual on-screen brainwave entrainment.

For example, when paired with a camera and eye-tracking software, the on-screen elements might represent an eye muscle strengthening exercise combined with brainwave entrainment, wherein the user is asked to find a target on-screen element with a particular shape and follow the shape with his or her eyes. At the same time the target element may flash a particular color at a selected brainwave entrainment frequency, with the color changing as the user's eyes either follow the target on-screen element or stray from it. The target on-screen element may, for example, be a pleasant light-blue color while the user's eyes are following it, and change to a bright red to re-attract the user if the user's eyes start following a different on-screen element.

In another use case, the on-screen elements 3820 may represent a puzzle or game, and the brainwave entrainment may be provided by simply flashing the screen background 3812 at a selected brainwave entrainment frequency.

While not shown here, this example may be extended to virtual reality applications, wherein brainwave entrainment is provided by flashing in-game elements within the virtual reality environment.

Figure 43A:
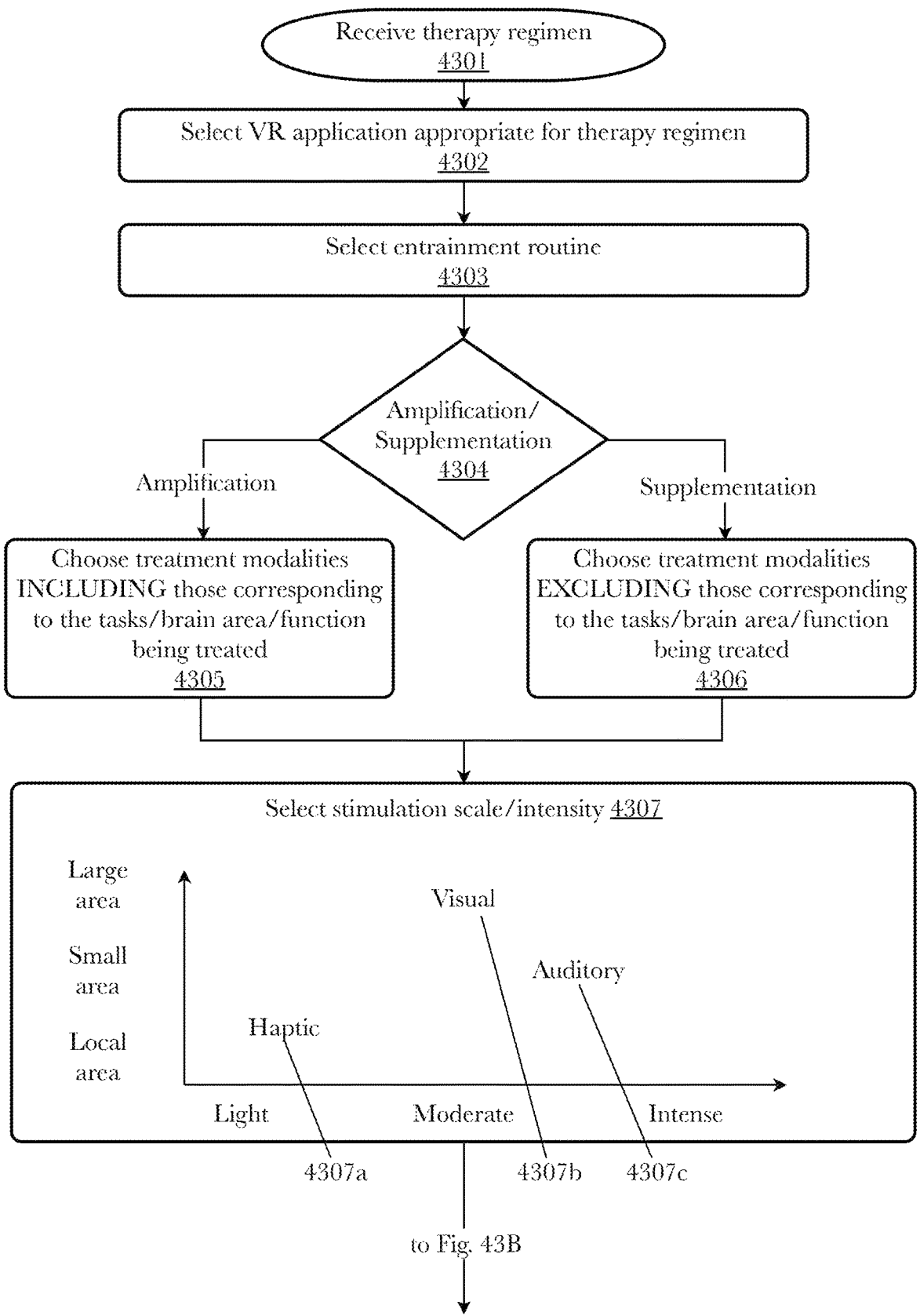
FIGS. 43A & 43B are a flow diagrams showing an algorithm for selection of modalities and routines for brainwave entrainment and application of brainwave entrainment using a virtual environment using eye tracking and biometric feedback to select virtual objects and entrainment routines.
Figure 43B:
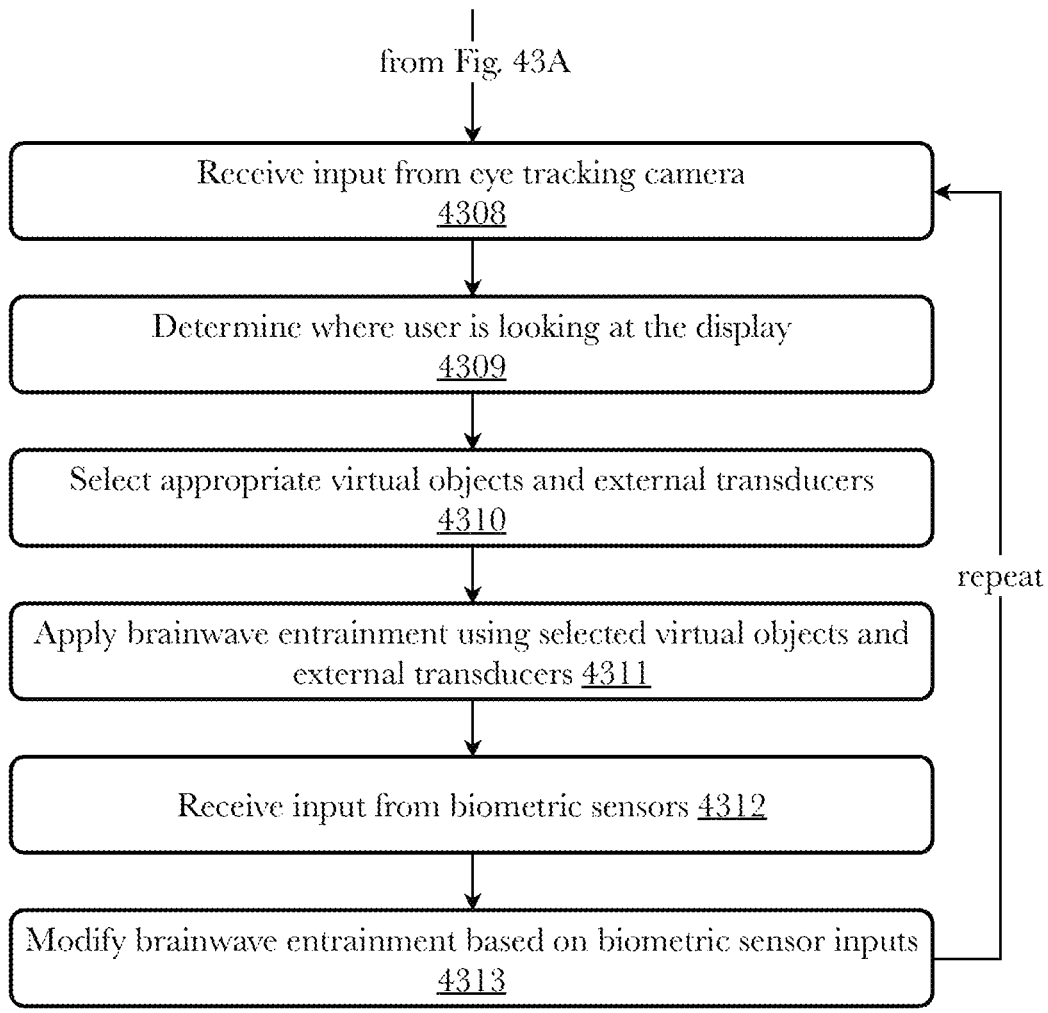

FIGS. 43A & 43B are a flow diagram showing an algorithm for selection of modalities and routines for brainwave entrainment and application of brainwave entrainment using a virtual environment using eye tracking and biometric feedback to select virtual objects and entrainment routines. As a first step, a therapy regimen is received 4301 The therapy regimen may be received from any source providing instructions for brainwave entrainment, such as a database, an administrator (e.g., a physician, therapist, masseuse, or other service provider) for application to a user (who may be a patient, client, etc., of the administrator), or from the user himself or herself. An example therapy regimen would be a regimen for brainwave entrainment that emphasizes alpha wave stimulation to induce relaxation in an overstimulated user.

A suitable VR application or other gamification application is then chosen 4302, which ideally should be consistent in content with the nature of the therapy regimen chosen. For example, if the therapy regimen is a regimen for brainwave entrainment that emphasizes alpha wave stimulation to induce relaxation in an overstimulated user, a VR application might be chosen that involves causal cycling along a forest path. If a more stimulating therapy regimen is chosen, for example something involving intense concentration and gamma wave therapy, a first-person shooter might be chosen.

Based on the therapy regimen and VR application chosen, an entrainment routine is selected 503. For example, if the therapy regimen specifies that the overall brainwave entrainment goal is relaxation, the entrainment routine selected 4303 may use alpha wave entrainment as the primary entrainment therapy, and may choose to apply alpha wave entrainment to a background virtual object (e.g., the sky or trees in the background of the casual cycling along the forest path), as flashing of background objects will be less intrusive (and possibly more relaxing) to the user than flashing of objects to which the user's attention is directed (e.g., the path or direction of the virtual bicycle). Selection of the entrainment routine 4303 may further involve selecting amplification or supplementation 4304 as appropriate for the circumstances, choosing appropriate treatment modalities (e.g., light therapy, sound therapy, vibrational therapy, electrical therapy, or combinations of such modalities) either for amplification 4305 (treatments including those corresponding to the tasks, activities, or neurological function) or for supplementation 4306 (treatments including those corresponding to the tasks, activities, or neurological function), and selecting a stimulation scale and intensity 4307 for each modality appropriate for the treatment goals. In this example, three modalities are shown with different scales and intensities, localized haptic stimulation at a light intensity 4307a, large area visual stimulation at a moderate intensity 4307b, and small area auditory stimulation at a moderately intense intensity 4307c. Brainwave entrainment is then applied using the chosen regimen, providing targeted treatment of particular areas of the brain and/or particular neurological functions via stimulation of those areas or functions using dual task stimulation.

At this point, a camera may be used to track the user's eye movements 4308 to determine where the user is looking on the screen at a given moment 4309. Based on the above inputs, appropriate virtual objects are chosen to apply brainwave entrainment by modifying virtual objects on the screen 4310, which modification may take any number of forms (e.g., objects may be flashed at specific frequencies, the color of objects may be changed at specific frequencies, the size of objects may be changed at specific frequencies, objects may be rotated at specific frequencies, etc.). Any change to a virtual object that is perceptible to a user and can be applied at a repeating frequency (i.e., oscillating frequency) may be used to apply brainwave entrainment. Brainwave entrainment is applied using the virtual objects, optionally supplemented with entrainment from external transducers 4311.

Input from biometric feedback (e.g., the user's heart rate) is received 4312 and evaluated to determine whether the selected entrainment routine is having the desired effect (e.g., a lowering heart rate may be used to infer relaxation), and to change the entrainment routine, accordingly 4313. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation. The process of tracking the user's attention and applying appropriate modifications to brainwave entrainment is repeated from step 4308 until the therapy session ends.

Figure 44:
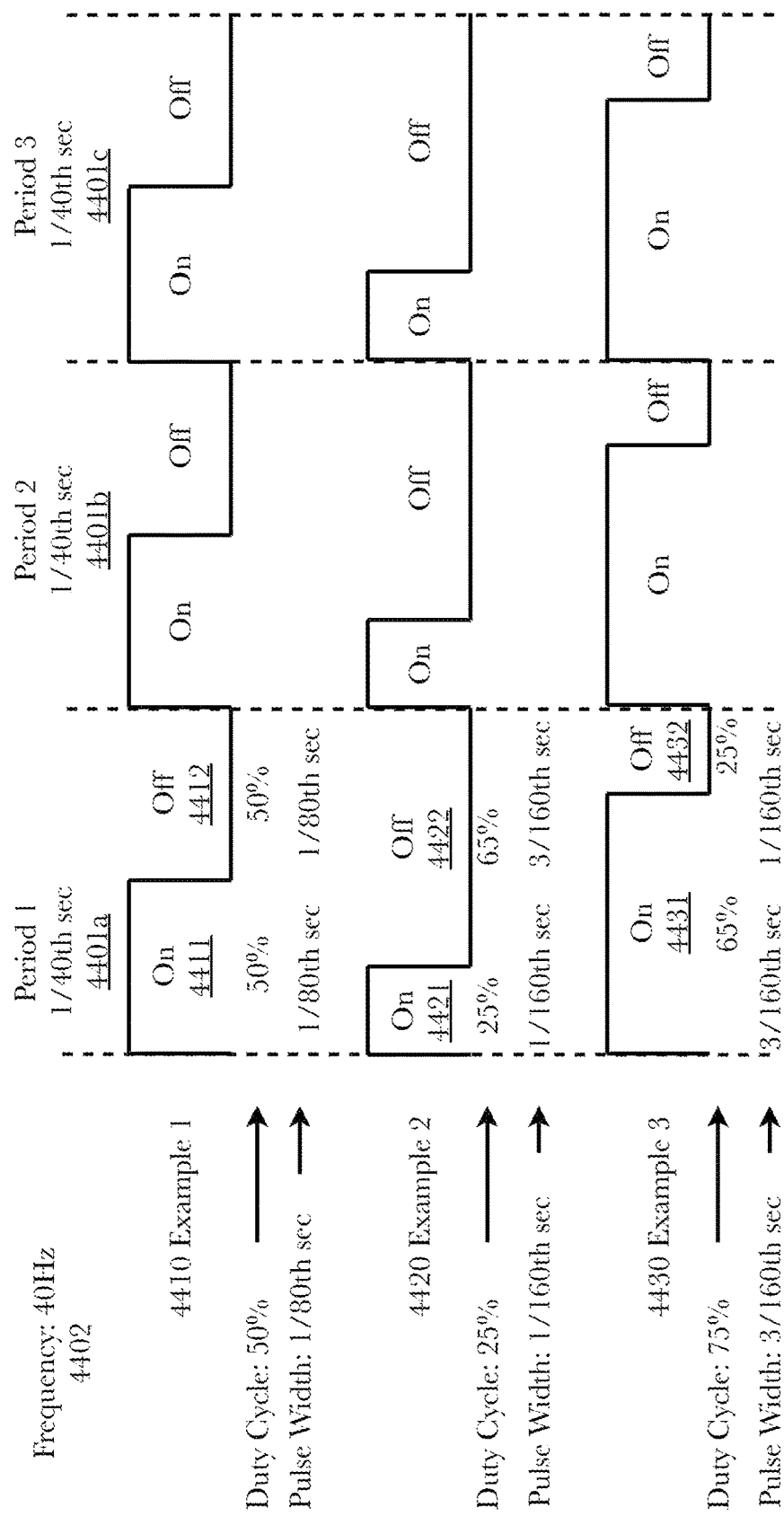
FIG. 44 is a diagram explaining the use of duty cycles and pulse width modulations in applying brainwave entrainment.

FIG. 44 is a diagram showing explaining the use of duty cycles and pulse width modulations in applying brainwave entrainment. Here, three examples 4410, 4420, and 4430 of duty cycles/pulse width modulation are shown. The frequency of stimulation 4402 in all three examples is 40 Hz (40 cycles per second), and the wave form of each example is a rectangular wave (i.e., instantaneous or near-instantaneous changes between on and off states). Three periods 4401*a-c* of the stimulation at the 40 Hz frequency 4402 are shown, each period corresponding to one full on/off cycle lasting $1/40^{th}$ of one second. In Example 1 4410, a duty cycle of 50% is shown in which the stimulation is in an on state 4411 for 50% of the period and in an off state 4412 for 50% of the period. For a 40 Hz frequency as shown here, this corresponds to a pulse width of $1/80^{th}$ of a second, wherein the stimulation is in an on state 4411 for $1/80^{th}$ of a second and in an off state 4412 for $1/80^{th}$ of a second. In Example 2 4420, a duty cycle of 25% is shown in which the stimulation is in an on state 4421 for 25% of the period and in an off state 4422 for 75% of the period. For a 40 Hz frequency as shown here, this corresponds to a pulse width of $1/160^{th}$ of a second, wherein the stimulation is in an on state 4421 for $1/160^{th}$ of a second and in an off state 4422 for $3/160^{th}$ of a second. In Example 3 4430, a duty cycle of 75% is shown in which the stimulation is in an on state 4431 for 75% of the period and in an off state 4432 for 25% of the period. For a 40 Hz frequency as shown here, this corresponds to a pulse width of $3/160^{th}$ of a second, wherein the stimulation is in an on state 4431 for $3/160^{th}$ of a second and in an off state 4432 for $1/160^{th}$ of a second.

FIGS. 45-47 (PRIOR ART) explain the application of eye tracking technology as a means of determining where a user is looking. In one form of eye tracking technology, an infrared emitter 4520 emits an infrared light 4521, which is reflected off the user's eye 4501 and cornea, and is received 4531 at an infrared-sensitive camera 4530. The image of the of the user's eye appears to the camera substantially as shown in FIG. 47, wherein the sclera (the white part of the eye) 4701, the iris (the colored part of the eye) 4702, and the pupil (the opening in the eye) 4703 are visible. The center of the eye 4710 is tracked, as shown by a first set of crosshairs 4711, in relation to a reflection from the cornea (the outer surface of the eye) 4720, as shown by a second set of crosshairs 4721. The distance and direction of the difference between the center of the eye and the corneal reflection can be used to calculate the eye's position. Combined with a known distance to and size of a display, 4540, the location at which the user is looking 4502 can be determined. FIG. 46 shows the same application of eye tracking technology, but inside a VR headset 4640. In FIG. 46, an infrared emitter 4620 emits an infrared light 4621, which is reflected off the user's eye 4601 and cornea, and is received 4632 at an infrared-sensitive camera 4630. The distance and direction of the difference between the center of the eye and the corneal reflection can be used to calculate the eye's position. Combined with a known distance to and size of a display, 4641, the location at which the user is looking 4602 can be determined.

FIG. 48 is a diagram showing an embodiment in which on-screen virtual objects on a display are used to apply brainwave entrainment. In this example, brainwave entrainment is implemented using a display 4810, such as a television computer monitor, or tablet-based device, comprising a screen 4811 and in some configurations, built in speakers 4831*a,b*. In this embodiment, the screen 4811 is used to provide visual brainwave entrainment, either by flashing the background of the screen 4811 or one or more on-screen virtual objects 4820. This embodiment enables the provision of brainwave entrainment without the use of (or in addition to) external devices such as lights and speakers. In this example, five on-screen virtual objects 4820 are shown 4821-4825, each comprising a different shape and each moving independently on the screen 4811 as indicated by the dashed and dotted "movement shadows" associated with each on-screen virtual objects 4820. The on-screen virtual objects 4820 are generic shapes in this diagram, but may represent any type of on-screen element whether static or movable, permanent or transient. Depending on the configuration, the on-screen element may be any shape or color displayable on a screen, such as game elements, puzzle elements, background elements, regular or irregular portions of the screen. Many possible applications of this embodiment are possible. The built-in speakers, if any, may be used to provide auditory brainwave entrainment in addition to the visual on-screen brainwave entrainment.

For example, when paired with a camera and eye-tracking software, the on-screen virtual objects 4820 might represent an eye muscle strengthening exercise combined with brainwave entrainment, wherein the user is asked to find a target on-screen virtual object with a particular shape and follow the shape with his or her eyes. At the same time the target virtual object may flash a particular color at a selected brainwave entrainment frequency, with the color changing as the user's eyes either follow the target on-screen virtual object or stray from it. The target on-screen virtual object may, for example, be a pleasant light-blue color while the user's eyes are following it, and change to a bright red to re-attract the user if the user's eyes start following a different on-screen element.

In this embodiment, a clip-on eye-tracking unit 4840 may be attached to the display 4810 using plastic (or other material) clips 4844. The clip-on eye-tracking unit 4840 comprises a housing 4841, an infrared emitter 4842 which emits an infrared light that is reflected off the user's eye and cornea, and is received at an infrared-sensitive camera 4843, and clips 4844 which may be used to attach the clip-on eye-tracking unit 4840 to a display 4810. The center of the eye is tracked in relation to a reflection from the cornea (the outer surface of the eye). The distance and direction of the difference between the center of the eye and the corneal reflection can be used to calculate the eye's position. Combined with a known distance to and size of the display 4810 the location at which the user is looking can be determined.

In another use case, the on-screen virtual objects 4820 may represent a puzzle or game, and the brainwave entrainment may be provided by simply flashing the screen background 4812 at a selected brainwave entrainment frequency.

This example may be extended to virtual reality applications, wherein brainwave entrainment is provided by flashing in-game elements within the virtual reality environment.

FIG. 49 is a diagram showing an exemplary virtual reality environment in which virtual objects may be used as visual stimulation transducers. The virtual reality environment show in this diagram depicts a quiet scene from a first person perspective, and would be suitable for brainwave entrainment related to theta or alpha wave entrainment (for example, to facilitate relaxation, creativity, exploration, and contemplation). The environment comprises a room with a floor 4910, a ceiling 4912, and three visible walls 4911*a-c*. In the ceiling are four recessed lights 4913. On the left wall 4911*a* is a flat-screen television 4923 showing an outdoor scene 4924 involving mountains, trees, and lightning. On the right wall 4911*c* is a door 4914. On the back wall is a window to the outside 4915 in which the sun can be seen 4930. In the corner of the room is a potted plant 4922, and next to the back wall 4911b is a table 4920 on which is standing a lamp 4921. Each and every virtual object named above can be used to provide brainwave entrainment. For example, any one or all of the virtual lighting objects, the lamp 4921, the television, 4924, the ceiling lights 4913, and the sun 4930 could be flashed or changed in intensity at the selected brainwave entrainment frequency. Even objects not associated with lighting, such as the walls 4911a-c, ceiling 4912, floor 4910, or door 4914, could be flashed or changed. If appropriate to the therapy regimen selected, exploration and curiosity could be encouraged by flashing certain objects (e.g., the television 4924, the potted plant 4922, the table 4920, the door 4914) as the user investigates or interacts with them. With some additions, a scene such as the one depicted here could be used to perform brainwave entrainment in a mystery or other storyline. Other modalities of brainwave entrainment such as sound and haptic feedback may be applied simultaneously with the visual stimulation. As more fully described above, these other modalities may be applied using either the same or different brainwave entrainment frequencies. As a non-limiting example, if a user in the virtual reality environment switches on the lamp 4921, not only might the lamp 4921 flash or change color at a brainwave entrainment frequency as a form of visual stimulation, an audible tone might be generated corresponding to the lamp flickering at the same entrainment frequency, and haptic feedback in the form of vibration of a game controller might also be applied. In some applications, for example in virtual environments comprising a darkened environment such as a room with the lights turned off, the visual stimulation may not be used, but the auditory and/or haptic stimulation modalities may continue to be applied.

FIG. 50 is a diagram showing exemplary gamification of brainwave entrainment in which in-game objects and elements are used as visual stimulation transducers in conjunction with gameplay activities. The gameplay example shown here depicts a first-person shooter (FPS) involving shooting of attacking aliens, and would be suitable for brainwave entrainment related to beta or gamma wave entrainment (for example, to facilitate concentration, planning, or problem-solving). The environment comprises a laser gun 5020 controllable by the user, a spaceship 5012, a space background 5013 comprising stars 5010, and a plurality of attacking aliens 5011. The laser gun 5020 is shown here with a laser flash 5021, the resulting laser beam 5022, and its impact 5023 on one of the attacking aliens 5011. Each and every virtual object named above can be used to provide brainwave entrainment. For example, aliens 5011 may be flashed or changed as the user's attention focuses on them. The laser flash 5021, laser beam 5022, and impact 5023 can all be used to provide bright visual stimulation at an appropriate frequency during game play. Even the background 5013 and stars 5010 could be changed in color or brightness at an appropriate frequency.

In some embodiments, virtual reality environments and games could be used to provide entrainment opposite of the common expectation. For example, in the calm room shown in FIG. 49, gamma wave brainwave entrainment associated with concentration and planning could be applied to increase the user's awareness when in calm or innocuous-looking environments. Similarly, while playing an intense FPS such as that shown in FIG. 50, theta or alpha wave entrainment could be applied to calm the user during otherwise-intense game play. In a related use case where a user is addicted to the adrenalin received from intense game play, theta or alpha brainwave entrainment could be used to reduce the player's addition to games by calming the player during intense game play, reducing the adrenalin rush from playing highly-immersive, fast-action games with intense themes.

Other modalities of brainwave entrainment such as sound and haptic feedback may be applied simultaneously with the visual stimulation. As more fully described above, these other modalities may be applied using either the same or different brainwave entrainment frequencies. As a non-limiting example, when the user in the virtual reality environment shoots the alien 5011, not only might the impact 5023 provide visual brainwave entrainment, but an audible tone might be generated corresponding to the flashing or color changing of the impact 5023 at the same entrainment frequency, and haptic feedback in the form of vibration of a game controller might also be applied. In some applications, for example in virtual environments comprising a darkened environment, the visual stimulation may not be used, but the auditory and/or haptic stimulation modalities may continue to be applied.

FIG. 54 is a flow diagram illustrating an exemplary process for generating a unified tracking model of a user, according to an aspect. According to the aspect, the process begins when extended reality therapy system 5100 receives, retrieves, or otherwise obtains a plurality of sensor data from various types of sensors 5402. Because of the large number of sensors that may be present and the fact that sensors may provide exclusive and/or duplicate data as other sensors, it is necessary for the data to be processed by data capture system 5110 before further downstream components and processes may occur. Data capture system 5110 may perform sensor fusion techniques in order to integrate the plurality of sensor data 5404. From this integrated data, tracking information is extracted at step 5406 and used to generate a real-time unified tracking model 5408 for each user of extended reality therapy system 5100. The unified tracking model may make use of 3D skeletons and 3D hand models of each of the user's hands in order to generate a user avatar that can be placed and moved within a shared virtual environment. After generation of the unified tracking model, it may be stored 5410 in a database, such as VR database 5120 for storage and retrieval as necessary. A stored tracking model of an individual may be linked to a user profile and retrieved during subsequent uses by the individual.

FIG. 55 is a flow diagram illustrating an exemplary process for generating a real-time environmental model of shared a real-world space, according to an aspect. According to the aspect, the process begins when extended reality therapy system 5100 receives, retrieves, or otherwise obtains a plurality of sensors data from various types of sensors 5502. Because of the large number of sensors that may be present and the fact that sensors may provide exclusive and/or duplicate data as other sensors, it is necessary for the data to be processed by data capture system 5110 before further downstream components and processes may occur. Data capture system 5110 may perform sensor fusion techniques in order to integrate the plurality of sensor data 5504. From this integrated data, environmental information is extracted at step 5506 and used to generate a real-time environmental model of a shared real-world space 5508. The real-time environmental model may make use of a scene object model 5240 and a VR database 5120 comprising various definitions and semantic relations, in order to generate and render a shared virtual environment that is mapped to the real-world space. After generation of the environmental model, it may be stored 5510 in a database, such as VR database 5120 for storage and retrieval as necessary. A stored environmental model of a real-world space may be linked location and retrieved during subsequent uses in that location.

FIG. 56 is a flow diagram illustrating an exemplary process for merging of models to produce a shared virtual environment between two or more users, according to an aspect. According to the aspect, the process begins when VR engine 5200 constructs the real-time environmental models in which a shared virtual environment is presented to two or more users 5602. The next step is to retrieve the unified real-time tracking models for each of the two or more users 5604 from a database. VR engine 5200 may then apply the environmental model and the unified tracking models to generate frames of the shared virtual environment at step 5606. These frames allow for each user to be presented to, and positioned appropriately with respect to, other users in the shared virtual environment. This provides multiple users to be able to share a virtual space and to interact with each other through tactile feedback, as well as interact with other virtual objects and surfaces mapped to real-world objects and surfaces. While the shared virtual environment is being presented, VR engine 5200 continuously performs real-time updates to the shared virtual environment 5608. Such real-time updates may be responsive to the following, but is not limited to, user interaction with the shared virtual environment, to user responses to therapy regimens received from therapeutic engine 5300, and to movement of users, real objects, and surfaces within the real-world space.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 13:
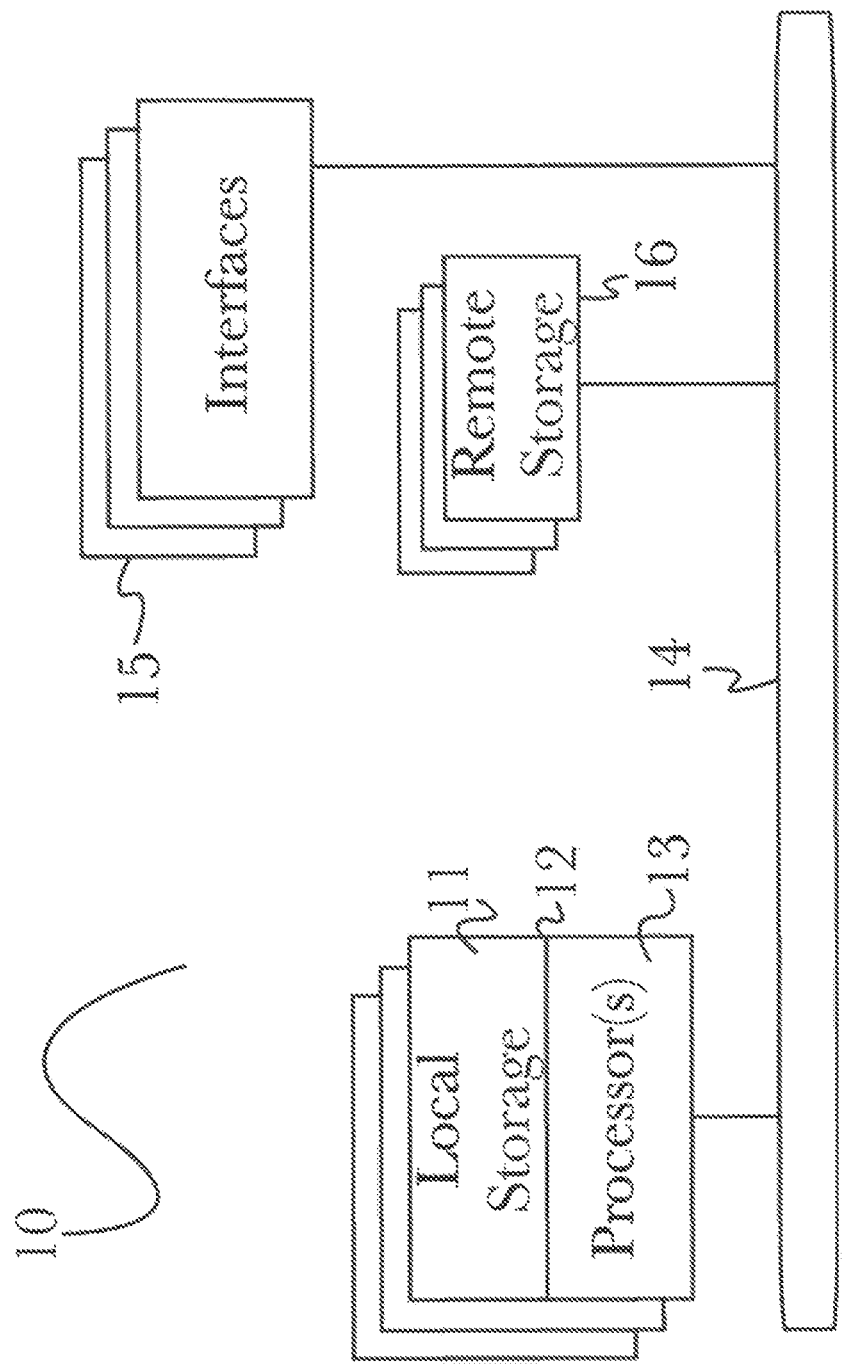
FIG. 13 is a block diagram illustrating an exemplary hardware architecture of a computing device.

Referring now to FIG. 13, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a specific embodiment, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 13 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 14:
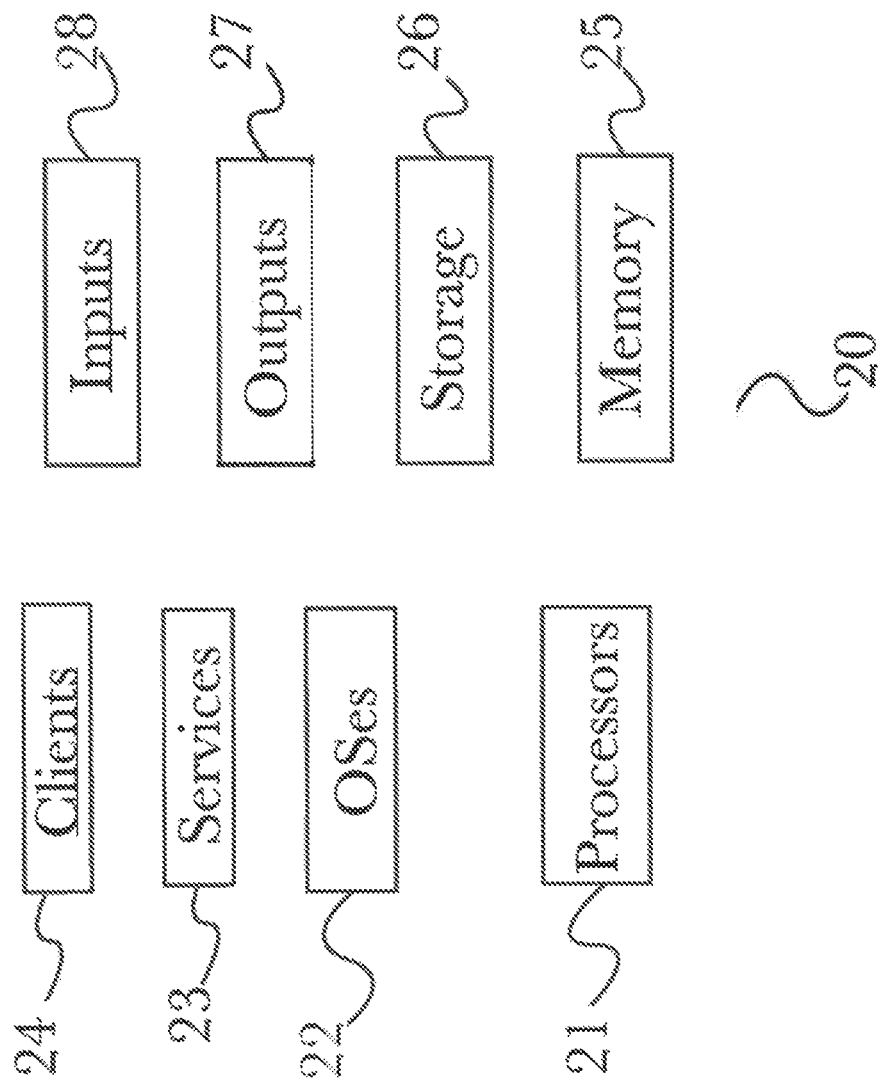
FIG. 14 is a block diagram illustrating an exemplary logical architecture for a client device.

In some embodiments, systems according to the present invention may be implemented on a standalone computing system. Referring now to FIG. 14, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of MICROSOFT WINDOWS™ operating system, APPLE MACOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 13). Examples of storage devices 26 include flash memory, magnetic hard drive, CD-ROM, and/or the like.

Figure 15:
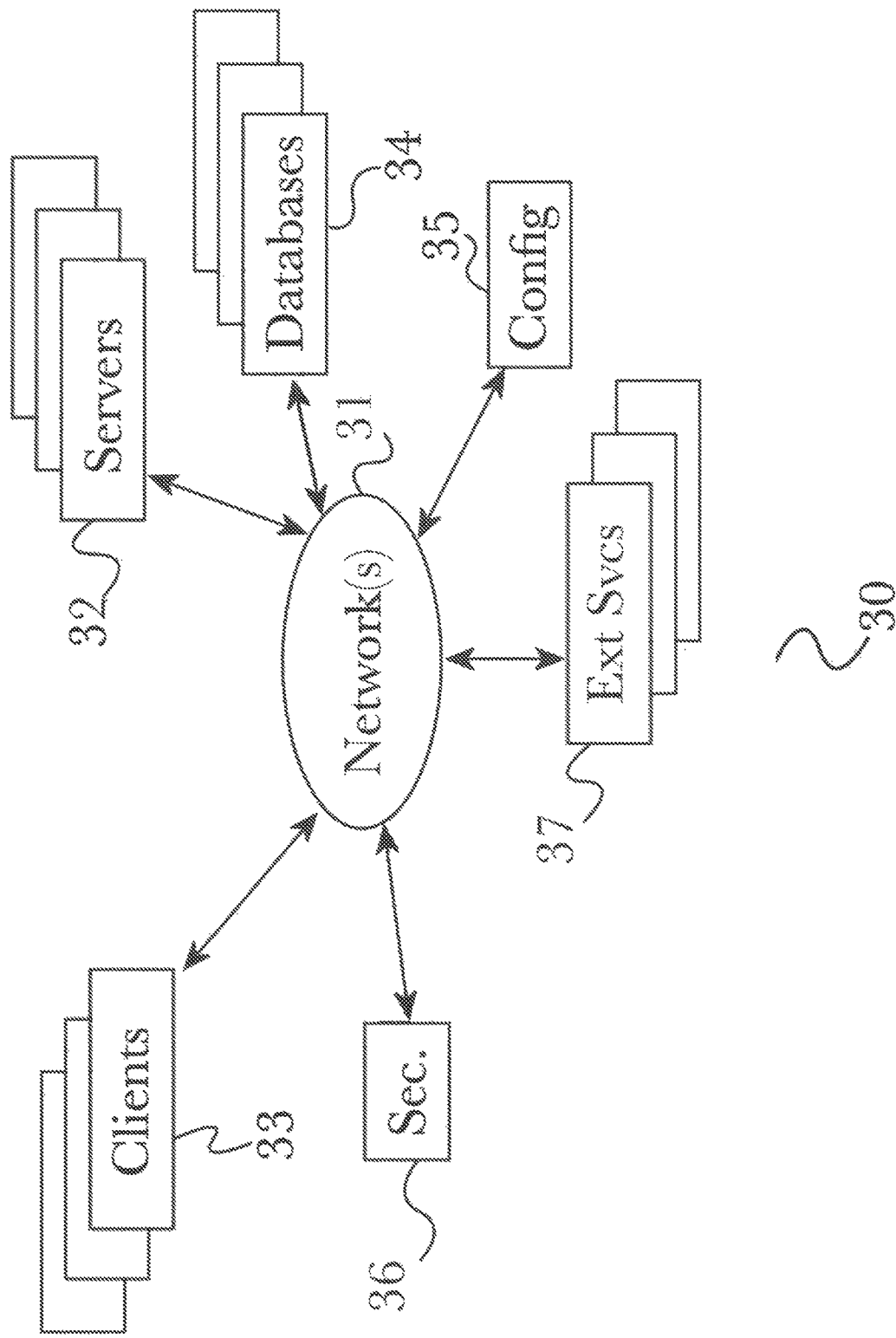
FIG. 15 is a block diagram showing an exemplary architectural arrangement of clients, servers, and external services.

In some embodiments, systems of the present invention may be implemented on a distributed computing network, such as one having any number of clients and/or servers. Referring now to FIG. 15, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in FIG. 14. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

Figure 16:
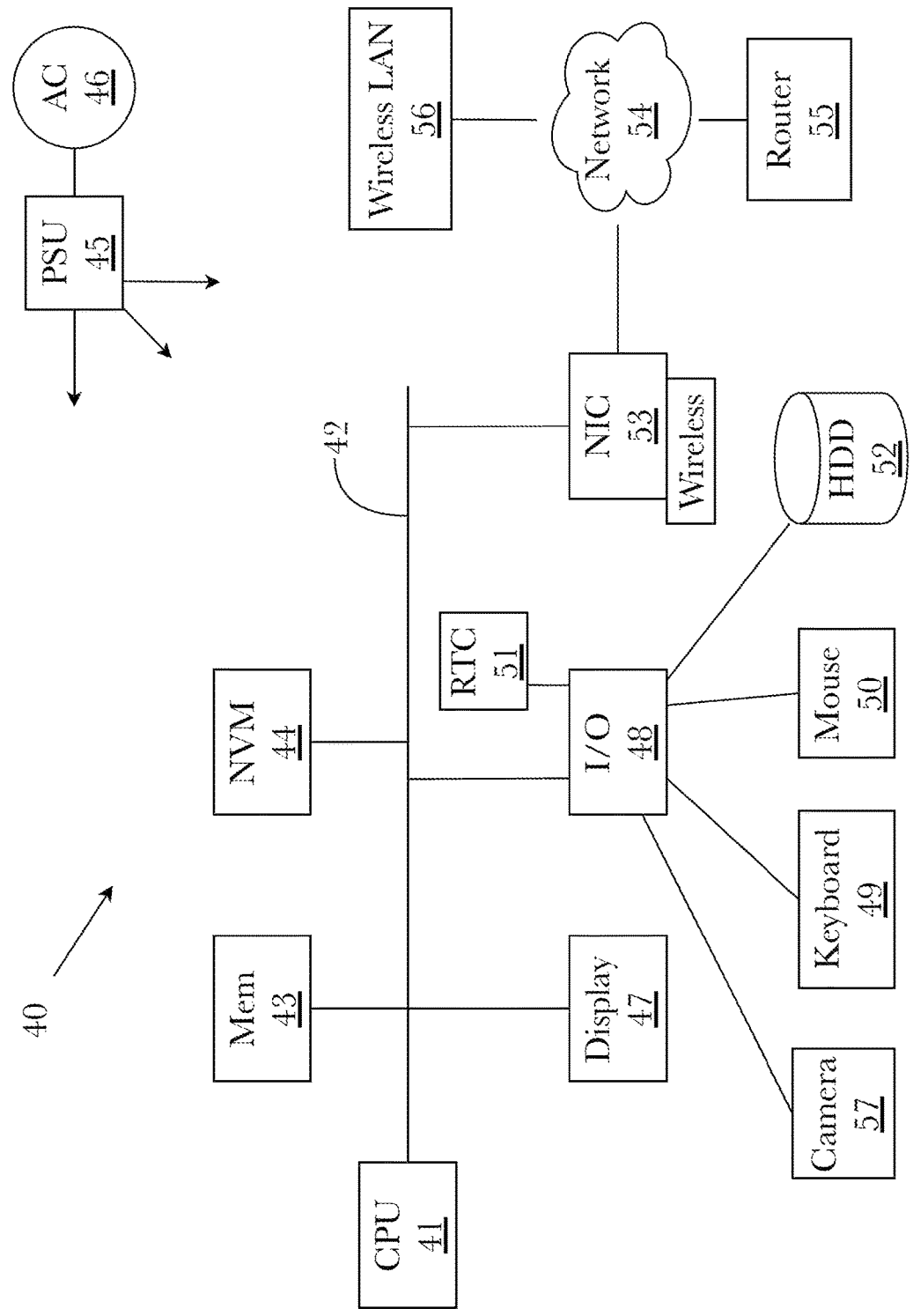
FIG. 16 is another block diagram illustrating an exemplary hardware architecture of a computing device.

FIG. 16 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for virtual reality therapy, comprising:
a computing device comprising a memory, a processor, and a non-volatile data storage device;
a virtual reality engine, comprising a first plurality of programming instructions stored in the memory and operating on the processor, wherein the first plurality of programming instructions, when operating on the processor, causes the computing device to:
receive sensor data from a plurality of sensors;
perform data fusion to integrate the plurality of sensor data;
generate an environmental model of a real-world environment based on the integrated sensor data, in which a shared virtual environment is presented to a first person receiving virtual reality therapy and a second person providing the virtual reality therapy;

generate a unified tracking model based on the integrated sensor data for each of the first and second persons;

for each particular user, apply the environmental model and the tracking model to generate frames of the shared virtual environment corresponding to a real-time field of view of the particular user;

receive response data from a therapeutic engine for the first person;

perform real-time updates to the shared virtual environment based on first and second person interactions with the shared virtual environment, to movement of users and real objects and surfaces within the real-world space, and the response data; and the therapeutic engine, comprising a second plurality of programming instructions stored in the memory and operating on the processor, wherein the second plurality of programming instructions, when operating on the processor, causes the computing device to:

generate a distinct therapeutic layer associated with the first person in the shared virtual environment, wherein the therapeutic layer:

receives a neurological assessment for the first person comprising a neurological condition of the first person;

selects a primary task from a neurological database associated with the neurological condition;

selects an associative activity from the neurological database associated with the neurological condition; and assigns a dual task stimulation for the first person to perform, the dual task stimulation comprising the primary task and the associative activity;

capture the response data to performing primary task and the associative activity;

send the response data to the virtual reality engine; and update the therapeutic layer for the first person based on the real-time updates to the shared virtual environment.

2. The system of claim 1, wherein the therapeutic engine is further configured to:

select a brainwave entrainment therapy for application while the first person is engaged in the dual task stimulation, the therapy comprising a stimulation frequency; and apply the brainwave entrainment therapy by operating virtual elements as transducers at the stimulation frequency while the first person is engaged in the dual task stimulation.

3. The system of claim 2, wherein the primary task is physical exercise and the system further comprises an exercise machine on which the primary task is performed.

4. The system of claim 2, wherein the brainwave entrainment therapy comprises operating the virtual element transducers to provide either visual, auditory, vibratory, or electrical stimulation at a stimulation frequency between 0.5 Hz and 100 Hz.

5. The system of claim 2, comprising a plurality of transducers wherein at least two transducers are of different modalities, and wherein the brainwave entrainment therapy comprises operation of transducers of at least two different modalities.

6. The system of claim 2, comprising a plurality of transducers wherein at least two transducers are of different scales, and wherein the brainwave entrainment therapy comprises operation of transducers of at least two different scales.

7. The system of claim 1, wherein the training regimen comprises brainwave entrainment therapy.

8. The system of claim 1, further comprising a scene object model, wherein the scene object model is used to assist the generation of the environmental model.

9. A method for extended reality therapy with physical interactivity, comprising the steps of:

receiving a plurality of sensor data;

performing data fusion to integrate the plurality of sensor data;

generating an environmental model of a real-world environment based on the integrated sensor data, in which a shared virtual environment is presented to first and second persons;

generating a unified tracking model based on the integrated sensor data for each of the first and second persons;

for each particular user, applying the environmental model and the tracking model to generate frames of the shared virtual environment corresponding to a real-time field of view of the particular user;

receiving user response data from a therapeutic engine;

performing real-time updates to the shared virtual environment based on user interaction with the shared virtual environment, to movement of users and real objects and surfaces within the real-world space, and the user response data;

for each particular user:

generating a distinct therapeutic layer associated with the user in the shared virtual environment, wherein the therapeutic layer:

receives a neurological assessment for each user comprising a neurological condition of the user;

selects a primary task from a neurological database associated with the neurological condition;

selects an associative activity from the neurological database associated with the neurological condition; and assigns a dual task stimulation for the user to perform, the dual task stimulation comprising the primary task and the associative activity;

capturing user response data to performing the primary task and the associative task;

sending the user response data to the virtual reality engine; and updating the therapeutic layer for each user based on the real-time updates to the shared virtual environment.

10. The method of claim 9, further comprising the steps of:

selecting a brainwave entrainment therapy for application while the user is engaged in the dual task stimulation, the therapy comprising a stimulation frequency; and applying the brainwave entrainment therapy by operating virtual elements as transducers at the stimulation frequency while the user is engaged in the dual task stimulation.

11. The method of claim 10, wherein the primary task is physical exercise and the system further comprises an exercise machine on which the primary task is performed.

12. The method of claim 10, wherein the brainwave entrainment therapy comprises operating the virtual element transducers to provide either visual, auditory, vibratory, or electrical stimulation at a stimulation frequency between 0.5 Hz and 100 Hz.

13. The method of claim 10, comprising a plurality of transducers wherein at least two transducers are of different modalities, and wherein the brainwave entrainment therapy comprises operation of transducers of at least two different modalities.

14. The method of claim 10, comprising a plurality of transducers wherein at least two transducers are of different scales, and wherein the brainwave entrainment therapy comprises operation of transducers of at least two different scales.

15. The method of claim 9, wherein the training regimen comprises brainwave entrainment therapy.

16. The method of claim 9, further comprising a scene object model, wherein the scene object model is used to assist the generation of the environmental model.

\* \* \* \* \*